(12) United States Patent
Brace et al.

(10) Patent No.: US 11,458,124 B2
(45) Date of Patent: Oct. 4, 2022

(54) SPIROCYCLIC INDANE ANALOGUES AS IL-17 MODULATORS

(71) Applicant: UCB Biopharma SRL, Brussels (BE)

(72) Inventors: Gareth Neil Brace, Abingdon (GB); Daniel Christopher Brookings, Slough (GB); Gregory Foulkes, Abingdon (GB); Fabien Claude Lecomte, Slough (GB)

(73) Assignee: UCBBiopharma Srl, Brussels (BE)

( * ) Notice: Subject to any disclaimer, the term of this patent is extended or adjusted under 35 U.S.C. 154(b) by 0 days.

(21) Appl. No.: 17/058,973

(22) PCT Filed: Jul. 8, 2019

(86) PCT No.: PCT/EP2019/068300
§ 371 (c)(1),
(2) Date: Nov. 25, 2020

(87) PCT Pub. No.: WO2020/011731
PCT Pub. Date: Jan. 16, 2020

(65) Prior Publication Data
US 2021/0228547 A1 Jul. 29, 2021

(30) Foreign Application Priority Data

Jul. 12, 2018 (GB) .................................. 1811467
Dec. 11, 2018 (GB) .................................. 1820170

(51) Int. Cl.
| | |
|---|---|
| *C07D 405/14* | (2006.01) |
| *A61K 31/422* | (2006.01) |
| *A61K 31/352* | (2006.01) |
| *A61K 31/407* | (2006.01) |
| *A61K 31/4155* | (2006.01) |
| *A61K 31/4245* | (2006.01) |
| *A61K 31/427* | (2006.01) |
| *A61K 31/437* | (2006.01) |
| *C07D 311/96* | (2006.01) |
| *C07D 405/12* | (2006.01) |
| *C07D 413/12* | (2006.01) |
| *C07D 491/107* | (2006.01) |
| *C07D 491/20* | (2006.01) |
| *C07D 493/10* | (2006.01) |

(52) U.S. Cl.
CPC .......... *A61K 31/422* (2013.01); *A61K 31/352* (2013.01); *A61K 31/407* (2013.01); *A61K 31/4155* (2013.01); *A61K 31/427* (2013.01); *A61K 31/4245* (2013.01); *A61K 31/437* (2013.01); *C07D 311/96* (2013.01); *C07D 405/12* (2013.01); *C07D 405/14* (2013.01); *C07D 413/12* (2013.01); *C07D 491/107* (2013.01); *C07D 491/20* (2013.01); *C07D 493/10* (2013.01)

(58) Field of Classification Search
CPC .............. A61K 31/438; A61K 31/4245; A61K 31/427; A61K 31/352; A61K 31/422; A61K 31/4155; A61K 31/407; C07D 405/14; C07D 323/04; C07D 491/107; C07D 491/20; C07D 405/12; C07D 497/10
USPC .......... 514/406, 409, 364, 372, 378; 546/15; 548/357.5, 214, 247, 409, 126; 549/331
See application file for complete search history.

(56) References Cited

FOREIGN PATENT DOCUMENTS

| | | | |
|---|---|---|---|
| EP | 0431943 A2 | 6/1991 | |
| EP | 2072519 A1 | 6/2009 | |
| WO | 00/37456 A1 | 6/2000 | |
| WO | WO2000037456 * | 6/2000 | .......... C07D 401/04 |
| WO | 2004/007458 A1 | 1/2004 | |
| WO | 2007/048070 A2 | 4/2007 | |
| WO | 2008/060789 A2 | 5/2008 | |
| WO | 2010/045251 A2 | 4/2010 | |
| WO | 2011/073119 A1 | 6/2011 | |
| WO | 2012/004378 A1 | 1/2012 | |
| WO | 2014/047020 A1 | 3/2014 | |
| WO | 2015/017335 A1 | 2/2015 | |
| WO | 2015/170266 A1 | 11/2015 | |
| WO | 2016/044770 A1 | 3/2016 | |
| WO | 2017/069224 A1 | 4/2017 | |
| WO | 2017/108203 A1 | 6/2017 | |
| WO | 2017/109061 A1 | 6/2017 | |
| WO | 2018/003962 A1 | 1/2018 | |
| WO | WO2018106646 * | 6/2018 | .......... C07D 401/04 |
| WO | 2018/229079 A1 | 12/2018 | |

OTHER PUBLICATIONS

Butkevich, A N. et al, Two-Step One-Pot Synthesis of Benzoannulated Spiroacetals by Suzuki-Miyaura coupling/Acid-Catalyzed Spiroacetalization, Organic Letters, 2012, pp. 4998-5001, vol. 14 No. 19.

(Continued)

*Primary Examiner* — Jeffrey H Murray
(74) *Attorney, Agent, or Firm* — McDonnell Boehnen Hulbert & Berghoff LLP

(57) ABSTRACT

A series of substituted spirocyclic indane derivatives of Formula (I), and analogues thereof, being potent modulators of human IL-17 activity, are accordingly of benefit in the treatment and/or prevention of various human ailments, including inflammatory and autoimmune disorders.

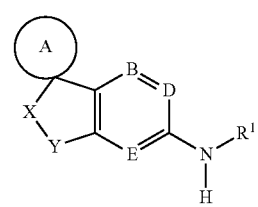

(I)

15 Claims, No Drawings

(56) References Cited

OTHER PUBLICATIONS

Fader, L E et al, Optimization of a 1,5-dihydrobenzo[b][1,4]diazepine-2,4-dione series of HIV capsid assembly inhibitors 1: Addressing configurational instability through scaffold modification, Bioorganic & Medicinal Chemistry Letters, 2013, 3396-3400, 23.

Hahn, C R et al., Cyclopropyl Aromatic Chemistry. I. Utraviolet Spectra of Certain Cyclopropyl Aromatic Systems, The American Chemical Society, Jun. 1, 1969, 3558-3566, vol. 91 No. 13.

Cendhai F, A. M. et al, Foldamers with unusual structural architecture from spirobi(indane) building blocks, ChemComm, 2008, 2541-2543.

Lasko, L M et al, Discovery of a selective catalytic p300/CBP inhibitor that targets lineage-specific tumors, Nature, Oct. 5, 2017, pp. 128-132, vol. 550.

Michaelides M.R. et al, Discovery of Spiro Oxazolidinediones as Selective, Orally Bioavailable Inhibitors of p300/CBP Histone Acetyltransferases, Med Chern Lett, 2018, pp. 28-33, 9.

International Search Report of International Application No. PCT/EP2019/068300 dated Sep. 23, 2019, 10 pages.

\* cited by examiner

SPIROCYCLIC INDANE ANALOGUES AS IL-17 MODULATORS

CROSS-REFERENCE TO RELATED APPLICATIONS

This application is a U.S. national phase of International Application No. PCT/EP2019/068300, filed Jul. 8, 2019, which claims priority from Great Britain Application no. 1811467.8, filed Jul. 12, 2018, and Great Britain Application no. 1820170.7, filed, Dec. 11, 2018, the disclosure of each of which is hereby incorporated by reference in its entirety.

The present invention relates to heterocyclic compounds, and to their use in therapy. More particularly, this invention is concerned with pharmacologically active spirocyclic indane derivatives, and analogues thereof. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.*, 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.*, 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.*, 2009, 27, 485-517). IL-17A and IL-17F are expressed as homodimers, but may also be expressed as the IL-17A/F heterodimer (Wright et al., *J. Immunol.*, 2008, 181, 2799-2805). IL-17A and F signal through the receptors IL-17R, IL-17RC or an IL-17RA/RC receptor complex (Gaffen, *Cytokine*, 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

Co-pending international patent application PCT/EP2018/065558 (published on 20 Dec. 2018 as WO 2018/229079) describes spirocyclic oxoindoline derivatives, and analogues thereof, that are potent modulators of human IL-17 activity, are therefore beneficial in the treatment of human ailments, including inflammatory and autoimmune disorders.

None of the prior art available to date, however, discloses or suggests the precise structural class of spirocyclic indane derivatives, and analogues thereof, as provided by the present invention.

The present invention provides a compound of formula (I) or an N-oxide thereof, or a pharmaceutically acceptable salt thereof:

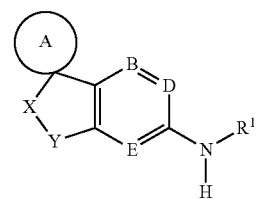

(I)

wherein ring A represents $C_{3-9}$ cycloalkyl, $C_{3-7}$ heterocycloalkyl or $C_{4-9}$ heterobicycloalkyl, any of which groups may be optionally substituted by one or more substituents;

B represents C—$R^2$ or N;

D represents C—$R^3$ or N;

E represents C—$R^4$ or N;

—X—Y— represents —O—C($Y^1$)($Y^2$)—, —N($X^3$)—C($Y^1$)($Y^2$)—, —N($X^3$)—S(O)$_2$—, —C($X^1$)($X^2$)—O—, —C($X^1$)($X^2$)—N($Y^3$)—, —C($X^1$)($X^2$)—C($Y^1$)($Y^2$)—, —C($X^1$)($X^2$)—S—, —C($X^1$)($X^2$)—S(O)—, —C($X^1$)($X^2$)—S(O)$_2$—, —C($X^1$)($X^2$)—S(O)(N—$Y^4$)—, —C(O)—O—, —C(O)—C($Y^1$)($Y^2$)—, —C(O)—S—, —C(S)—O—, —C(S)—N($Y^3$)—, —C(S)—C($Y^1$)($Y^2$)—, —S—C($Y^1$)($Y^2$)—, —S(O)—C($Y^1$)($Y^2$)—, —S(O)$_2$—N($Y^3$)—, —S(O)$_2$—C($Y^1$)($Y^2$)—, —S(O)(N—$X^4$)—N($Y^3$)—, —S(O)(N—$X^4$)—C($Y^1$)($Y^2$)— or —C($X^1$)=C($Y^1$)—;

$R^1$ represents —COR$^a$ or —SO$_2$R$^b$; or $R^1$ represents $C_{1-6}$ alkyl, $C_{3-9}$ cycloalkyl, $C_{3-9}$ cycloalkyl($C_{1-6}$)alkyl, $C_{5-9}$ spirocycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^2$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;

$R^3$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;

$R^4$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;

$R^a$ represents hydrogen; or $R^a$ represents $C_{1-6}$ alkyl, $C_{2-7}$ alkenyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{4-9}$ bicycloalkylidenyl($C_{1-6}$)alkyl, $C_{5-9}$ spirocycloalkyl($C_{1-6}$)alkyl, $C_{9-11}$ tricycloalkyl-($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkylidenyl($C_{1-6}$)alkyl, heteroaryl or heteroaryl($C_{1-6}$)alkyl, any of which groups may be optionally substituted by one or more substituents;

$R^b$ represents $C_{1-6}$ alkyl, $C_{2-7}$ alkenyl, $C_{3-9}$ cycloalkyl, $C_{3-9}$ cycloalkyl($C_{1-6}$)alkyl, $C_{3-9}$ cycloalkylidenyl($C_{1-6}$)alkyl, $C_{4-9}$ bicycloalkyl($C_{1-6}$)alkyl, $C_{4-9}$ bicycloalkylidenyl-($C_{1-6}$) alkyl, $C_{5-9}$ spirocycloalkyl($C_{1-6}$)alkyl, $C_{9-11}$ tricycloalkyl ($C_{1-6}$)alkyl, aryl, aryl($C_{1-6}$)-alkyl, $C_{3-7}$ heterocycloalkyl, $C_{3-7}$ heterocycloalkyl($C_{1-6}$)alkyl, $C_{3-7}$ heterocycloalkylidenyl-$(C_{1-6})$alkyl, heteroaryl or heteroaryl$(C_{1-6})$alkyl, any of which groups may be optionally substituted by one or more substituents;

$X^1$ represents hydrogen, halogen, cyano, $C_{1-6}$ alkyl, trifluoromethyl, $(C_{1-6})$alkoxy-$(C_{1-6})$alkyl, amino$(C_{1-6})$alkyl, $C_{3-7}$ cycloalkyl, aryl, $C_{3-7}$ heterocycloalkyl or heteroaryl;

$X^2$ represents hydrogen, halogen or $C_{1-6}$ alkyl;

$X^3$ represents hydrogen or $C_{1-6}$ alkyl;

$X^4$ represents hydrogen or $C_{1-6}$ alkyl;

$Y^1$ represents hydrogen, halogen, cyano, $C_{1-6}$ alkyl, trifluoromethyl, $(C_{1-6})$alkoxy-$(C_{1-6})$alkyl, amino$(C_{1-6})$alkyl, $C_{3-7}$ cycloalkyl, aryl, $C_{3-7}$ heterocycloalkyl or heteroaryl;

$Y^2$ represents hydrogen, halogen or $C_{1-6}$ alkyl;

$Y^3$ represents hydrogen or $C_{1-6}$ alkyl; and $Y^4$ represents hydrogen or $C_{1-6}$ alkyl.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable alkenyl groups which may be present on the compounds of use in the invention include straight-chained and branched $C_{2-7}$ alkenyl groups, for example $C_{2-4}$ alkenyl groups. Typical examples include vinyl, allyl and buten-1-yl.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, tetrahydronaphthalenyl, cycloheptyl, benzocycloheptenyl, cyclooctyl and cyclononanyl.

The term "$C_{3-9}$ cycloalkylidenyl" as used herein refers to monovalent groups of 3 to 9 carbon atoms derived from a saturated monocyclic hydrocarbon, optionally comprising benzo-fused analogues thereof, attached to the remainder of the molecule via a C=C double bond. Typically, such groups include cyclobutylidenyl, cyclopentylidenyl, cyclohexylidenyl, cycloheptylidenyl, cyclooctylidenyl and cyclononanylidenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl, bicyclo-[2.2.1]heptanyl, bicyclo[2.2.2]octanyl, bicyclo[3.3.0]octanyl and bicyclo[3.2.1]octanyl.

The term "$C_{4-9}$ bicycloalkylidenyl" as used herein refers to monovalent groups of 4 to 9 carbon atoms derived from a saturated bicyclic hydrocarbon, attached to the remainder of the molecule via a C=C double bond. Typically, such groups include bicyclo[3.1.0]hexanylidenyl, bicyclo[2.2.1] heptanylidenyl and bicyclo[3.2.1]octanyliden-yl.

The term "$C_{5-9}$ spirocycloalkyl" as used herein refers to saturated bicyclic ring systems containing 5 to 9 carbon atoms, in which the two rings are linked by a common atom. Suitable spirocycloalkyl groups include spiro[2.3]hexanyl, spiro[2.4]heptanyl, spiro[3.3]heptanyl, spiro[3.4]octanyl, spiro[3.5]nonanyl and spiro[4.4]nonanyl.

The term "$C_{9-11}$ tricycloalkyl" as used herein refers to monovalent groups of 9 to 11 carbon atoms derived from a saturated tricyclic hydrocarbon. Typical tricycloalkyl groups include adamantanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl$(C_{1-6})$alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkylidenyl" as used herein refers to saturated monocyclic rings containing 3 to 7 carbon atoms and at least one heteroatom selected from oxygen, sulphur and nitrogen, attached to the remainder of the molecule via a C=C double bond. Typically, such groups include tetrahydropyranylidenyl and piperidinylidenyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]heptanyl, 6-azabicyclo[3.2.0]heptanyl, 6-oxabicyclo[3.1.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 8-oxabicyclo[3.2.1]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, pyrazolo[1,5-a]pyrazinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo-[2,1-b]thiazolyl, imidazo[1,2-a]pyridinyl, imidazo[4,5-b]pyridinyl, imidazo[1,2-b]-pyridazinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$.

Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, ring A represents optionally substituted $C_{3-9}$ cycloalkyl. In one aspect of that embodiment, ring A represents optionally substituted $C_{4-7}$ cycloalkyl.

In a second embodiment, ring A represents optionally substituted $C_{3-7}$ heterocyclo-alkyl. In one aspect of that embodiment, ring A represents optionally substituted $C_{4-6}$ heterocycloalkyl.

In a third embodiment, ring A represents optionally substituted $C_{4-9}$ heterobicyclo-alkyl. In one aspect of that embodiment, ring A represents optionally substituted $C_{5-7}$ heterobicycloalkyl.

Typically, ring A represents cyclopropyl, cyclobutyl, cyclopentyl, cyclohexyl, cycloheptyl, cyclooctyl, cyclononanyl, oxetanyl, azetidinyl, tetrahydrofuranyl, pyrrolidinyl, oxazolidinyl, thiazolidinyl, isothiazolidinyl, imidazolidinyl, tetrahydro-pyranyl, tetrahydrothiopyranyl, piperidinyl, piperazinyl, homopiperazinyl, morpholinyl, thiomorpholinyl, azepanyl, oxazepanyl, diazepanyl, thiadiazepanyl, azocanyl, 6-oxa-bicyclo[3.1.0]hexanyl, 6-oxabicyclo[3.1.1]heptanyl or 8-oxabicyclo[3.2.1]octanyl, any of which groups may be optionally substituted by one or more substituents.

Suitably, ring A represents pyrrolidinyl, tetrahydropyranyl, tetrahydrothiopyranyl or piperidinyl, any of which groups may be optionally substituted by one or more substituents.

In a particular embodiment, ring A represents tetrahydropyranyl, which group may be optionally substituted by one or more substituents.

Typical examples of optional substituents on ring A include one, two or three substituents independently selected from $C_{1-6}$ alkyl, halogen, cyano, trifluoromethyl, hydroxy, oxo, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, imino, $C_{1-6}$ alkylamino and di($C_{1-6}$)alkylamino.

Suitable examples of optional substituents on ring A include one, two or three substituents independently selected from $C_{1-6}$ alkyl, oxo and imino.

Typical examples of particular substituents on ring A include one, two or three substituents independently selected from methyl, fluoro, chloro, bromo, cyano, trifluoro-methyl, hydroxy, oxo, methoxy, methylthio, methylsulphinyl, methylsulphonyl, acetyl, amino, imino, methylamino and dimethylamino.

Suitable examples of particular substituents on ring A include one, two or three substituents independently selected from methyl, oxo and imino.

Typical values of ring A include pyrrolidinyl, tetrahydropyranyl, (methyl)-tetrahydropyranyl, tetrahydrothiopyranyl, (oxo)tetrahydrothiopyranyl, (dioxo)tetrahydro-thiopyranyl, (imino)(oxo)tetrahydrothiopyranyl and piperidinyl.

A particular value of ring A is tetrahydropyranyl.

In one embodiment, B represents C—R². In another embodiment, B represents N.

In one embodiment, D represents C—R³. In another embodiment, D represents N.

In one embodiment, E represents C—R⁴. In another embodiment, E represents N.

In a first embodiment, B represents C—R², D represents C—R³ and E represents C—R⁴.

In a second embodiment, B represents C—R², D represents C—R³ and E represents N.

In a third embodiment, B represents C—R², D represents N and E represents C—R⁴.

In a fourth embodiment, B represents C—R², D represents N and E represents N.

In a fifth embodiment, B represents N, D represents C—R³ and E represents C—R⁴.

In a sixth embodiment, B represents N, D represents C—R³ and E represents N.

In a seventh embodiment, B represents N, D represents N and E represents C—R⁴.

In an eighth embodiment, B represents N, D represents N and E represents N.

Suitably, B represents C—R²; D represents C—R³ or N; and E represents C—R⁴.

Suitably, the present invention provides a compound of formula (I-1), (I-2), (I-3), (I-4) or (I-5) or an N-oxide thereof, or a pharmaceutically acceptable salt thereof:

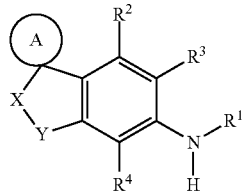
(I-1)

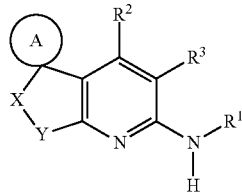
(I-2)

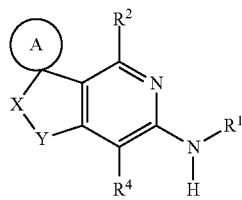
(I-3)

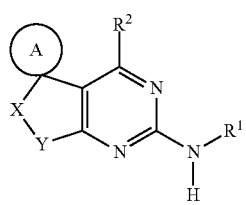
(I-4)

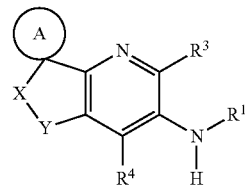
(I-5)

wherein A, X, Y, R¹, R², R³ and R⁴ are as defined above.

Appositely, the present invention provides a compound of formula (I-1) or (I-3) as defined above, or an N-oxide thereof, or a pharmaceutically acceptable salt thereof:

In a first embodiment, —X—Y— represents —O—C(Y¹)(Y²)—.

In a second embodiment, —X—Y— represents —N(X³)—C(Y¹)(Y²)—.

In a third embodiment, —X—Y— represents —N(X³)—S(O)₂—.

In a fourth embodiment, —X—Y— represents —C(X¹)(X²)—.

In a fifth embodiment, —X—Y— represents —C(X¹)(X²)—N(Y³)—.

In a sixth embodiment, —X—Y— represents —C(X¹)(X²)—C(Y¹)(Y²)—.

In a seventh embodiment, —X—Y— represents —C(X¹)(X²)—S—.

In an eighth embodiment, —X—Y— represents —C(X¹)(X²)—S(O)—.

In a ninth embodiment, —X—Y— represents —C(X¹)(X²)—S(O)₂—.

In a tenth embodiment, —X—Y— represents —C(X¹)(X²)—S(O)(N—Y⁴)—.

In an eleventh embodiment, —X—Y— represents —C(O)—O—.

In a twelfth embodiment, —X—Y— represents —C(O)—C(Y¹)(Y²)—.

In a thirteenth embodiment, —X—Y— represents —C(O)—S—.

In a fourteenth embodiment, —X—Y— represents —C(S)—O—.

In a fifteenth embodiment, —X—Y— represents —C(S)—N(Y³)—.

In a sixteenth embodiment, —X—Y— represents —C(S)—C(Y¹)(Y²)—.

In a seventeenth embodiment, —X—Y— represents —S—C(Y¹)(Y²)—.

In an eighteenth embodiment, —X—Y— represents —S(O)—C(Y¹)(Y²)—.

In a nineteenth embodiment, —X—Y— represents —S(O)₂—N(Y³)—.

In a twentieth embodiment, —X—Y— represents —S(O)₂—C(Y¹)(Y²)—.

In a twenty-first embodiment, —X—Y— represents —S(O)(N—X⁴)—N(Y³)—.

In a twenty-second embodiment, —X—Y— represents —S(O)(N—X⁴)—C(Y¹)(Y²)—.

In a twenty-third embodiment, —X—Y— represents —C(X¹)=C(Y¹)—.

Typically, —X—Y— represents —C(X¹)(X²)—O—, —C(X¹)(X²)—N(Y³)—, —C(X¹)(X²)—C(Y¹)(Y²)—, —C(O)—O— or —C(X¹)=C(Y¹)—.

Suitably, the present invention provides a compound of formula (I-11), (I-12), (I-13), (I-14) or (I-15) or an N-oxide thereof, or a pharmaceutically acceptable salt thereof:

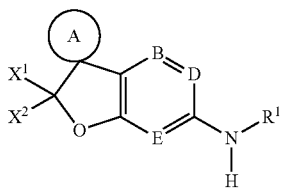
(I-11)

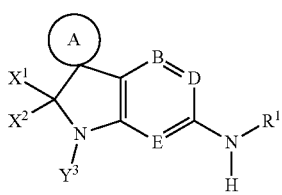
(I-12)

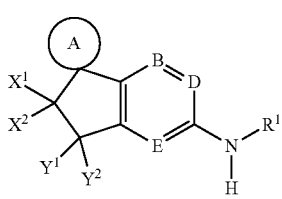
(I-13)

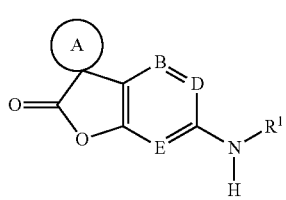
(I-14)

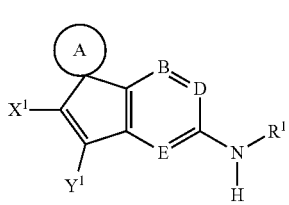
(I-15)

wherein A, B, D, E, $X^1$, $X^2$, $Y^1$, $Y^2$, $Y^3$ and $R^1$ are as defined above.

Typical examples of optional substituents on $R^1$ include one, two or three substituents independently selected from $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on $R^1$ include one, two or three substituents independently selected from methyl, fluoro, chloro, bromo, cyano, trifluoro-methyl, hydroxy, oxo, methoxy, methylthio, methylsulphinyl, methylsulphonyl, acetyl, amino, methylamino and dimethylamino.

Suitably, $R^1$ represents —$COR^a$.

Typically, $R^2$ represents hydrogen or halogen.

In a first embodiment, $R^2$ represents hydrogen. In a second embodiment, $R^2$ represents halogen. In a first aspect of that embodiment, $R^2$ represents fluoro. In a second aspect of that embodiment, $R^2$ represents chloro. In a third embodiment, $R^2$ represents cyano. In a fourth embodiment, $R^2$ represents $C_{1-6}$ alkyl, especially methyl. In a fifth embodiment, $R^2$ represents fluoromethyl. In a sixth embodiment, $R^2$ represents difluoromethyl. In a seventh embodiment, $R^2$ represents trifluoromethyl. In an eighth embodiment, $R^2$ represents hydroxy. In a ninth embodiment, $R^2$ represents $C_{1-6}$ alkoxy, especially methoxy. In a tenth embodiment, $R^2$ represents difluoromethoxy. In an eleventh embodiment, $R^2$ represents trifluoromethoxy. In a twelfth embodiment, $R^2$ represents $C_{1-6}$ alkylsulphinyl, especially methylsulphinyl. In a thirteenth embodiment, $R^2$ represents $C_{1-6}$ alkylsulphonyl, especially methylsulphonyl.

Suitably, $R^2$ represents hydrogen or fluoro.

Typically, $R^3$ represents hydrogen or halogen.

In a first embodiment, $R^3$ represents hydrogen. In a second embodiment, $R^3$ represents halogen. In a first aspect of that embodiment, $R^3$ represents fluoro. In a second aspect of that embodiment, $R^3$ represents chloro. In a third embodiment, $R^3$ represents cyano. In a fourth embodiment, $R^3$ represents $C_{1-6}$ alkyl, especially methyl. In a fifth embodiment, $R^3$ represents fluoromethyl. In a sixth embodiment, $R^3$ represents difluoromethyl. In a seventh embodiment, $R^3$ represents trifluoromethyl. In an eighth embodiment, $R^3$ represents hydroxy. In a ninth embodiment, $R^3$ represents $C_{1-6}$ alkoxy, especially methoxy. In a tenth embodiment, $R^3$ represents difluoromethoxy. In an eleventh embodiment, $R^3$ represents trifluoromethoxy. In a twelfth embodiment, $R^3$ represents $C_{1-6}$ alkylsulphinyl, especially methylsulphinyl. In a thirteenth embodiment, $R^3$ represents $C_{1-6}$ alkylsulphonyl, especially methylsulphonyl.

Appositely, $R^3$ represents hydrogen, fluoro or chloro.

Suitably, $R^3$ represents hydrogen or fluoro.

In a first embodiment, $R^4$ represents hydrogen. In a second embodiment, $R^4$ represents halogen. In a first aspect of that embodiment, $R^4$ represents fluoro. In a second aspect of that embodiment, $R^4$ represents chloro. In a third embodiment, $R^4$ represents cyano. In a fourth embodiment, $R^4$ represents $C_{1-6}$ alkyl, especially methyl. In a fifth embodiment, $R^4$ represents fluoromethyl. In a sixth embodiment, $R^4$ represents difluoromethyl. In a seventh embodiment, $R^4$ represents trifluoromethyl. In an eighth embodiment, $R^4$ represents hydroxy. In a ninth embodiment, $R^4$ represents $C_{1-6}$ alkoxy, especially methoxy. In a tenth embodiment, $R^4$ represents difluoromethoxy. In an eleventh embodiment, $R^4$ represents trifluoromethoxy. In a twelfth embodiment, $R^4$ represents $C_{1-6}$ alkylsulphinyl, especially methylsulphinyl. In a thirteenth embodiment, $R^4$ represents $C_{1-6}$ alkylsulphonyl, especially methylsulphonyl.

In a particular embodiment, $R^a$ is other than hydrogen.

Typically, $R^a$ represents $C_{3-9}$ cycloalkyl($C_{1-6}$)alkyl or $C_{3-9}$ cycloalkylidenyl($C_{1-6}$)-alkyl, either of which groups may be optionally substituted by one or more substituents.

Suitable values of $R^a$ include cyclohexylmethyl, cyclooctylmethyl and benzo-cyclobutylidenylmethyl, any of which groups may be optionally substituted by one or more substituents.

Favoured examples of optional substituents on $R^a$ include one, two or three substituents independently selected from halogen, cyano, nitro, $C_{1-6}$ alkyl, trifluoro-methyl, trifluoroethyl, phenyl, hydroxy, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkyl-sulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylamino-sulfonyl, di($C_{1-6}$)alkylaminosulfonyl, —$R^{5a}$, —NH-$COR^6$, —NHS(O)$_2R^6$, —$R^7$, —NHR$^7$ and —CONHR$^7$, wherein $R^{5a}$, $R^6$ and $R^7$ are as defined below.

Selected examples of optional substituents on $R^a$ include one, two or three substituents independently selected from halogen, $C_{1-6}$ alkyl and —NHCOR$^6$, wherein R$^6$ is as defined below.

Favoured examples of specific substituents on $R^a$ include one, two or three substituents independently selected from fluoro, chloro, bromo, cyano, nitro, methyl, ethyl, isopropyl, tert-butyl, trifluoromethyl, trifluoroethyl, phenyl, hydroxy, oxo, methoxy, isopropoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl, dimethylamino-sulfonyl, —R$^{5a}$, —NHCOR$^6$, —NHS(O)$_2$R$^6$, —R$^7$, —NHR$^7$ and —CONHR$^7$, wherein R$^{5a}$, R$^6$ and R$^7$ are as defined below.

Selected examples of specific substituents on $R^a$ include one, two or three substituents independently selected from chloro, methyl and —NHCOR$^6$, wherein R$^6$ is as defined below.

Typically, $R^b$ represents $C_{3-9}$ cycloalkyl($C_{1-6}$)alkyl or $C_{3-9}$ cycloalkylidenyl($C_{1-6}$)-alkyl, either of which groups may be optionally substituted by one or more substituents.

Suitable values of $R^b$ include cyclohexylmethyl, cyclooctylmethyl and benzo-cyclobutylidenylmethyl, any of which groups may be optionally substituted by one or more substituents.

Favoured examples of optional substituents on $R^b$ include one, two or three substituents independently selected from halogen, cyano, nitro, $C_{1-6}$ alkyl, trifluoro-methyl, trifluoroethyl, phenyl, hydroxy, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkyl-sulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylamino-sulfonyl, di($C_{1-6}$)alkylaminosulfonyl, —R$^{5a}$, —NHCOR$^6$, —NHS(O)$_2$R$^6$, —R$^7$, —NHR$^7$ and —CONHR$^7$, wherein R$^{5a}$, R$^6$ and R$^7$ are as defined below.

Selected examples of optional substituents on $R^b$ include one, two or three substituents independently selected from halogen, $C_{1-6}$ alkyl and —NHCOR$^6$, wherein R$^6$ is as defined below.

Favoured examples of specific substituents on $R^b$ include one, two or three substituents independently selected from fluoro, chloro, bromo, cyano, nitro, methyl, ethyl, isopropyl, tert-butyl, trifluoromethyl, trifluoroethyl, phenyl, hydroxy, oxo, methoxy, isopropoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl, dimethylamino-sulfonyl, —R$^{5a}$, —NHCOR$^6$, —NHS(O)$_2$R$^6$, —R$^7$, —NHR$^7$ and —CONHR$^7$, wherein R$^{5a}$, R$^6$ and R$^7$ are as defined below.

Selected examples of specific substituents on $R^b$ include one, two or three substituents independently selected from chloro, methyl and —NHCOR$^6$, wherein R$^6$ is as defined below.

A particular sub-class of compounds according to the invention is represented by the compounds of formula (IA) and N-oxides thereof, and pharmaceutically acceptable salts thereof:

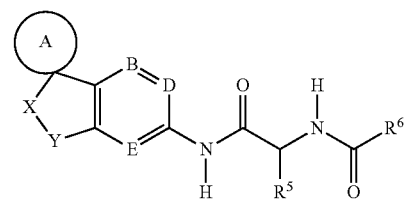

(IA)

wherein

A, B, D, E, X and Y are as defined above;

R$^5$ represents hydrogen; or R$^5$ represents $C_{1-5}$ alkyl, $C_{3-9}$ cycloalkyl, $C_{3-9}$ cyclo-alkyl($C_{1-5}$)alkyl, $C_{4-9}$ bicycloalkyl, $C_{4-9}$ bicycloalkyl($C_{1-5}$)alkyl, $C_{5-9}$ spirocycloalkyl, $C_{5-9}$ spirocycloalkyl($C_{1-5}$)alkyl, $C_{9-11}$ tricycloalkyl, $C_{9-11}$ tricycloalkyl($C_{1-5}$)alkyl, aryl, aryl-($C_{1-5}$)alkyl, $C_{3-7}$ heterocycloalkyl, $C_{3-7}$ heterocycloalkyl($C_{1-5}$)alkyl, heteroaryl or heteroaryl($C_{1-5}$)alkyl, any of which groups may be optionally substituted by one or more substituents;

R$^6$ represents —NR$^{6a}$R$^{6b}$ or —OR$^6$; or R$^6$ represents $C_{1-9}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl, heteroaryl($C_{1-6}$)alkyl or spiro[($C_{3-7}$)heterocycloalkyl][heteroaryl], any of which groups may be optionally substituted by one or more substituents;

R$^{6a}$ represents hydrogen; or R$^{6a}$ represents $C_{1-6}$ alkyl, $C_{3-7}$ cycloalkyl, $C_{3-7}$ cyclo-alkyl($C_{1-6}$)alkyl, aryl, aryl($C_{1-6}$)alkyl, $C_{3-7}$ heterocycloalkyl, $C_{3-7}$ heterocycloalkyl($C_{1-6}$)-alkyl, heteroaryl, heteroaryl($C_{1-6}$)alkyl or spiro[($C_{3-7}$)heterocycloalkyl][heteroaryl], any of which groups may be optionally substituted by one or more substituents;

R$^{6b}$ represents hydrogen or $C_{1-6}$ alkyl; and

R$^{6c}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

A second sub-class of compounds according to the invention is represented by the compounds of formula (IB) and N-oxides thereof, and pharmaceutically acceptable salts thereof:

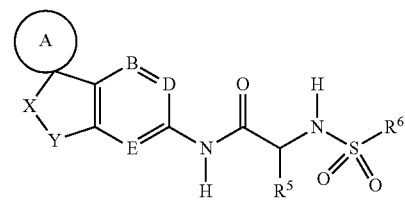

(IB)

wherein

A, B, D, E, X, Y, R$^5$ and R$^6$ are as defined above.

A third sub-class of compounds according to the invention is represented by the compounds of formula (IC) and N-oxides thereof, and pharmaceutically acceptable salts thereof:

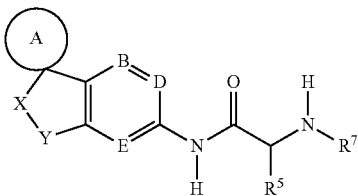

(IC)

wherein

A, B, D, E, X, Y and $R^5$ are as defined above; and $R^7$ represents aryl, heteroaryl or spiro[($C_{3-7}$)heterocycloalkyl][heteroaryl], any of which groups may be optionally substituted by one or more substituents.

A fourth sub-class of compounds according to the invention is represented by the compounds of formula (ID) and N-oxides thereof, and pharmaceutically acceptable salts thereof:

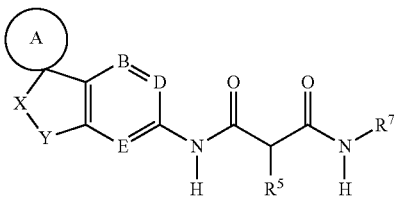

(ID)

wherein

A, B, D, E, X, Y, $R^5$ and $R^7$ are as defined above.

A fifth sub-class of compounds according to the invention is represented by the compounds of formula (IE) and N-oxides thereof, and pharmaceutically acceptable salts thereof:

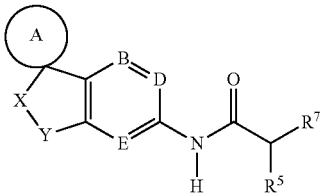

(IE)

wherein

A, B, D, E, X, Y, $R^5$ and $R^7$ are as defined above.

A sixth sub-class of compounds according to the invention is represented by the compounds of formula (IF) and N-oxides thereof, and pharmaceutically acceptable salts thereof:

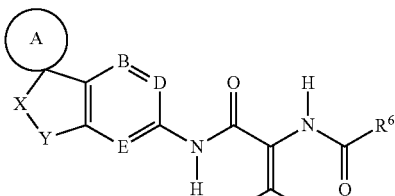

(IF)

wherein

A, B, D, E, X, Y and $R^6$ are as defined above;

$R^{5a}$ represents $C_{3-7}$ cycloalkyl, $C_{4-9}$ bicycloalkyl, aryl, $C_{3-7}$ heterocycloalkyl or heteroaryl, any of which groups may be optionally substituted by one or more substituents; and $R^{5b}$ represents hydrogen or $C_{1-6}$ alkyl; or $R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups may be optionally substituted by one or more substituents.

Typically, $R^5$ represents hydrogen; or $R^5$ represents $C_{1-5}$ alkyl, $C_{3-9}$ cycloalkyl, $C_{3-9}$ cycloalkyl($C_{1-5}$)alkyl, $C_{4-9}$ bicycloalkyl, $C_{4-9}$ bicycloalkyl($C_{1-5}$)alkyl, $C_{5-9}$ spiro-cycloalkyl, $C_{9-11}$ tricycloalkyl, $C_{9-11}$ tricycloalkyl($C_{1-5}$)alkyl, aryl, aryl (C-s)alkyl, $C_{3-7}$ heterocycloalkyl, $C_{3-7}$ heterocycloalkyl($C_{1-5}$)alkyl or heteroaryl($C_{1-5}$)alkyl, any of which groups may be optionally substituted by one or more substituents.

Suitably, $R^5$ represents $C_{3-9}$ cycloalkyl, which group may be optionally substituted by one or more substituents.

In a first embodiment, $R^5$ represents hydrogen. In a second embodiment, $R^5$ represents optionally substituted $C_{1-5}$ alkyl. In a third embodiment, $R^5$ represents optionally substituted $C_{3-9}$ cycloalkyl. In a fourth embodiment, $R^5$ represents optionally substituted $C_{3-9}$ cycloalkyl($C_{1-5}$)alkyl. In a fifth embodiment, $R^5$ represents optionally substituted $C_{4-9}$ bicycloalkyl. In a sixth embodiment, $R^5$ represents optionally substituted $C_{4-9}$ bicycloalkyl($C_{1-5}$)alkyl. In a seventh embodiment, $R^5$ represents optionally substituted $C_{5-9}$ spirocycloalkyl. In an eighth embodiment, $R^5$ represents optionally substituted $C_{5-9}$ spirocycloalkyl($C_{1-5}$)alkyl. In a ninth embodiment, $R^5$ represents optionally substituted $C_{9-11}$ tricycloalkyl. In a tenth embodiment, $R^5$ represents optionally substituted $C_{9-11}$ tricycloalkyl($C_{1-5}$)alkyl. In an eleventh embodiment, $R^5$ represents optionally substituted aryl. In a twelfth embodiment, $R^5$ represents optionally substituted aryl($C_{1-5}$)alkyl. In a thirteenth embodiment, $R^5$ represents optionally substituted $C_{3-7}$ heterocycloalkyl. In a fourteenth embodiment, $R^5$ represents optionally substituted $C_{3-7}$ heterocycloalkyl($C_{1-5}$)alkyl. In a fifteenth embodiment, $R^5$ represents optionally substituted heteroaryl. In a sixteenth embodiment, $R^5$ represents optionally substituted heteroaryl($C_{1-5}$)alkyl.

In a particular embodiment, $R^5$ is other than hydrogen.

Typical values of $R^5$ include methyl, cyclobutyl, benzocyclobutenyl, cyclopentyl, indanyl, cyclohexyl, tetrahydronaphthalenyl, cycloheptyl, benzocycloheptenyl, cyclooctyl, cyclononanyl, cyclobutylmethyl, cyclobutylethyl, bicyclo[3.1.0]hexanyl, bicyclo[2.2.1]-heptanyl, bicyclo [3.3.0]octanyl, bicyclo[3.2.1]octanyl, bicyclo[1.1.1]pentanylmethyl, spiro[3.3]heptanyl, adamantanyl, adamantanylmethyl, phenyl, benzyl, phenylethyl, phenylpropyl, tetrahydropyranyl, azocanyl, dihydrobenzofuranylmethyl and pyrrolylethyl, any of which groups may be optionally substituted by one or more substituents.

Suitable values of $R^5$ include cyclohexyl and cyclooctyl, either of which groups may be optionally substituted by one or more substituents.

Typical examples of optional substituents on $R^5$ include one, two or three substituents independently selected from halogen, cyano, nitro, $C_{1-6}$ alkyl, trifluoro-methyl, trifluoroethyl, phenyl, hydroxy, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkyl-sulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylamino-sulfonyl and di($C_{1-6}$)alkylaminosulfonyl.

Suitable examples of optional substituents on $R^5$ include one, two or three substituents independently selected from halogen, cyano, $C_{1-6}$ alkyl, trifluoromethyl, phenyl, hydroxy, $C_{1-6}$ alkoxy and aminocarbonyl, especially $C_{1-6}$ alkyl.

Typical examples of specific substituents on $R^5$ include one, two or three substituents independently selected from fluoro, chloro, bromo, cyano, nitro, methyl, ethyl, isopropyl, tert-butyl, trifluoromethyl, trifluoroethyl, phenyl, hydroxy, oxo, methoxy, isopropoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl and dimethyl-aminosulfonyl.

Suitable examples of specific substituents on $R^5$ include one, two or three substituents independently selected from fluoro, chloro, bromo, cyano, methyl, trifluoro-methyl, phenyl, hydroxy, methoxy, isopropoxy, tert-butoxy and aminocarbonyl, especially methyl.

Apposite values of $R^5$ include hydrogen, tert-butoxymethylcyclobutyl, methyl-cyclobutyl, dimethylcyclobutyl, phenylcyclobutyl, benzocyclobutenyl, cyclopentyl, methylcyclopentyl, indanyl, cyclohexyl, difluorocyclohexyl, methylcyclohexyl, dimethylcyclohexyl, trifluoromethylcyclohexyl, tetrahydronaphthalenyl, cycloheptyl, benzocycloheptenyl, cyclooctyl, cyclononanyl, cyclobutylmethyl, difluorocyclobutyl-methyl, dimethylcyclobutylmethyl, cyclobutylethyl, bicyclo[3.1.0]hexanyl, bicyclo[2.2.1]-heptanyl, bicyclo[3.3.0]octanyl, bicyclo[3.2.1]octanyl, bicyclo[1.1.1]pentanylmethyl, spiro[3.3]heptanyl, adamantanyl, adamantanylmethyl, (chloro)(fluoro)phenyl, (fluoro)-(methyl)phenyl, fluorobenzyl, chlorobenzyl, (chloro)(fluoro)benzyl, (bromo)(chloro)-benzyl, (chloro)(isopropoxy)benzyl, phenylethyl, chlorophenylethyl, phenylpropyl, tetrahydropyranyl, tetramethyltetrahydropyranyl, azocanyl, dihydrobenzofuranylmethyl and methylpyrrolylethyl.

Favoured values of $R^5$ include 4-methylcyclohexyl and cyclooctyl. In a first embodiment, $R^5$ represents 4-methylcyclohexyl. In a second embodiment, $R^5$ represents cyclooctyl.

In a first embodiment, $R^{5a}$ represents optionally substituted $C_{3-7}$ cycloalkyl. In a second embodiment, $R^{5a}$ represents optionally substituted $C_{4-9}$ bicycloalkyl. In a third embodiment, $R^{5a}$ represents optionally substituted aryl. In a fourth embodiment, $R^{5a}$ represents optionally substituted $C_{3-7}$ heterocycloalkyl. In a fifth embodiment, $R^{5a}$ represents optionally substituted heteroaryl.

Typical values of $R^{5a}$ include cyclobutyl, cyclopentyl, bicyclo[1.1.1]pentanyl, phenyl, dihydrobenzofuranyl and pyrrolyl, any of which groups may be optionally substituted by one or more substituents.

Typical examples of optional substituents on $R^{5a}$ include $C_{1-6}$ alkyl, halogen, cyano, trifluoromethyl, trifluoroethyl, phenyl, hydroxy, $C_{1-6}$ alkoxy, $C_{1-6}$ alkylthio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkyl-amino.

Suitable examples of optional substituents on $R^{5a}$ include $C_{1-6}$ alkyl and halogen.

Typical examples of particular substituents on $R^{5a}$ include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Suitable examples of particular substituents on $R^{5a}$ include methyl and chloro.

Suitable values of $R^{5a}$ include cyclobutyl, cyclopentyl, bicyclo[1.1.1]pentanyl, phenyl, chlorophenyl, dihydrobenzofuranyl and methylpyrrolyl.

Suitably, $R^{5b}$ represents hydrogen, methyl or ethyl.

In a first embodiment, $R^{5b}$ represents hydrogen. In a second embodiment, $R^{5b}$ represents $C_{1-6}$ alkyl, especially methyl or ethyl.

Alternatively, $R^{5a}$ and $R^{5b}$, when taken together with the carbon atom to which they are both attached, may represent $C_{3-7}$ cycloalkyl, $C_{4-9}$ bicycloalkyl or $C_{3-7}$ hetero-cycloalkyl, any of which groups may be unsubstituted, or substituted by one or more substituents, typically by one or two substituents.

In a first embodiment, $R^{5a}$ and $R^{5b}$, when taken together with the carbon atom to which they are both attached, may suitably represent optionally substituted $C_{3-7}$ cycloalkyl. Examples include cyclobutyl, benzocyclobutenyl, cyclopentyl, indanyl, cyclohexyl, tetrahydronaphthalenyl, cycloheptanyl, benzocycloheptenyl, cyclooctanyl and cyclononanyl, any of which groups may be optionally substituted by one or more substituents.

In a second embodiment, $R^{5a}$ and $R^{5b}$, when taken together with the carbon atom to which they are both attached, may suitably represent optionally substituted $C_{4-9}$ bicycloalkyl. Examples include bicyclo[3.1.0]hexanyl, bicyclo[2.2.1]heptanyl and bicyclo[3.2.1]octanyl, any of which groups may be optionally substituted by one or more substituents.

In a third embodiment, $R^{5a}$ and $R^{5b}$, when taken together with the carbon atom to which they are both attached, may suitably represent optionally substituted $C_{3-7}$ hetero-cycloalkyl. Examples include tetrahydropyranyl and piperidinyl, either of which groups may be optionally substituted by one or more substituents.

Typical examples of optional substituents on such groups include $C_{1-6}$ alkyl, halogen, cyano, trifluoromethyl, trifluoroethyl, phenyl, hydroxy, $C_{1-6}$ alkoxy, $C_{1-6}$ alkyl-thio, $C_{1-6}$ alkylsulfinyl, $C_{1-6}$ alkylsulfonyl, $C_{2-6}$ alkylcarbonyl, amino, $C_{1-6}$ alkylamino and di($C_{1-6}$)alkylamino.

Suitable examples of optional substituents on such groups include $C_{1-6}$ alkyl, halogen, trifluoromethyl, trifluoroethyl, phenyl and $C_{1-6}$ alkoxy, especially halogen.

Typical examples of particular substituents on such groups include methyl, fluoro, chloro, bromo, cyano, trifluoromethyl, trifluoroethyl, phenyl, hydroxy, methoxy, methylthio, methylsulfinyl, methylsulfonyl, acetyl, amino, methylamino and dimethylamino.

Suitable examples of particular substituents on such groups include methyl, chloro, trifluoromethyl, trifluoroethyl, phenyl and methoxy, especially chloro.

Typical values of $R^{5a}$ and $R^{5b}$, when taken together with the carbon atom to which they are both attached, include methylcyclobutyl, dimethylcyclobutyl, phenylcyclobutyl, benzocyclobutenyl, methylbenzocyclobutenyl, chlorobenzocyclobutenyl, methoxy-benzocyclobutenyl, cyclopentyl, methylcyclopentyl, indanyl, chloroindanyl, cyclohexyl, methylcyclohexyl, dimethylcyclohexyl, trifluoromethylcyclohexyl, tetrahydro-naphthalenyl, cycloheptanyl, benzocycloheptenyl, cyclooctanyl, cyclononanyl, bicyclo[3.1.0]hexanyl, bicyclo[2.2.1]heptanyl, bicyclo[3.2.1]octanyl, tetramethyl-tetrahydropyranyl and trifluoroethylpiperidinyl.

Suitable values of $R^{5a}$ and $R^{5b}$, when taken together with the carbon atom to which they are both attached, include chlorobenzocyclobutenyl.

Typically, $R^6$ represents —$NR^{6a}R^{6b}$ or —$OR^e$; or $R^6$ represents $C_{1-9}$ alkyl, aryl, $C_{3-7}$ heterocycloalkyl, heteroaryl, heteroaryl($C_{1-6}$)alkyl or spiro[($C_{3-7}$)heterocycloalkyl]-[heteroaryl], any of which groups may be optionally substituted by one or more substituents.

Appositely, $R^6$ represents aryl or heteroaryl, either of which groups may be optionally substituted by one or more substituents.

Suitably, $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl$(C_{1-6})$alkyl. In a fourth embodiment, $R^6$ represents optionally substituted aryl. In a fifth embodiment, $R^6$ represents optionally substituted aryl$(C_{1-6})$alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl$(C_{1-6})$alkyl. In an eighth embodiment, $R^6$ represents optionally substituted heteroaryl. In a ninth embodiment, $R^6$ represents optionally substituted heteroaryl$(C_{1-6})$alkyl. In a tenth embodiment, $R^6$ represents optionally substituted spiro[$(C_{3-7})$heterocycloalkyl][heteroaryl]. In an eleventh embodiment, $R^6$ represents —$NR^{6a}R^{6b}$. In a twelfth embodiment, $R^6$ represents —$OR^{6c}$.

Typical values of $R^6$ include —$NR^{6a}R^{6b}$ and —$OR^{6c}$; and methyl, tert-butyl, heptanyl, phenyl, pyrrolidinyl, indolinyl, piperidinyl, morpholinyl, thiomorpholinyl, piperazinyl, pyrrolyl, pyrazolyl, pyrazolo[1,5-a]pyridinyl, 4,5,6,7-tetrahydropyrazolyl, oxazolyl, isoxazolyl, thiazolyl, isothiazolyl, imidazolyl, oxadiazolyl, thiadiazolyl, triazolyl, tetrazolyl, pyridinyl, pyridazinyl, pyrimidinyl, pyridinylmethyl or spiro[tetrahydrofuran]-[indole], any of which groups may be optionally substituted by one or more substituents.

Apposite values of $R^6$ include phenyl, pyrazolyl, isoxazolyl and oxadiazolyl, any of which groups may be optionally substituted by one or more substituents.

Suitable values of $R^6$ include pyrazolyl and isoxazolyl, either of which groups may be optionally substituted by one or more substituents.

Typical examples of optional substituents on $R^6$ include one, two or three substituents independently selected from halogen, cyano, nitro, $C_{1-6}$ alkyl, difluoromethyl, trifluoromethyl, difluoroethyl, trifluoroethyl, trifluoropropyl, cyclopropyl, cyclobutyl, cyclopropylmethyl, phenyl, fluorophenyl, hydroxy, hydroxy$(C_{1-6})$alkyl, oxo, $C_{1-6}$ alkoxy, $C_{1-6}$ alkoxy$(C_{1-6})$alkyl, difluoromethoxy, trifluoromethoxy, $C_{1-6}$ alkylthio, $C_{1-6}$ alkyl-sulfinyl, $C_{1-6}$ alkylsulfonyl, $C_{1-6}$ alkylsulfonyloxy, amino, amino$(C_{1-6})$alkyl, $C_{1-6}$ alkyl-amino, di$(C_{1-6})$alkylamino, di$(C_{1-6})$alkylamino$(C_{1-6})$alkyl, pyrrolidinyl, tetrahydropyranyl, morpholinyl, piperazinyl, $C_{2-6}$ alkylcarbonylamino, $C_{2-6}$ alkylcarbonylamino$(C_{1-6})$alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di$(C_{1-6})$alkylamino-carbonyl, aminosulfonyl, $C_{1-6}$ alkylaminosulfonyl, di$(C_{1-6})$alkylaminosulfonyl and di$(C_{1-6})$alkylsulfoximinyl. Additional examples include $(C_{1-6})$alkylsulfonyl$(C_{1-6})$alkyl and dioxoisothiazolidinyl.

Apposite examples of optional substituents on $R^6$ include one, two or three substituents independently selected from $C_{1-6}$ alkyl, $(C_{1-6})$alkylsulfonyl$(C_{1-6})$alkyl, dioxoisothiazolidinyl, tetrahydropyranyl, $C_{1-6}$ alkylsulfonylamino and di$(C_{1-6})$alkyl-sulfoximinyl.

Suitable examples of optional substituents on $R^6$ include one, two or three substituents independently selected from $C_{1-6}$ alkyl.

Typical examples of specific substituents on $R^6$ include one, two or three substituents independently selected from fluoro, chloro, bromo, cyano, nitro, methyl, ethyl, n-propyl, isopropyl, 2-methylpropyl, butan-2-yl, tert-butyl, difluoromethyl, trifluoromethyl, difluoroethyl, trifluoroethyl, trifluoropropyl, cyclopropyl, cyclobutyl, cyclopropylmethyl, phenyl, fluorophenyl, hydroxy, hydroxymethyl, hydroxyethyl, oxo, methoxy, tert-butoxy, methoxymethyl, methoxyethyl, difluoromethoxy, trifluoromethoxy, methylthio, methylsulfinyl, methylsulfonyl, methylsulfonyloxy, amino, aminomethyl, aminoethyl, aminoisopropyl, methylamino, tert-butylamino, dimethylamino, dimethyl-aminoethyl, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl, dimethylamino-sulfonyl and dimethylsulfoximinyl. Additional examples include methylsulfonylmethyl and dioxoisothiazolidinyl.

Apposite examples of specific substituents on $R^6$ include one, two or three substituents independently selected from methyl, ethyl, isopropyl, methylsulfonylmethyl, dioxoisothiazolidinyl, tetrahydropyranyl, methylsulfonylamino and dimethylsulfoximinyl.

Suitable examples of specific substituents on $R^6$ include one, two or three substituents independently selected from methyl and ethyl.

Illustrative values of $R^6$ include —$NR^{6a}R^{6b}$, $OR^{6c}$, methyl, tert-butyl, hydroxyheptanyl, phenyl, fluorophenyl, methylsulfonylphenyl, pyrrolidinyl, methyl-pyrrolidinyl, indolinyl, piperidinyl, morpholinyl, dioxothiomorpholinyl, methyl-piperazinyl, methylpyrrolyl, methylpyrazolyl, dimethylpyrazolyl, ethylpyrazolyl, (ethyl)-(fluoro)pyrazolyl, (ethyl)(methyl)pyrazolyl, n-propylpyrazolyl, isopropylpyrazolyl, 2-methylpropylpyrazolyl, butan-2-ylpyrazolyl, difluoromethylpyrazolyl, (difluoromethyl)-(methyl)pyrazolyl, difluoroethylpyrazolyl, trifluoroethylpyrazolyl, trifluoropropyl-pyrazolyl, cyclopropylpyrazolyl, cyclobutylpyrazolyl, cyclopropylmethylpyrazolyl, hydroxyethylpyrazolyl, methoxyethylpyrazolyl, dimethylaminoethylpyrazolyl, tetrahydropyranylpyrazolyl, (methyl)(tetrahydropyranyl)pyrazolyl, pyrazolo[1,5-a]-pyridinyl, methyl-4,5,6,7-tetrahydropyrazolyl, oxazolyl, methyloxazolyl, ethyloxazolyl, isoxazolyl, methylisoxazolyl, dimethylisoxazolyl, ethylisoxazolyl, isopropylisoxazolyl, tert-butylisoxazolyl, trifluoromethylisoxazolyl, cyclopropylisoxazolyl, cyclobutylisoxazolyl, methoxymethylisoxazolyl, aminomethylisoxazolyl, aminoisopropylisoxazolyl, thiazolyl, methylthiazolyl, dimethylthiazolyl, isothiazolyl, methylisothiazolyl, methyl-imidazolyl, methyloxadiazolyl, methylthiadiazolyl, methyltriazolyl, dimethyltriazolyl, ethyltriazolyl, methyltetrazolyl, pyridinyl, methylpyridinyl, pyridazinyl, pyrimidinyl, methylpyrimidinyl, pyridinylmethyl, aminopyridinylmethyl and spiro[tetrahydrofuran]-[oxoindole]. Additional values include methylsulfonylmethylphenyl, dioxo-isothiazolidinylphenyl, methylsulfonylaminophenyl, dimethylsulfoximinylphenyl and ethyloxadiazolyl.

Apposite values of $R^6$ include methylsulfonylmethylphenyl, dioxoisothiazolidinyl-phenyl, methylsulfonylaminophenyl, dimethylsulfoximinylphenyl, ethylpyrazolyl, isopropylpyrazolyl, tetrahydropyranylpyrazolyl, methylisoxazolyl and ethyloxadiazolyl.

Representative values of $R^6$ include ethylpyrazolyl and methylisoxazolyl.

Typically, $R^{6a}$ represents $C_{1-6}$ alkyl, $C_{3-7}$ cycloalkyl, aryl$(C_{1-6})$alkyl, $C_{3-7}$ heterocycloalkyl or spiro[$(C_{3-7})$heterocycloalkyl][heteroaryl], any of which groups may be optionally substituted by one or more substituents.

In a first embodiment, $R^{6a}$ represents hydrogen. In a second embodiment, $R^{6a}$ represents optionally substituted $C_{1-6}$ alkyl. In a first aspect of that embodiment, $R^{6a}$ represents represents unsubstituted $C_{1-6}$ alkyl, especially methyl. In a second aspect of that embodiment, $R^{6a}$ represents represents monosubstituted, disubstituted or trisubstituted $C_{1-6}$ alkyl. In a third embodiment, $R^{6a}$ represents optionally substituted $C_{3-7}$ cycloalkyl. In a fourth embodiment, $R^{6a}$ represents optionally substituted $C_{3-7}$ cycloalkyl($C_{1-6}$)alkyl. In a fifth embodiment, $R^{6a}$ represents optionally substituted aryl. In a sixth embodiment, $R^{6a}$ represents optionally substituted aryl($C_{1-6}$)alkyl. In a seventh embodiment, $R^{6a}$ represents optionally substituted $C_{3-7}$ heterocycloalkyl. In an eighth embodiment, $R^{6a}$ represents optionally substituted $C_{3-7}$ heterocycloalkyl($C_{1-6}$)alkyl. In a ninth embodiment, $R^{6a}$ represents optionally substituted heteroaryl. In a tenth embodiment, $R^{6a}$ represents optionally substituted heteroaryl($C_{1-6}$)alkyl. In an eleventh embodiment, $R^{6a}$ represents optionally substituted spiro[($C_{3-7}$)heterocycloalkyl][heteroaryl].

Typical values of $R^{6a}$ include methyl, ethyl, n-propyl, isopropyl, 2,2-dimethyl-propyl, cyclohexyl, benzyl, tetrahydrofuranyl, tetrahydropyranyl, tetrahydrothiopyranyl and spiro[tetrahydrofuran][indole], any of which groups may be optionally substituted by one or more substituents.

Typical examples of optional substituents on $R^{6a}$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^{6a}$ include one, two or three substituents independently selected from trifluoromethyl, oxo and $C_{1-6}$ alkoxy.

Typical examples of specific substituents on $R^{6a}$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetyl-amino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methyl-aminocarbonyl, dimethylaminocarbonyl, aminosulfonyl, methylaminosulfonyl and dimethylaminosulfonyl.

Selected examples of specific substituents on $R^{6a}$ include one, two or three substituents independently selected from trifluoromethyl, oxo and methoxy.

Selected values of $R^{6a}$ include methyl, ethyl, trifluoroethyl, methoxyethyl, n-propyl, isopropyl, 2,2-dimethylpropyl, cyclohexyl, benzyl, tetrahydrofuranyl, tetrahydropyranyl, oxotetrahydrothiopyranyl and spiro[tetrahydrofuran][oxoindole].

Suitably, $R^{6b}$ represents hydrogen, methyl, ethyl, n-propyl or isopropyl.

Typically, $R^{6b}$ represents hydrogen or methyl.

In a first embodiment, $R^{6b}$ represents hydrogen. In a second embodiment, $R^{6b}$ represents $C_{1-6}$ alkyl. In a particular aspect of that embodiment, $R^{6b}$ represents methyl, ethyl, n-propyl or isopropyl, especially methyl.

Typically, $R^{6c}$ represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl or heteroaryl($C_{1-6}$)alkyl, any of which groups may be optionally substituted by one or more substituents.

In a first embodiment, $R^{6c}$ represents optionally substituted $C_{1-6}$ alkyl. In a second embodiment, $R^{6c}$ represents optionally substituted $C_{3-7}$ cycloalkyl. In a third embodiment, $R^{6c}$ represents optionally substituted $C_{3-7}$ cycloalkyl($C_{1-6}$)alkyl. In a fourth embodiment, $R^{6c}$ represents optionally substituted aryl. In a fifth embodiment, $R^{6c}$ represents optionally substituted aryl($C_{1-6}$)alkyl. In a sixth embodiment, $R^{6c}$ represents optionally substituted $C_{3-7}$ heterocycloalkyl. In a seventh embodiment, $R^{6c}$ represents optionally substituted $C_{3-7}$ heterocycloalkyl($C_{1-6}$)alkyl. In an eighth embodiment, $R^{6c}$ represents optionally substituted heteroaryl. In a ninth embodiment, $R^{6c}$ represents optionally substituted heteroaryl($C_{1-6}$)alkyl.

Typical values of $R^{6c}$ include methyl, ethyl, isopropyl, 2-methylpropyl, tert-butyl, 2,2-dimethylpropyl, cyclobutyl, cyclopentyl, cyclohexyl, cyclopropylmethyl, cyclohexylmethyl, oxetanyl, azetidinyl, tetrahydrofuranyl, tetrahydropyranyl, tetrahydropyranyl-methyl, pyrazolylmethyl, oxazolylmethyl, isoxazolylmethyl, imidazolylmethyl and pyrazinylmethyl, any of which groups may be optionally substituted by one or more substituents.

Typical examples of optional substituents on $R^{6c}$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6c}$ include one, two or three substituents independently selected from $C_{1-6}$ alkyl, trifluoromethyl, $C_{1-6}$ alkoxy and $C_{2-6}$ alkoxycarbonyl.

Typical examples of specific substituents on $R^{6c}$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetyl-amino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methyl-aminocarbonyl, dimethylaminocarbonyl, aminosulfonyl, methylaminosulfonyl and dimethylaminosulfonyl.

Suitable examples of specific substituents on $R^{6c}$ include one, two or three substituents independently selected from methyl, trifluoromethyl, methoxy and tert-butoxycarbonyl.

Typical values of $R^{6c}$ include methyl, trifluoroethyl, methoxyethyl, isopropyl, 2-methylpropyl, tert-butyl, 2,2-dimethylpropyl, cyclobutyl, cyclopentyl, cyclohexyl, cyclopropylmethyl, cyclohexylmethyl, oxetanyl, methyloxetanyl, azetidinyl, tert-butoxycarbonylazetidinyl, tetrahydrofuranyl, tetrahydropyranyl, tetrahydropyranylmethyl, methylpyrazolylmethyl, oxazolylmethyl, isoxazolylmethyl, methylimidazolylmethyl and pyrazinylmethyl.

In a first embodiment, $R^7$ represents aryl, which group may be optionally substituted by one or more substituents. In a second embodiment, $R^7$ represents heteroaryl, which group may be optionally substituted by one or more substituents. In a third embodiment, $R^7$ represents spiro[($C_{3-7}$)heterocycloalkyl][heteroaryl], which group may be optionally substituted by one or more substituents.

Typical values of $R^7$ include phenyl, pyrazolo[1,5-a]pyrazinyl, benzoxazolyl, benzothiazolyl, benzimidazolyl, imidazo[1,2-b]pyridazinyl, purinyl, pyridinyl, pyridazinyl, cinnolinyl, pyrimidinyl, pyrazinyl and spiro[tetrahydropyranyl][indole], any of which groups may be optionally substituted by one or more substituents.

Typical examples of optional substituents on $R^7$ include one, two or three substituents independently selected from halogen, cyano, nitro, $C_{1-6}$ alkyl, difluoromethyl, trifluoromethyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, pyrrolidinyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^7$ include one, two or three substituents independently selected from halogen, cyano, $C_{1-6}$ alkyl, difluoromethyl, trifluoromethyl, oxo, $C_{1-6}$ alkoxy, difluoromethoxy and di($C_{1-6}$)alkylamino.

Typical examples of specific substituents on $R^7$ include one, two or three substituents independently selected from fluoro, chloro, bromo, cyano, nitro, methyl, ethyl, isopropyl, tert-butyl, difluoromethyl, trifluoromethyl, phenyl, fluorophenyl, hydroxy, hydroxymethyl, oxo, methoxy, isopropoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, morpholinyl, piperazinyl, acetylamino, acetylaminoethyl, methoxycarbonylamino, methylsulfonyl-amino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^7$ include one, two or three substituents independently selected from fluoro, chloro, cyano, methyl, ethyl, isopropyl, difluoromethyl, trifluoromethyl, oxo, methoxy, isopropoxy, difluoromethoxy and dimethylamino.

Selected values of $R^7$ include phenyl, pyrazolo[1,5-a]pyrazinyl, benzoxazolyl, fluorobenzoxazolyl, methylbenzoxazolyl, benzothiazolyl, benzimidazolyl, fluoro-benzimidazolyl, imidazo[1,2-b]pyridazinyl, purinyl, pyridinyl, cyanopyridinyl, methyl-pyridinyl, methoxypyridinyl, pyridazinyl, chloropyridazinyl, cyanopyridazinyl, methylpyridazinyl, ethylpyridazinyl, isopropylpyridazinyl, difluoromethylpyridazinyl, trifluoro-methylpyridazinyl, methoxypyridazinyl, isopropoxypyridazinyl, difluoromethoxypyridazinyl, dimethylaminopyridazinyl, cinnolinyl, pyrimidinyl, pyrazinyl, methyl-pyrazinyl and spiro[tetrahydropyranyl][oxoindole].

Typically, $X^1$ represents hydrogen, halogen or $C_{1-6}$ alkyl.
Suitably, $X^1$ represents hydrogen or halogen.
In a first embodiment, $X^1$ represents hydrogen. In a second embodiment, $X^1$ represents halogen. In a first aspect of that embodiment, $X^1$ represents fluoro. In a second aspect of that embodiment, $X^1$ represents chloro. In a third embodiment, $X^1$ represents $C_{1-6}$ alkyl, especially methyl.
Typical values of $X^1$ include hydrogen, fluoro, chloro and methyl.
Suitable values of $X^1$ include hydrogen and fluoro.
In a first embodiment, $X^2$ represents hydrogen. In a second embodiment, $X^2$ represents halogen. In a first aspect of that embodiment, $X^2$ represents fluoro. In a second aspect of that embodiment, $X^2$ represents chloro. In a third embodiment, $X^2$ represents $C_{1-6}$ alkyl, especially methyl.
Typically, $X^3$ represents hydrogen or methyl.
In a first embodiment, $X^3$ represents hydrogen. In a second embodiment, $X^3$ represents $C_{1-6}$ alkyl, especially methyl.
Typically, $X^4$ represents hydrogen or methyl.
In a first embodiment, $X^4$ represents hydrogen. In a second embodiment, $X^4$ represents $C_{1-6}$ alkyl, especially methyl.
Typically, $Y^1$ represents hydrogen, halogen or $C_{1-6}$ alkyl.
Suitably, $Y^1$ represents hydrogen or halogen.
In a first embodiment, $Y^1$ represents hydrogen. In a second embodiment, $Y^1$ represents halogen. In a first aspect of that embodiment, $Y^1$ represents fluoro. In a second aspect of that embodiment, $Y^1$ represents chloro. In a third embodiment, $Y^1$ represents $C_{1-6}$ alkyl, especially methyl.
Typical values of $Y^1$ include hydrogen, fluoro, chloro and methyl.
Suitable values of $Y^1$ include hydrogen and fluoro.
In a first embodiment, $Y^2$ represents hydrogen. In a second embodiment, $Y^2$ represents halogen. In a first aspect of that embodiment, $Y^2$ represents fluoro. In a second aspect of that embodiment, $Y^2$ represents chloro. In a third embodiment, $Y^2$ represents $C_{1-6}$ alkyl, especially methyl.
Typically, $Y^3$ represents hydrogen or methyl.
In a first embodiment, $Y^3$ represents hydrogen. In a second embodiment, $Y^3$ represents $C_{1-6}$ alkyl, especially methyl.
Typically, $Y^4$ represents hydrogen or methyl.
In a first embodiment, $Y^4$ represents hydrogen. In a second embodiment, $Y^4$ represents $C_{1-6}$ alkyl, especially methyl.

One sub-class of the compounds of formula (IA) above is represented by the compounds of formula (IIA), and pharmaceutically acceptable salts thereof:

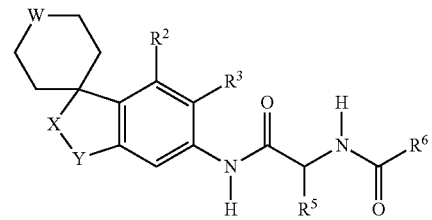

(IIA)

wherein
W represents O, S, S(O), S(O)$_2$, S(O)(NH) or N—R$^{17}$;
R$^{17}$ represents hydrogen or $C_{1-6}$ alkyl; and
X, Y, R$^2$, R$^3$, R$^5$ and R$^6$ are as defined above.
Typically, W represents O, S, S(O), S(O)$_2$ or N—R$^{17}$.

Suitably, W represents O, S or N—$R^{17}$.

In a first embodiment, W represents O. In a second embodiment, W represents S. In a third embodiment, W represents S(O). In a fourth embodiment, W represents $S(O)_2$. In a fifth embodiment, W represents S(O)(NH). In a sixth embodiment, W represents N—$R^{17}$.

Suitably, $R^{17}$ represents hydrogen or methyl.

In a first embodiment, $R^{17}$ represents hydrogen. In a second embodiment, $R^{17}$ represents $C_{1-6}$ alkyl. In a first aspect of that embodiment, $R^{17}$ represents methyl.

Another sub-class of the compounds of formula (IA) above is represented by the compounds of formula (IIB), and pharmaceutically acceptable salts thereof:

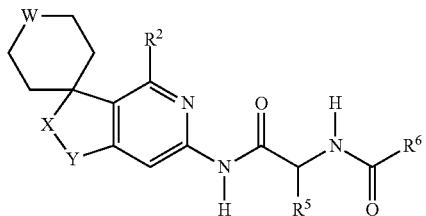

(IIB)

wherein W, X, Y, $R^2$, $R^5$ and $R^6$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases (including Crohn's disease and ulcerative colitis), ankylosing spondylitis and other spondylo-arthropathies, cancer and pain (particularly pain associated with inflammation).

Suitably, the compounds of the present invention are useful in the treatment and/or prophylaxis of psoriasis, psoriatic arthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above wherein $R^1$ represents —$COR^a$ may be prepared by a process which comprises reacting a carboxylic acid of formula $R^aCO_2H$, or a salt thereof, e.g. a lithium salt thereof, with a compound of formula (III):

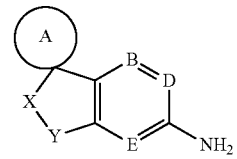

(III)

wherein A, B, D, E, X, Y and $R^a$ are as defined above.

The reaction is conveniently accomplished in the presence of a coupling agent.

Suitable coupling agents include 2-(7-aza-1H-benzotriazol-1-yl)-1,1,3,3-tetramethyluronium hexafluorophosphate (HATU), in which case the reaction may generally be carried out in the presence of a base which may suitably include organic amines, e.g. a trialkylamine such as N,N-diisopropylethylamine or triethylamine. The reaction is conveniently performed at ambient temperature in a suitable solvent, e.g. a chlorinated solvent such as dichloromethane, or a dipolar aprotic solvent such as N,N-dimethylformamide.

Alternatively, the coupling agent may be 2,4,6-tripropyl-1,3,5,2,4,6-trioxa-triphosphorinane 2,4,6-trioxide (propylphosphonic anhydride), in which case the reaction may generally be carried out in the presence of a base which may suitably include organic amines, e.g. a trialkylamine such as triethylamine or N,N-diisopropylethylamine, or an aromatic base such as pyridine. The reaction is conveniently performed at ambient or elevated temperature in a suitable solvent, e.g. an organic ester such as ethyl acetate, typically in admixture with a cyclic ether such as tetrahydrofuran, or a chlorinated solvent such as dichloromethane.

Alternatively, the coupling agent may be N-(3-dimethylaminopropyl)-N'-ethyl-carbodiimide hydrochloride, in which case the reaction may generally be carried out in the presence of an acid, e.g. an organic acid such as acetic acid. The reaction is conveniently performed at an elevated temperature in a suitable solvent, e.g. a cyclic ether such as tetrahydrofuran.

Where $R^a$ represents —$CH(R^5)N(H)C(O)R^6$, the intermediates of formula $R^aCO_2H$ may be prepared by a two-step procedure which comprises: (i) reacting a carboxylic acid of formula $R^6$—$CO_2H$ with a compound of formula (IV):

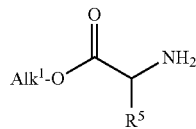
(IV)

wherein $Alk^1$ represents CIA alkyl, e.g. methyl, and $R^5$ and $R^6$ are as defined above; under conditions analogous to those described above for the reaction between compound (III) and a carboxylic acid of formula $R^aCO_2H$; and (ii) saponification of the resulting material by treatment with a base.

As for the reaction between compound (III) and a carboxylic acid of formula $R^aCO_2H$, the coupling agent employed in step (i) may suitably be HATU; or propylphosphonic anhydride; or N-(3-dimethylaminopropyl)-N'-ethylcarbodiimide hydrochloride.

Suitably, the coupling agent may be a mixture of N-(3-dimethylaminopropyl)-N'-ethylcarbodiimide hydrochloride and 1-hydroxybenzotriazole, in which case the reaction may generally be carried out in the presence of a base, e.g. an organic amine such as N,N-diisopropylethylamine. The reaction is conveniently performed at ambient temperature in a suitable solvent, e.g. a dipolar aprotic solvent such as N,N-dimethylformamide.

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula $R^aCO_2H$.

Step (ii) is conveniently effected at ambient temperature in water and a suitable organic solvent, e.g. a cyclic ether such as tetrahydrofuran, optionally in admixture with a $C_{1-4}$ alkanol such as methanol.

In another procedure, the compounds of formula (I) above wherein $R^1$ represents —$SO_2R^b$ may be prepared by a process which comprises reacting a compound of formula $R^bSO_2C_1$ with a compound of formula (III) as defined above.

The reaction is conveniently accomplished at ambient temperature in the presence of a base, e.g. an organic base such as triethylamine, in a suitable solvent, e.g. a chlorinated hydrocarbon solvent such as dichloromethane.

In another procedure, the compounds of formula (I) above wherein $R^1$ represents —$COR^a$ may be prepared by a process which comprises reacting an amide of formula $R^aCONH_2$ with a compound of formula (V):

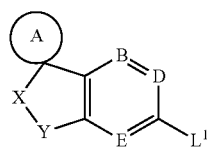
(V)

wherein A, B, D, E, X, Y and $R^a$ are as defined above, and $L^1$ represents a suitable leaving group; in the presence of a transition metal catalyst.

The leaving group $L^1$ is suitably a halogen atom, e.g. chloro or bromo.

The transition metal catalyst is suitably [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3), in which case the reaction will generally be performed in the presence of 2-(di-tert-butylphosphino)-2',4',6'-triisopropyl-3,6-dimethoxy-1,1'-biphenyl (tBuBrettPhos). The reaction is conveniently carried out at an elevated temperature in the presence of a base, e.g. an inorganic base such as potassium carbonate, in a suitable solvent, e.g. a lower alkanol such as tert-butanol.

Alternatively, the transition metal catalyst may suitably be tris(dibenzylidene-acetone)dipalladium(0), in which case the reaction will generally be performed in the presence of 2-dicyclohexylphosphino-2',4',6'-triisopropylbiphenyl (XPhos) or 4,5-bis(diphenylphosphino)-9,9-dimethylxanthene (Xantphos). The reaction is conveniently carried out at an elevated temperature in the presence of a base, e.g. a carbonate salt such as potassium carbonate or cesium carbonate, in a suitable solvent, e.g. a cyclic ether such as 1,4-dioxane, or a $C_{1-6}$ alkanol such as tert-butanol.

In another procedure, the compounds of formula (I) above wherein $R^1$ is an aryl or heteroaryl moiety may be prepared by a process which comprises reacting a compound of formula $R^1$—$NH_2$ with a compound of formula (V) as defined above; in the presence of a transition metal catalyst.

The transition metal catalyst is suitably tris(dibenzylideneacetone)dipalladium(0), in which case the reaction will generally be performed in the presence of 2-(di-tert-butyl)-phosphino-2',4',6'-triisopropylbiphenyl (tert-BuXPhos). The reaction is conveniently carried out at an elevated temperature in the presence of a base, e.g. a tert-butoxide salt such as sodium tert-butoxide, in a suitable solvent, e.g. a cyclic ether such as 1,4-dioxane.

In another procedure, the compounds of formula (IA) above may be prepared by a process which comprises reacting a compound of formula (III) as defined above with a compound of formula (VI):

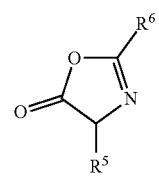
(VI)

wherein $R^5$ and $R^6$ are as defined above.

The reaction between compounds (III) and (VI) will generally be performed in the presence of acetic acid. The reaction is conveniently carried out at an elevated temperature in a suitable solvent, e.g. a cyclic ether such as tetrahydrofuran.

Similarly, the compounds of formula (IF) above may be prepared by a process which comprises reacting a compound of formula (III) as defined above with a compound of formula (VII):

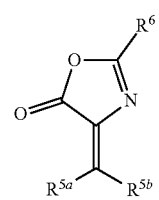
(VII)

wherein $R^{5a}$, $R^{5b}$ and $R^6$ are as defined above; under conditions analogous to those described above for the reaction between compounds (III) and (VI).

Where the respective values of $R^5$, $R^{5a}$ and $R^5$ permit, an intermediate of formula (VI) may be obtained from the corresponding intermediate of formula (VII) by conventional catalytic hydrogenation.

The intermediates of formula (VII) above may be prepared by reacting a compound of formula $R^{5a}C(O)R^{5b}$ with a compound of formula (VI) as defined above wherein $R^5$ represents hydrogen.

The reaction is conveniently effected by treating the reagents with titanium tetrachloride; followed by treatment of the resulting material with pyridine.

In another procedure, the compounds of formula (IA) above may be prepared by a process which comprises reacting a carboxylic acid of formula $R^6$—$CO_2H$ with a compound of formula (VIII):

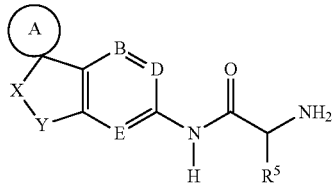

(VIII)

wherein A, B, D, E, X, Y, $R^5$ and $R^6$ are as defined above; under conditions analogous to those described above for the reaction between compound (III) and a carboxylic acid of formula $R^aCO_2H$.

Similarly, the compounds of formula (IA) above wherein $R^6$ represents —$NR^{6a}R^{6b}$ may be prepared by a process which comprises reacting a carbamate derivative of formula $L^2$-C(O)$NR^{6a}R^{6b}$, wherein $L^2$ represents a suitable leaving group, with a compound of formula (VIII) as defined above.

The leaving group $L^2$ is suitably a halogen atom, e.g. chloro; or $L^2$ is suitably phenoxy.

Where $L^2$ is a halogen atom, the reaction is conveniently carried out at ambient temperature in the presence of a base, e.g. an organic amine such as triethylamine, in a suitable solvent, e.g. a chlorinated solvent such as dichloromethane.

Where $L^2$ is phenoxy, the reaction is conveniently carried out at an elevated temperature in the presence of 4-(dimethylamino)pyridine, in a suitable solvent, e.g. a nitrile solvent such as acetonitrile.

Similarly, the compounds of formula (IA) above wherein $R^6$ represents —$OR^{6c}$ may be prepared by a process which comprises reacting a compound of formula L-C(O)$OR^6$, wherein $L^3$ represents a suitable leaving group, with a compound of formula (VIII) as defined above.

The leaving group $L^3$ is suitably a halogen atom, e.g. chloro.

The reaction is conveniently carried out at ambient temperature in the presence of a base, e.g. an organic amine such as triethylamine, typically in admixture with pyridine, in a suitable solvent, e.g. a cyclic ether such as tetrahydrofuran.

In another procedure, the compounds of formula (IB) above may be prepared by a process which comprises reacting a compound of formula (VIII) as defined above with a compound of formula $L^4$-S(O)$_2R^6$, wherein $R^6$ is as defined above, and $L^4$ represents a suitable leaving group.

The leaving group $L^4$ is suitably a halogen atom, e.g. chloro.

The reaction is conveniently carried out at ambient temperature in the presence of a base, e.g. an organic amine such as N,N-diisopropylethylamine, in a suitable solvent, e.g. a chlorinated solvent such as dichloromethane.

In another procedure, the compounds of formula (IC) above may be prepared by a process which comprises reacting a compound of formula (VIII) as defined above with a compound of formula $L^5$-$R^7$, wherein $R^7$ is as defined above, and $L^5$ represents a suitable leaving group.

The leaving group $L^5$ is suitably a halogen atom, e.g. chloro or bromo.

The reaction is conveniently carried out in the presence of a base. Suitable bases include organic amines, e.g. a trialkylamine such as N,N-diisopropylethylamine. The reaction is typically performed at an elevated temperature in a suitable solvent, e.g. a cyclic ether such as 1,4-dioxane.

Alternatively, the reaction may be performed in the presence of a transition metal catalyst. Suitable transition metal catalysts of use in this procedure include [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3). The reaction is conveniently carried out at an elevated temperature in the presence of a base, e.g. an inorganic base such as potassium tert-butoxide, in a suitable solvent or solvent mixture. The solvent or solvents may suitably be selected from a cyclic ether such as 1,4-dioxane, and a sulfoxide solvent such as dimethyl sulfoxide.

The intermediates of formula (VIII) above may be prepared by reacting a compound of formula (III) as defined above with a compound of formula (IX), or a salt thereof, e.g. a lithium salt thereof:

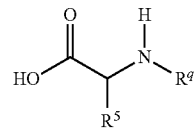

(IX)

wherein $R^5$ is as defined above, and $R^q$ represents hydrogen or an N-protecting group; under conditions analogous to those described above for the reaction between compound (III) and a carboxylic acid of formula $R^aCO_2H$; followed, as necessary, by removal of the N-protecting group $R^q$.

The N-protecting group $R^q$ may suitably be benzyloxycarbonyl. Alternatively, the N-protecting group $R^q$ may be tert-butoxycarbonyl (BOC).

Where the N-protecting group $R^q$ is benzyloxycarbonyl, the subsequent removal thereof may conveniently be effected by catalytic hydrogenation, typically by treatment with gaseous hydrogen in the presence of a hydrogenation catalyst, e.g. palladium on charcoal.

Where the N-protecting group $R^q$ is BOC, the subsequent removal thereof may conveniently be effected by treatment with an acid, e.g. a mineral acid such as hydrochloric acid, or an organic acid such as trifluoroacetic acid.

In another procedure, the compounds of formula (ID) above may be prepared by a process which comprises reacting a compound of formula $R^7$—$NH_2$ with a compound of formula (X):

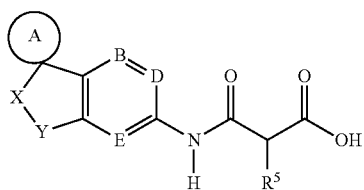

(X)

wherein A, B, D, E, X, Y, $R^5$ and $R^7$ are as defined above; under conditions analogous to those described above for the reaction between compound (III) and a carboxylic acid of formula $R^aCO_2H$.

The intermediates of formula (X) above may be prepared by a two-step procedure which comprises: (i) reacting a compound of formula (III) as defined above with a compound of formula (XI), or a salt thereof, e.g. a lithium salt thereof:

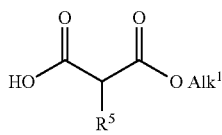

(XI)

wherein $R^5$ and $Alk^1$ are as defined above; under conditions analogous to those described above for the reaction between compound (III) and a carboxylic acid of formula $R^aCO_2H$; and (ii) saponification of the resulting material by treatment with a base.

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula (X).

Step (ii) is conveniently effected at ambient temperature in water and a suitable organic solvent, e.g. a $C_{1-4}$ alkanol such as ethanol.

Where —X—Y— in the desired compound of formula (I) contains an —NH— moiety, the relevant nitrogen atom in the intermediate of formula (III), (V), (VIII) or (X) above may be protected by an N-protecting group, which may subsequently be removed, once the compound of formula (III), (V), (VIII) or (X) has undergone the reaction or sequence of reactions indicated above, to provide the desired compound of formula (I). Suitable N-protecting groups include tert-butoxycarbonyl (BOC), benzyl, and 2-(trimethylsilyl)-ethoxymethyl (SEM).

Where the N-protecting group is BOC, the subsequent removal thereof may conveniently be effected by treatment with an acid, e.g. a mineral acid such as hydrochloric acid, or an organic acid such as trifluoroacetic acid.

Where the N-protecting group is benzyl, the subsequent removal thereof may conveniently be effected by catalytic hydrogenation, typically by treatment with gaseous hydrogen in the presence of a hydrogenation catalyst, e.g. palladium on charcoal.

Where the N-protecting group is SEM, the subsequent removal thereof may conveniently be effected by treatment with a fluoride salt, e.g. tetra-n-butylammonium fluoride; or by treatment with an acid, e.g. a mineral acid such as hydrochloric acid, or an organic acid such as trifluoroacetic acid.

Where they are not commercially available, the starting materials of formula (III), (IV), (V), (IX) and (XI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound of formula (I) comprising an amino (—$NH_2$) moiety may be acylated, e.g. acetylated, by treatment with a suitable acyl halide, e.g. acetyl chloride, typically in the presence of a base, e.g. an organic base such as N,N-diisopropylethylamine.

A compound which contains an N—H moiety may be alkylated, e.g. methylated, by treatment with the appropriate alkyl halide, e.g. iodomethane, typically at ambient temperature in the presence of a base, e.g. sodium hydride, in a suitable solvent, e.g. a dipolar aprotic solvent such as N,N-dimethylformamide.

A compound of formula (I) wherein $R^2$, $R^3$ or $R^4$ is hydrogen may be converted into the corresponding compound wherein $R^2$, $R^3$ or $R^4$ is fluoro by treatment with Selectfluor™.

A compound of formula (I) wherein $R^2$, $R^3$ or $R^4$ is hydrogen may be converted into the corresponding compound wherein $R^2$, $R^3$ or $R^4$ is chloro by treatment with N-chlorosuccinimide, typically in the presence of acetic acid.

Where the respective values of $R^5$, $R^{5a}$ and $R^{5b}$ permit, a compound of formula (IA) may be obtained from the corresponding compound of formula (IF) by conventional catalytic hydrogenation, e.g. by treatment with gaseous hydrogen in the presence of a hydrogenation catalyst such as palladium on charcoal.

A compound containing the moiety —S— may be converted into the corresponding compound containing the moiety —S(O)— by treatment with 3-chloroperoxybenzoic acid. Likewise, a compound containing the moiety —S— or —S(O)— may be converted into the corresponding compound containing the moiety —S(O)$_2$— by treatment with 3-chloroperoxy-benzoic acid.

A compound containing the moiety —S— may be converted into the corresponding compound containing the moiety —S(O)(NH)— by treatment with ammonium carbamate and (diacetoxyiodo)benzene.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P. G. M. Wuts, John Wiley & Sons, 5 edition, 2014. The protecting groups may be removed at any convenient subsequent stage utilising methods known from the art.

The compounds in accordance with this invention potently inhibit the ability of IL-17A to bind to IL-17RA. When tested in the IL-17 FRET assay described below, compounds of the present invention exhibit an $IC_{50}$ value of 10 µM or less, generally of 5 µM or less, usually of 1 µM or less, typically of 500 nM or less, suitably of 100 nM or less, ideally of 50 nM or less, and preferably of 25 nM or less (the skilled person will appreciate that a lower $IC_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit an $IC_{50}$ value of 10 µM or less, generally of 5 µM or less, usually of 1 µM or less, typically of 500 nM or less, suitably of 100 nM or less, ideally of 50 nM or less, and preferably of 25 nM or less (as before, the skilled person will appreciate that a lower $IC_{50}$ figure denotes a more active compound).

IL-17 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher #A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher #PV3581).

In assay buffer [Dulbecco's PBS (Sigma #14190-094), 0.05% P20 (Thermo Scientific #28320), 1 mg/mL BSA (Sigma #A2153-500G)] the following solutions were prepared:
For IL-17A Assay
  IL-17A-Fc-AF647 at 5 nM
  IL-17RA-HKH-Tb at 5 nM Compounds were serially diluted in DMSO before receiving an aqueous dilution into a 384 well dilution plate (Greiner #781281), to give a 25% DMSO solution.

IL-17A (10 µL) was added to a black low volume assay plate (Costar #4511) and diluted compound (5 µL) was transferred from the aqueous dilution plate. The cytokine and compound were allowed to incubate for 1 h, then IL-17RA (10 µL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay, the compounds of the accompanying Examples were all found to exhibit $IC_{50}$ values of 10 µM or better.

When tested in the IL-17 FRET assay, compounds of the accompanying Examples exhibit $IC_{50}$ values generally in the range of about 0.01 nM to about 10 µM, usually in the range of about 0.01 nM to about 5 µM, typically in the range of about 0.01 nM to about 1 µM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 µM) in combination with TNF-α (25 µM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125 \times 10^4$ cells/mL before being added to the 384 well assay plate (Corning #3701) at 40 µL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 μM/IL-17A 50 μM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for one hour at 37° C. After the incubation, 10 μL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the above assay, compounds of the accompanying Examples were found to exhibit $IC_{50}$ values of 10 μM or better.

When tested in the above assay, compounds of the accompanying Examples exhibit $IC_{50}$ values generally in the range of about 0.01 nM to about 10 μM, usually in the range of about 0.01 nM to about 5 μM, typically in the range of about 0.01 nM to about 1 μM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

The following Examples illustrate the preparation of compounds according to the invention.

EXAMPLES

Abbreviations

DCM: dichloromethane
MeOH: methanol
DMSO: dimethyl sulfoxide
EtOAc: ethyl acetate
EDC•HCl: N-(3-dimethylaminopropyl)-N'-ethylcarbodiimide hydrochloride
HATU: 2-(7-aza-1H-benzotriazol-1-yl)-1,1,3,3-tetramethyluronium hexafluorophosphate
$Pd_2(dba)_3$: tris(dibenzylideneacetone)dipalladium(0)
h: hour
M: mass
HPLC: High Performance Liquid Chromatography
LCMS: Liquid Chromatography Mass Spectrometry
ES+: Electrospray Positive Ionisation
PTFE: poly(tetrafluoroethylene)
DMF: A,A-dimethylformamide
THF: tetrahydro furan
DIPEA: A,A-diisopropylethylamine
HOBt: 1-hydroxybenzotriazole
r.t.: room temperature
RT: retention time Analytical Conditions Compounds were named with the aid of ACD/Name Batch (Network) version 11.01, and/or Accelrys Draw 4.2, and/or Elemental, Dotmatics, and/or Chemaxon.

All reactions involving air- or moisture-sensitive reagents were performed under a nitrogen atmosphere using dried solvents and glassware.

NMR spectra were recorded on a Bruker Avance III HD 500 MHz, 400 MHz, 300 MHz or 250 MHz spectrometer.

Specific Optical Rotations were measured using a Rudolph Research Analytical Autopol 1 polarimeter, S2 Serial 32026.

Column chromatography separations were performed using Biotage® Isolera 4 system with Biotage® SNAP KP-Sil pre-packed silica gel columns.

uPLC-MS
Performed on a Waters Acquity UPLC system coupled to a Waters Acquity PDA detector, an ELS detector and an MSD (Scan Positive: 150-850).
Method 1
Phenomenex Kinetex-XB, C18 2.1×100 mm, 1.7 μm column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
|------|-----|-----|
| 0.00 | 95.00 | 5.00 |
| 5.30 | 0.00 | 100.0 |
| 5.80 | 0.00 | 100.0 |
| 5.82 | 95.00 | 5.00 |

HPLC-MS
1. Performed on a Shimadzu LCMS-2010EV system coupled to SPD-M20A PDA and PL 2100 detectors.
Method 2
HPLC_X-Bridge (Ammonium Bicarbonate)
Column: X-Bridge C18 (4.6×150 mm, 3.5 μm)
Mobile Phase A: 10 mM ammonium bicarbonate in water
Mobile Phase B: acetonitrile
Gradient program: Flow rate 1 mL/minute; column temperature 40° C.

| Time | A % | B % |
|------|-----|-----|
| 0.00 | 95.00 | 5.00 |
| 8.00 | 0.00 | 100.0 |
| 12.00 | 0.00 | 100.0 |
| 14.00 | 95.00 | 5.00 |

Method 3
Phenomenex Kinetex Core-Shell C8 50×2.1 mm, 5 μm column, protected by
Phenomenex 'Security Guard' column
Mobile Phase A: 0.1% formic acid in water
Mobile Phase B: 0.1% formic acid in acetonitrile
Gradient program: Flow rate 1.2 mL/minute; column temperature 40° C.

| Time | A % | B % |
|------|-----|-----|
| 0.00 | 95.00 | 5.00 |
| 1.20 | 0.00 | 100.0 |
| 1.30 | 0.00 | 100.0 |
| 1.31 | 95.00 | 5.00 |

Method 4
Waters Atlantis dC18 (2.1×100 mm, 3 μm) column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
|------|-----|-----|
| 0.00 | 95.00 | 5.00 |
| 5.00 | 0.00 | 100.0 |
| 5.40 | 0.00 | 100.0 |
| 5.42 | 95.00 | 5.00 |

2. Performed on an Agilent 1200-6120 LC-MS system coupled to Detection (230 to 400 nm and 215 nm) and Mass Spec Detection Agilent 6120 Mass Spectrometer (ES) m/z 120 to 800.

Method 5
X-Bridge C18 Waters 2.1×20 mm, 2.5 m column
Mobile Phase A: 10 mM ammonium formate in water+0.1% formic acid
Mobile Phase B: acetonitrile+5% water+0.1% formic acid
Gradient program: Flow rate 1 mL/minute

| Time | A % | B % |
|------|-----|-----|
| 0.00 | 94.00 | 6.00 |
| 1.50 | 5.00 | 95.00 |
| 2.25 | 5.00 | 95.00 |
| 2.50 | 94.00 | 6.00 |

Method 6
X-Bridge C18 Waters 2.1×20 mm, 2.5 m column
Mobile Phase A: 10 nM ammonium formate in water+0.1% ammonia solution
Mobile Phase B: acetonitrile+5% water+0.1% ammonia solution
Gradient program: Flow rate 1 mL/minute

| Time | A % | B % |
|------|-----|-----|
| 0.00 | 96.00 | 4.00 |
| 4.00 | 5.00 | 95.00 |
| 5.00 | 5.00 | 95.00 |
| 5.10 | 96.00 | 4.00 |

Automated Preparative Reverse Phase HPLC Purification
Performed using a Gilson system with a Gilson 306 pump, a Gilson 215 autoinjector, a Gilson 215 fraction collector and a Gilson 156 UV detector.

Method 7
X-Bridge C18 Waters 30×100 mm, 5 m column
Mobile Phase A: water+0.2% ammonia solution
Mobile Phase B: acetonitrile+0.2% ammonia solution
Gradient program: Flow rate 40 mL/minute

| Time | A % | B % |
|------|-----|-----|
| 0.00 | 95 | 5 |
| 2.00 | 95 | 5 |
| 2.50 | 75 | 25 |
| 16.50 | 35 | 65 |
| 17.00 | 0 | 100 |
| 19.00 | 0 | 100 |
| 19.50 | 95 | 5 |

Chiral SFC Separation
Method 8
Waters Thar 3100 SFC system connected to a Waters 2998 PDA detector
HPLC-MS
Performed on a Waters ZQ system coupled to Waters 2996 PDA and Waters 2420 detectors.

Method 9
Phenomenex Gemini-NX C18 2.0 mm×50 mm, 3 μm column
Mobile Phase A: 2 mM $NH_4HCO_3$ modified to pH 10 with $NH_4OH$
Mobile Phase B: acetonitrile
Gradient program: Flow rate 1 mL/minute; column temperature 40° C.

| Time | A % | B % |
|------|-----|-----|
| 0.00 | 99.00 | 1.00 |
| 1.80 | 0.00 | 100.00 |
| 2.10 | 0.00 | 100.00 |
| 2.30 | 99.00 | 1.00 |
| 3.50 | 99.00 | 1.00 |

Method 10
Waters Atlantis dC18 4.6×50 mm, 3 μm column
Mobile Phase A: 0.1% formic acid in water
Mobile Phase B: 0.1% formic acid in acetonitrile
Gradient program: Flow rate 0.8 mL/minute; column temperature 40° C.

| Time | A % | B % |
|------|-----|-----|
| 0.00 | 30.00 | 70.00 |
| 3.00 | 90.00 | 10.0 |
| 6.00 | 90.00 | 10.0 |

Method 11
HPLC_X-Bridge (Ammonium Bicarbonate)
Column: X-Bridge C18 (4.6×150 mm, 3.5 μm)
Mobile Phase A: 10 mM ammonium bicarbonate in water
Mobile Phase B: acetonitrile
Gradient program: Flow rate 1.2 mL/minute; column temperature 40° C.

| Time | A % | B % |
|------|-----|-----|
| 0.00 | 98.00 | 2.00 |
| 6.00 | 15.00 | 85.0 |
| 8.00 | 15.00 | 85.0 |
| 9.00 | 0.00 | 100.0 |
| 12.0 | 0.00 | 100.0 |

Method 12
Waters Atlantis dC18 4.6×50 mm, 3 μm column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
|------|-----|-----|
| 0.00 | 50.00 | 50.00 |
| 3.00 | 95.00 | 5.00 |
| 6.00 | 95.00 | 5.00 |

Method 13
Sunfire C18 Waters 30×100 mm, 10 μm column
Mobile Phase A: water+0.1% formic acid
Mobile Phase B: acetonitrile+0.1% formic acid
Gradient program: Flow rate 40 mL/minute

| Time | A % | B % |
| --- | --- | --- |
| 0.00 | 90.00 | 10.00 |
| 0.55 | 90.00 | 10.00 |
| 14.44 | 5.00 | 95.00 |
| 16.55 | 5.00 | 95.00 |
| 16.75 | 90.00 | 10.00 |

HPLC-MS
1. Performed on a Shimadzu LCMS-2010EV system coupled to SPD-M20A PDA and PL 2100 detectors.
Method 14
Phenomenex Kinetex Core-Shell C8 50×2.1 mm, 2.6 µm column protected by Phenomenex 'Security Guard' column
Mobile Phase A: 0.1% formic acid in water
Mobile Phase B: 0.1% formic acid in acetonitrile
Gradient program: Flow rate 0.6 mL/minute; column temperature 40° C.

| Time | A % | B % |
| --- | --- | --- |
| 0.00 | 95 | 5 |
| 4.40 | 0 | 100 |
| 5.40 | 0 | 100 |
| 5.42 | 5 | 95 |
| 6.00 | 5 | 95 |

2. Performed on an Agilent 1200-6120 LC-MS system coupled to Detection (230 to 400 nm and 215 nm) and Mass Spec Detection Agilent 6120 Mass Spectrometer (ES) m/z 120 to 800.
Method 15
X-Bridge C18 Waters 2.1×20 mm, 2.5 m column
Mobile Phase A: 10 mM ammonium formate in water+0.1% formic acid
Mobile Phase B: acetonitrile+5% water+0.1% formic acid
Gradient program: Flow rate 1 mL/minute

| Time | A % | B % |
| --- | --- | --- |
| 0.00 | 95.00 | 5.00 |
| 1.50 | 5.00 | 95.00 |
| 2.25 | 5.00 | 95.00 |
| 2.50 | 95.00 | 5.00 | uPLC-MS
Performed using a Waters I-Class UPLC system coupled to PDA and QDa MS detectors
Method 16
Waters XBridge BEH C18 XP 2.5 µm 2.1×50 mm column
Mobile Phase A: 10 mM ammonium formate+0.1% $NH_3$ (pH 10)
Mobile Phase B: acetonitrile+5% $H_2O$+0.1% $NH_3$ (pH 10)
Gradient: Flow rate 1 mL/minute

| Time | A % | B % |
| --- | --- | --- |
| 0 | 95 | 5 |
| 0.1 | 95 | 5 |
| 2.6 | 5 | 95 |
| 2.75 | 5 | 95 |
| 2.8 | 95 | 5 |
| 3 | 95 | 5 |

Method 17
Column: Waters XBridge BEH C18 XP 2.5 µm, 2.1×50 mm
Mobile Phase A: 10 mM ammonium formate+0.1% formic acid (pH 3)
Mobile Phase B: acetonitrile+5% $H_2O$+0.1% formic acid (pH 3)
Gradient: Flow rate 1 mL/minute

| Time | A % | B % |
| --- | --- | --- |
| 0 | 95 | 5 |
| 0.1 | 95 | 5 |
| 2.6 | 5 | 95 |
| 2.75 | 5 | 95 |
| 2.8 | 95 | 5 |
| 3 | 95 | 5 |

Automated Preparative Reverse Phase HPLC Purification
1. Performed using a Gilson system with a Gilson 331 & 332 pump, a Gilson GX281 autoinjector, a Gilson GX281 fraction collector and a Gilson 155 & 157 UV detector
Method 18
X-Bridge C18 Waters 30×100 mm, 10 m column
Mobile Phase A: water+0.2% ammonia solution
Mobile Phase B: acetonitrile+0.2% ammonia solution
Gradient program: Flow rate 40 mL/minute

| Time | A % | B % |
| --- | --- | --- |
| 0.00 | 90 | 10 |
| 0.55 | 90 | 10 |
| 14.44 | 5 | 95 |
| 16.55 | 5 | 95 |
| 16.75 | 90 | 10 |

2. Performed using a Gilson system with a Gilson 331 & 332 pump, a Gilson GX281 autoinjector, a Gilson GX281 fraction collector and a Gilson 159 UV detector
Method 19
Column: Sunfire C18 Waters 30×100 mm, 10 m column
Mobile Phase A: water+0.1% formic acid
Mobile Phase B: acetonitrile+0.1% formic acid
Gradient program: Flow rate 40 mL/minute

| Time | A % | B % |
| --- | --- | --- |
| 0.00 | 70 | 30 |
| 0.55 | 70 | 30 |
| 11.00 | 5 | 95 |
| 13.10 | 5 | 95 |
| 13.31 | 70 | 30 |

HPLC-MS
Performed using an Agilent 1200RR-6140 LC-MS system, with an Agilent binary pump and Agilent DAD (230-400 nm) module 6140 mass detection (ES) m/z 100-1000
Method 20
Column: XBridge C18, 2.1×20 mm, 2.5 m
Mobile Phase A: 10 mM ammonium formate in water+0.1% ammonia solution
Mobile Phase B: acetonitrile+5% water+0.1% ammonia solution
Gradient: Flow rate 1 mL/minute

| Time | A % | B % |
| --- | --- | --- |
| 0.00 | 95.10 | 5.00 |
| 4.00 | 5.00 | 95.00 |
| 5.00 | 5.00 | 95.00 |
| 5.10 | 95.10 | 5.00 |

Automated Preparative Reverse Phase HPLC Purification
Performed on a Waters FractionLynx LC-MS prep system coupled to a Waters 2998 PDA (230 to 400 nm) and Mass Spec Detection Waters 3100 Mass Spectrometer (ES) m/z 120 to 800
Method 21
Column: XBridge Prep C18 (19×100 mm, 5 μm)
Mobile Phase A: 10 mM ammonium bicarbonate in water+0.1% ammonia solution
Mobile Phase B: acetonitrile+5% water+0.1% ammonia solution
Gradient: Flow rate 19 mL/minute

| Time | A % | B % |
|------|------|------|
| 0.00 | 65.00 | 35.00 |
| 2.50 | 65.00 | 35.00 |
| 11.00 | 50.00 | 50.00 |
| 11.50 | 5.00 | 95.00 |
| 13.0 | 65.00 | 35.00 |

SFC Separation
Performed on a Waters SFC Prep 100 FractionLynx system, with a 2545 quaternary pump, coupled to a 2998 PDA (220-400 nm) and an SQD2 mass spectrometer m/z 150-800.
Method 22
Waters Viridis 2-EP 19×150 mm, 5 μm column
Column Temp: 40° C.
Flow rate: 100 mL/minute
ABPR: 120 bar
Gradient program: 3-40% MeOH (+0.1% NH$_4$OH) over 6 minutes Intermediate 1

Methyl 2-[(2-ethylpyrazole-3-carbonyl)amino]acetate

DIPEA (35.4 mL, 214 mmol) was added to a stirred solution of methyl 2-amino-acetate hydrochloride (8.96 mL, 71.4 mmol), 2-ethylpyrazole-3-carboxylic acid (10 g, 71.4 mmol) and HATU (32.56 g, 85.6 mmol) in anhydrous DMF (90 mL) under a nitrogen atmosphere. The reaction mixture was stirred at room temperature for 16 h, then diluted with water (50 mL) and saturated aqueous sodium hydrogen carbonate solution (50 mL). The aqueous layer was extracted with tert-butyl methyl ether (3×200 mL), followed by 9:1 DCM/MeOH (2×150 mL), then 4:1 DCM/MeOH (2×150 mL). The organic extracts were combined and concentrated in vacuo. The resulting material was purified by flash column chromatography, using a gradient of ethyl acetate in heptane (0-80%), to afford the title compound (20.9 g, 78%) as a yellow oil. $\delta_H$ (250 MHz, CDCl$_3$) 7.47 (d, J 2.0 Hz, 1H), 6.58 (d, J 2.1 Hz, 1H), 6.53 (br s, 1H), 4.59 (q, J 7.2 Hz, 2H), 4.18 (d, J 5.2 Hz, 2H), 3.80 (s, 3H), 1.43 (t, J 7.2 Hz, 3H). HPLC-MS (method 5): MH+ m/z 212, RT 0.86 minutes.

Intermediate 2

2-[(2-Ethylpyrazole-3-carbonyl)amino]acetic acid

A solution of lithium hydroxide monohydrate (3.02 g, 72.0 mmol) in water (60 mL) was added to a stirred solution of Intermediate 1 (56% purity, 20.88 g, 55.36 mmol) in THF (120 mL). The reaction mixture was stirred at 50° C. for 3 h. The volatiles were removed in vacuo and the aqueous residue was extracted with ethyl acetate (2×100 mL). The aqueous phase was treated with 3M aqueous hydrochloric acid (pH 1-2) and extracted with 9:1 DCM/MeOH (2×100 mL), followed by 4:1 DCM/MeOH (2×200 mL). The organic extracts were combined and concentrated in vacuo to give the title compound (7.85 g, 37%) as a yellow oil. The aqueous phase was further extracted with 1:1 isopropanol/DCM (4×150 mL) to give a second batch of the title compound (6.27 g, 40%) as a white solid. $\delta_H$ (500 MHz, CDCl$_3$) 7.53 (d, J 2.0 Hz, 1H), 6.61 (d, J 2.0 Hz, 1H), 6.59-6.51 (m, 1H), 4.63 (q, J 7.2 Hz, 2H), 4.26 (d, J 5.2 Hz, 2H), 1.47 (t, J 7.2 Hz, 3H). HPLC-MS (method 5): MH+ m/z 198, RT 0.33 minutes.

Intermediate 3

2-(2-Ethylpyrazol-3-yl)-4H-oxazol-5-one

To stirred solution of Intermediate 2 (51% purity, 7.85 g, 20.3 mmol) in dry DCM (50 mL) was added EDC.HCl (1:1) (5.06 g, 26.39 mmol) portionwise. The reaction mixture was stirred at ambient temperature for 2 h, then concentrated in vacuo. The resulting orange oil was diluted with water (50 mL) and extracted with tert-butyl methyl ether (3×70 mL). The organic extracts were combined, washed with water (3×50 mL) and brine (50 mL), and dried over sodium sulfate, then filtered and concentrated in vacuo, to afford the title compound (2.8 g, 66%) as an orange oil. $\delta_H$ (500 MHz, CDCl$_3$) 7.56 (d, J 2.0 Hz, 1H), 6.82 (d, J 2.0 Hz, 1H), 4.66 (q, J 7.2 Hz, 2H), 4.43 (s, 2H), 1.46 (t, J 7.2 Hz, 3H). HPLC-MS (method 3): MH+ m/z 180, RT 0.59 minutes.

Intermediate 4

4-(5-Chlorobicyclo[4.2.0]octa-1,3,5-trien-7-ylidene)-2-(1-ethyl-1H-pyrazol-5-yl)-4,5-dihydro-1,3-oxazol-5-one Titanium tetrachloride in DCM (1M, 2.62 mL, 2.62 mmol) was added to anhydrous THF (3.5 mL) at −10° C. A solution of Intermediate 3 (178 mg, 0.85 mmol) in anhydrous THF (1.5 mL) and a solution of 5-chlorobicyclo[4.2.0]octa-1,3,5-trien-7-one (100 mg, 0.66 mmol) in anhydrous THF (1.5 mL) were added portionwise sequentially. The reaction mixture was stirred at 0° C. for 20 minutes, then anhydrous pyridine (0.46 mL, 5.69 mmol) was added dropwise at 0° C. over 30 minutes. The reaction mixture was stirred at 0° C. for 2 h, and at room temperature for a further 16 h, then quenched by the addition of saturated aqueous ammonium chloride solution (7 mL). Stirring was continued for a further 10 minutes, then the solution was extracted with ethyl acetate (2×15 mL). The organic extracts were combined, washed with brine (15 mL) and dried over magnesium sulfate, then filtered and concentrated in vacuo. The residue was purified by flash column chromatography, using a gradient of ethyl acetate in heptane (0-100%), to afford the title compound (191 mg, 70%) as a yellow-orange solid. $\delta_H$ (500 MHz, DMSO-d$_6$) 7.70 (d, J 2.0 Hz, 1H), 7.61-7.52 (m, 1H), 7.48 (d, J 8.1 Hz, 1H), 7.40 (d, J 7.1 Hz, 1H), 7.01 (d, J 2.0 Hz, 1H), 4.76 (q, J 7.1 Hz, 2H), 4.07 (s, 2H), 1.40 (t, J 7.1 Hz, 3H). HPLC-MS (method 5): MH+ m/z 314 and 316, RT 2.07 minutes.

Intermediate 5

Methyl 2-cyclooctylidene-2-formamidoacetate

A solution of potassium tert-butoxide in THF (1M, 48 mL, 48 mmol) was added dropwise to a solution of methyl isocyanoacetate (4.0 mL, 41.8 mmol) in anhydrous THF (40 mL) at approximately −65° C. under nitrogen. After stirring for 5 minutes, a solution of cyclooctanone (5 g, 39.62 mmol) in anhydrous THF (20 mL) was added slowly at −70° C. The reaction mixture was stirred at −70° C. for 30 minutes, then the cooling bath was removed and the mixture was allowed to warm to 20° C. with stirring under nitrogen for 60 h. The resultant deep red solution was quenched with water (100 mL) and stirred at 20° C. for 1 h. The residue was extracted with ethyl acetate (3×100 mL). The combined organic extracts were washed with brine (50 mL) and dried over magnesium sulfate, then filtered and concentrated in vacuo. The resulting crude viscous orange oil was separated by flash column chromatography using a gradient of ethyl acetate in heptane (0-90%) to afford the title compound (5.37 g, 58%) as an orange viscous oil, which solidified upon standing. Major rotamer: $\delta_H$ (500 MHz, DMSO-$d_6$) 9.31 (s, 1H), 8.01 (d, J 1.5 Hz, 1H), 3.60 (s, 3H), 2.52-2.47 (m, 2H), 2.31-2.23 (m, 2H), 1.74-1.60 (m, 4H), 1.50-1.31 (m, 6H). HPLC-MS (method 5): MNa+ m/z 248, RT 1.63 minutes.

Intermediate 6

Methyl 2-cyclooctyl-2-formamidoacetate

Magnesium turnings (3.15 g, 129.60 mmol) were added carefully to a stirred solution of Intermediate 5 (2.91 g, 12.95 mmol) in anhydrous methanol (65 mL) at 0° C. under nitrogen. The suspension was stirred at 0° C. for 1 h, then allowed to warm to 20° C. over 2 h. Stirring of the turbid suspension was continued at 20° C. for 16 h. An additional portion of magnesium turnings (1 g, 41.14 mmol) was added, and the suspension was stirred at 20° C. for 3.5 h under nitrogen. The mixture was carefully concentrated in vacuo. The residue was suspended in ethyl acetate (100 mL) and water (200 mL), then cooled to 0° C. Aqueous hydrochloric acid (1M, 100 mL) was cautiously added, then concentrated hydrochloric acid was cautiously added (pH 5) to aid dissolution of the solids. The organic phase was separated, then the aqueous suspension was treated with concentrated hydrochloric acid (pH 4) and the material was extracted with ethyl acetate (100 mL). The aqueous suspension was treated with concentrated hydrochloric acid (pH 2) and the material was extracted with ethyl acetate (100 mL). The aqueous suspension was further treated with concentrated hydrochloric acid (pH 1) and the material was extracted with ethyl acetate (100 mL). The combined organic extracts were washed with brine (50 mL) and dried over magnesium sulfate, then filtered and concentrated in vacuo. The resulting crude orange viscous oil was separated by flash column chromatography, using a gradient of ethyl acetate in heptane (0-80%), to afford the title compound (1.53 g, 48%) as an orange viscous oil. Major rotamer: $\delta_H$ (500 MHz, DMSO-$d_6$) 8.46 (d, J 8.5 Hz, 1H), 8.06 (s, 1H), 4.29 (dd, J 8.6, 6.1 Hz, 1H), 3.64 (s, 3H), 2.04-1.93 (m, 1H), 1.73-1.19 (m, 14H). HPLC-MS (method 4): MH+ m/z 228, RT 3.94 minutes.

Intermediate 7

Methyl 2-amino-2-cyclooctylacetate hydrochloride

Acetyl chloride (1.9 mL, 26.72 mmol) was added cautiously at 0° C. to a stirred solution of Intermediate 6 (1.54 g, 6.77 mmol) in methanol (68 mL) under nitrogen. After stirring for 5 minutes, the solution was heated at 50° C. for 2 h, then the volatiles were concentrated in vacuo. The resulting crude orange powder was triturated from diethyl ether (40 mL) and the solids were collected by filtration, washing with diethyl ether (2×20 mL). The solids were dried in vacuo at 50° C. for 6 h to afford the title compound (1.43 g, 81%) as a tan powder. $\delta_H$ (500 MHz, DMSO-$d_6$) 8.61 (br s, 3H), 3.86 (d, J 4.4 Hz, 1H), 3.73 (s, 3H), 2.19-2.09 (m, 1H), 1.68-1.37 (m, 13H), 1.32-1.20 (m, 1H). HPLC-MS (method 3): MH+ m/z 200, RT 0.75 and 0.86 minutes.

Intermediate 8

Methyl 2-cyclooctyl-2-(3-methylisoxazole-4-carboxamido)acetate

To a solution of 3-methylisoxazole-4-carboxylic acid (12.9 g, 66.1 mmol) in dry DMF (100 mL) at 0° C. were added DIPEA (54.9 g, 424.6 mmol), EDC.HCl (19.5 g, 101.9 mmol) and HOBt (13.8 g, 101.9 mmol). The reaction mixture was stirred for 15 minutes at 0° C., then Intermediate 7 (20.0 g, 84.9 mmol) was added and the reaction mixture was stirred at r.t. for 48 h. The reaction mixture was poured into ice-cold water (500 mL), and extracted with ethyl acetate (2×400 mL). The organic layer was separated, then washed with ice-cold water (2×100 mL) and 1N HCl (2×50 mL). The organic layer was dried over anhydrous $Na_2SO_4$, then filtered and evaporated in vacuo. The crude residue was purified by silica gel flash column chromatography, using 15% EtOAc in hexane as eluting solvent, to afford the title compound (7.9 g, 41.3%) as a pale yellow viscous oil. LC-MS (method 10): MH+ m/z 309, RT 5.5 minutes.

Intermediate 9

Lithium 2-cyclooctyl-2-(3-methylisoxazole-4-carboxamido)acetate

To a solution of Intermediate 8 (11.01 g, 35.7 mmol) in THF (90 mL) at r.t. were added water (30 mL) and lithium hydroxide monohydrate (2.25 g, 53.6 mmol). The reaction mixture was stirred for 16 h, then evaporated under vacuum. To the residue was added diethyl ether (50 mL). The mixture was stirred for 10 minutes, then filtered. The resultant solid was washed with diethyl ether (50 mL) and pentane (50 mL), then dried under vacuum, to afford the title compound (9.51 g, 91%) as an off-white solid. $\delta_H$ (400 MHz, DMSO-d) 9.69 (s, 1H), 8.21 (s, 1H), 4.11 (dd, J 8.0, 4.0 Hz, 1H), 2.35 (s, 3H), 2.05 (br s, 1H), 1.65-1.35 (m, 14H). LC-MS (method 12): MH+ m/z 295, RT 5.4 minutes.

Intermediate 10 trans-(4-Methylcyclohexyl)methanol

To a cold (−5° C. to −20° C.) solution of trans-4-methylcyclohexanecarboxylic acid (68.5 g, 0.481 mol) in THF (550 mL) was added a solution of lithium aluminum hydride (2.4M in THF, 200 mL, 0.48 mol) slowly over circa 1 h. The mixture was stirred at −20° C. for 1.5 h, then allowed to warm to ambient temperature. The mixture was re-cooled in an ice-salt bath before water (16 mL), aqueous sodium hydroxide solution (15 wt %, 16 mL), and water (40 mL) were slowly and cautiously added. The resulting viscous mixture was stirred for 10 minutes, then diethyl ether (500 mL) was added. The resulting suspension was filtered through a pad of kieselguhr. The solvents were evaporated under reduced pressure to afford the title compound (63.5 g, 100%) as a clear, colourless mobile oil. $\delta_H$ (500 MHz, CDCl$_3$) 3.44 (d, J 6.3 Hz, 2H), 1.79-1.69 (m, 4H), 1.47-1.23 (m, 3H), 1.04-0.89 (m, 4H), 0.88 (d, J 6.6 Hz, 3H).

Intermediate 11 trans-4-Methylcyclohexanecarbaldehyde

To a cold (−10° C. to −5° C.) solution of Intermediate 10 (30.31 g, 0.229 mol) in DCM (250 mL), DIPEA (122 mL, 1.15 mol) and DMSO (81.4 mL, 0.688 mol) was added solid pyridine-sulfur trioxide complex (73 g, 0.458 mol) portionwise, maintaining the internal temperature below 20° C. The reaction mixture was stirred at ambient temperature for 16 h, then washed in turn with aqueous citric acid (1M, 200 mL) and brine (200 mL). The organic layer was filtered through phase separating filter paper. The solvent was removed under reduced pressure to afford the title compound (34.9 g, 100%) as a pale yellow oil. $\delta_H$ (250 MHz, CDCl$_3$) 9.61 (d, J 1.6 Hz, 1H), 2.28-2.03 (m, 1H), 1.95 (m, 2H), 1.80 (m, 2H), 1.56-1.14 (m, 3H), 1.07-0.80 (m, 5H, including the Me signal at δ 0.90 (d, J 6.5 Hz)).

Intermediate 12

(S)-4-Methyl-N-[(1E)-(trans-4-methylcyclohexyl)methylidene]benzenesulfinamide

To a solution of Intermediate 11 (34.9 g, 229 mmol) and (S)-4-methylbenzenesulfinamide (35.6 g, 229 mmol) in DCM (1.2 L) was added titanium(IV) ethoxide (85-90% purity, 174.5 g, 160 mL). The resulting solution was heated at reflux for 2 h. The reaction mixture was cooled to ambient temperature, then water (300 mL) was added slowly. The resulting thick paste was filtered through a pad of kieselguhr, then rinsed with DCM (300 mL) and water (300 mL). The two phases were separated. The DCM phase was dried over anhydrous sodium sulfate and filtered, then the solvent was evaporated, to give the title compound (55.7 g, 78%) as a yellow oil, which partially solidified upon standing. $\delta_H$ (250 MHz, CDCl$_3$) 8.11 (d, J 4.9 Hz, 1H), 7.70-7.49 (m, 2H), 7.29 (m, 2H), 2.40 (s, 2H), 2.38-2.24 (m, 1H), 2.06-1.66 (m, 4H), 1.53-1.16 (m, 4H), 1.07-0.91 (m, 2H), 0.89 (d, J 6.5 Hz, 3H).

Intermediate 13

N—[(S)-Cyano(trans-4-methylcyclohexyl)methyl]-(S)-4-methylbenzenesulfinamide

To a solution of diethylaluminium cyanide (1M in toluene, 103 mL, 103 mmol) in THF (400 mL) at −78° C. was added anhydrous isopropyl alcohol (5.3 mL, 69 mmol). The mixture was stirred at −78° C. for 30-60 minutes, then cannulated into a solution of Intermediate 12 (90% purity, 20.2 g, 69 mmol) in THF (800 mL) at −78° C. over circa 45 minutes. The mixture was allowed to warm to room temperature, then stirred overnight. The mixture was cooled in an ice-water bath, then saturated aqueous ammonium chloride solution (300 mL) was added; some gas was evolved and the internal temperature increased to circa 30° C. After 1 h, the mixture was filtered through a pad of kieselguhr, then the pad was washed with water (300 mL) and ethyl acetate (300 mL). The organic layers were divided, and the aqueous layers were washed with more ethyl acetate. The combined organic layers were washed with brine, dried over anhydrous sodium sulfate and filtered, then the solvent was evaporated. The resulting pale yellow oil, which solidified upon standing, was taken up in hot heptane-ethyl acetate, then allowed to crystallise, to afford the title compound (7.78 g, 38%) as a white solid. The residues were evaporated and purified by automated column chromatography to give a clean mixture of the two diastereoisomers. Recrystallisation of this mixture from ethyl acetate-heptane, seeded using some of the first crop, gave a further batch of the title compound (4.05 g, 20%). $\delta_H$ (250 MHz, CDCl$_3$) 7.61 (d, J 8.3 Hz, 2H), 7.36 (d, J 8.2 Hz, 3H), 4.50 (d, J 7.8 Hz, 1H), 3.95 (dd, J 7.9, 5.8 Hz, 1H), 2.43 (s, 3H), 2.25-1.78 (m, 3H), 1.44-0.91 (m, 5H), 0.89 (d, J 6.5 Hz, 3H).

Intermediate 14

[(S)-Cyano(trans-4-methylcyclohexyl)methyl]ammonium chloride

To a stirred solution of Intermediate 13 (6.6 g, 22.73 mmol) in dry methanol (130 mL) was added 4M hydrogen chloride in 1,4-dioxane (60 mL) dropwise over 2 minutes, whereupon an exotherm to 26° C. had occurred. The reaction mixture was cooled externally and 4M hydrogen chloride (60 mL) in 1,4-dioxane was added over 3 minutes. After 5 minutes, the flask was stoppered and the reaction mixture was stirred at ambient temperature for 2 h. The volatiles were concentrated in vacuo. Diethyl ether (100 mL) was added, then the mixture was sonicated and stirred for 15 minutes. The solids were filtered off and washed with diethyl ether (3×100 mL), then dried under a stream of nitrogen gas, to afford the title compound (4.10 g, 96%) as a white solid. $\delta_H$ (500 MHz, DMSO-d$_6$) 9.20 (s, 3H), 4.50 (d, J 5.5 Hz, 1H), 1.92-1.77 (m, 3H), 1.77-1.67 (m, 2H), 1.29 (ddp, J 11.4, 6.8, 3.4 Hz, 1H), 1.18-1.01 (m, 2H), 0.95-0.83 (m, 5H). HPLC-MS (method 1): MH+ m/z 153, RT 0.46 minutes (100%). Chiral LC (method 8, Amylose-2 25 cm, 80% heptane-20% 2-propanol, 1 mL/min): RT 8.84 minutes (S, 93%).

Intermediate 15

[(S)-Carboxy(trans-4-methylcyclohexyl)methyl]ammonium chloride

A stirred solution of Intermediate 14 (4.05 g, 21.46 mmol) in a mixture of acetic acid (17 mL) and concentrated hydrochloric acid (85 mL) was heated to an external temperature of 130° C. (105° C. internal temperature). After 3 h, another portion of concentrated hydrochloric acid (25 mL) was added, followed by another portion (25 mL) after a further 2 h. The reaction mixture was heated for 1 h, then cooled. The precipitated solid was filtered and rinsed with tert-butyl methyl ether, then dried in vacuo, to afford the title compound (3.04 g, 68%) as a white solid. $\delta_H$ (500 MHz, DMSO-d$_6$) 8.35 (s, 3H), 3.69 (d, J 4.2 Hz, 1H), 1.82-1.65 (m, 4H), 1.64-1.54 (m, 1H), 1.32-1.18 (m, 2H), 1.15-1.02 (m, 1H), 0.93-0.80 (m, 5H). HPLC-MS (method 3): MH+ m/z 172, RT 0.63 minutes.

Intermediate 16

4-(4-Bromo-2-methylphenyl)oxane-4-carbonitrile

Sodium bis(trimethylsilyl)amide solution in THF (1M, 19.5 mL, 19.5 mmol) was added dropwise to a solution of 2-(4-bromo-2-methylphenyl)acetonitrile (3.75 g, 17.85 mmol) in THF (90 mL) at 0° C. After stirring for 0.5 h, the cooling bath was removed and the reaction mixture was stirred at 20° C. for 0.5 h. 1-Iodo-2-(2-iodoethoxy)ethane (2.8 mL, 19.67 mmol) was added dropwise. The reaction mixture was stirred for 0.5 h at 20° C. Sodium bis(trimethylsilyl)amide solution in THF (1M, 19.5 mL, 19.5 mmol) was added dropwise. The reaction mixture was stirred for 18 h at 20° C., then quenched with saturated aqueous ammonium chloride solution (25 mL) and diluted with water (25 mL). The aqueous layer was extracted with EtOAc (3×50 mL). The combined organic extracts were washed with brine (50 mL) and dried over sodium sulfate, then filtered and concentrated in vacuo. The resulting brown oil was separated by flash column chromatography on silica, using a gradient of tert-butyl methyl ether in heptane (0-25%), to afford the title compound (2.3 g, 45%) as a yellow solid. $\delta_H$ (250 MHz, CDCl$_3$) 7.47-7.36 (m, 2H), 7.16 (d, J 8.4 Hz, 1H), 4.16-4.06 (m, 2H), 4.06-3.91 (m, 2H), 2.65 (s, 3H), 2.33-2.21 (m, 2H), 2.17-1.99 (m, 2H). HPLC-MS (method 9): [M+water]+ m/z 297 and 299, RT 1.80 minutes.

Intermediate 17

5-Bromo-2,3-dihydrospiro[indene-1,4'-oxane]-2-one

Lithium diisopropylamide in THF/heptane/ethylbenzene (2M, 6 mL, 12.0 mmol) was added dropwise to a solution of Intermediate 16 (2.3 g, 8.05 mmol) in THF (80 mL) at −78° C. The reaction mixture was stirred at −78° C. for 3 h, then quenched with aqueous hydrochloric acid (2M, 20 mL) and stirred for 25 minutes at 20° C. The aqueous layer was extracted with DCM (2×50 mL). The combined organic extracts were dried over sodium sulfate, then filtered and concentrated in vacuo. The resulting pale brown solid was separated by flash column chromatography on silica, using a gradient of tert-butyl methyl ether in heptane (0-50%), to afford the title compound (2.1 g, 88%) as a pale brown solid. $\delta_H$ (250 MHz, CDCl$_3$) 7.56-7.43 (m, 2H), 7.24-7.18 (m, 1H), 4.18-4.01 (m, 2H), 3.98-3.82 (m 2H), 3.60 (s, 2H), 2.00-1.82 (m 2H), 1.82-1.67 (m 2H). HPLC-MS (method 9): MH+ m/z 281 and 283, RT 1.73 minutes.

Intermediate 18

5-Bromo-2,3-dihydrospiro[indene-1,4'-oxane]-2-ol

Sodium borohydride (0.262 g, 6.94 mmol) was added portionwise to a solution of Intermediate 17 (0.65 g, 2.31 mmol) in MeOH (10 mL) at 0° C. The reaction mixture was allowed to warm slowly to r.t., then stirred for 18 h at r.t. The solvent was concentrated in vacuo. The residue was partitioned between DCM (25 mL) and water (10 mL). The aqueous layer was extracted with DCM (25 mL). The combined organic extracts were washed with brine (10 mL) and dried over sodium sulfate, then filtered and concentrated in vacuo, to afford the title compound (0.67 g, 99%) as a viscous yellow oil which solidified on standing. $\delta_H$ (250 MHz, CDCl$_3$) 7.46-7.33 (m, 2H), 7.21-7.10 (m, 1H), 4.64-4.51 (m, 1H), 4.05-3.88 (m, 2H), 3.86-3.69 (m, 2H), 3.40-3.26 (m, 1H), 2.86 (dd, J 16.9, 1.6 Hz, 1H), 2.12-1.89 (m, 2H), 1.78-1.64 (m, 1H), 1.53-1.41 (m, 1H). HPLC-MS (method 9): MH+ m/z 283 and 285, RT 1.60 minutes.

Intermediate 19

5-Bromospiro[indene-1,4'-oxane]

p-Toluenesulfonyl chloride (0.38 mL, 2.02 mmol) was added portionwise to a solution of Intermediate 18 (470 mg, 1.62 mmol) and pyridine (0.2 mL, 2.43 mmol) in THF (15 mL). The reaction mixture was stirred at r.t. for 2.5 h. A solution of potassium tert-butoxide in THF (1M, 5.7 mL, 5.7 mmol) was added dropwise. The mixture was stirred for 20 h at 20° C., then cooled to 0° C. and quenched with brine (20 mL). The aqueous layer was extracted with DCM (2×50 mL). The combined organic extracts were dried over sodium sulfate, then filtered and concentrated in vacuo. The resulting cream solid was separated by flash column chromatography on silica, using a gradient of tert-butyl methyl ether in heptane (0-25%), to afford the title compound (413 mg, 95%) as an off-white solid. $\delta_H$ (250 MHz, CDCl$_3$) 7.48 (d, J 1.7 Hz, 1H), 7.37 (dd, J 8.0, 1.7 Hz, 1H), 7.25 (d, J 8.0 Hz, 1H), 7.01 (d, J 5.7 Hz, 1H), 6.75 (d, J 5.7 Hz, 1H), 4.17-4.03 (m, 2H), 3.87-3.70 (m 2H), 2.27-2.10 (m 2H), 1.36-1.25 (m 2H).

Intermediate 20 tert-Butyl N-(spiro[indene-1,4'-oxane]-5-yl)carbamate

A tube was charged with Intermediate 19 (413 mg, 1.56 mmol), tert-butyl carbamate (365 mg, 3.12 mmol) and cesium carbonate (863 mg, 2.64 mmol). The reagents were suspended in toluene (4.4 mL). The reaction mixture was charged with palladium(II) acetate (10.5 mg, 46.72 µmol) and dicyclohexyl[2',4',6'-tri(propan-2-yl)-biphenyl-2-yl]phosphane (44.6 mg, 93.46 µmol). The reaction mixture was purged with nitrogen and sonicated for 5 minutes. The tube was sealed and heated at 90° C. for 18 h. The reaction mixture was quenched with water (20 mL), then extracted with EtOAc (40 mL) and filtered. The layers were separated. The aqueous layer was extracted with EtOAc (40 mL). The combined organic extracts were washed with brine (20 mL) and dried over sodium sulfate, then filtered and concentrated in vacuo. The resulting yellow solid was separated by flash column chromatography on silica, using a gradient of tert-butyl methyl ether in heptane (0-50%), to afford the title compound (480 mg, 95%) as a beige solid. $\delta_H$ (250 MHz, CDCl$_3$) 7.53-7.45 (m, 1H), 7.33-7.24 (m, 1H), 7.09 (dd, J 8.1, 2.0 Hz, 1H), 6.96 (d, J 5.7 Hz, 1H), 6.75 (d, J 5.7 Hz, 1H), 6.50 (s, 1H), 4.17-4.01 (m, 2H), 3.89-3.68 (m, 2H), 2.27-2.06 (m, 2H), 1.55 (s, 9H), 1.36-1.25 (m, 2H). HPLC-MS (method 9): MH+ m/z 302, RT 1.82 minutes.

Intermediate 21

Spiro[indene-1,4'-oxane]-5-amine

Trifluoroacetic acid (1.6 mL, 20.91 mmol) was added to a solution of Intermediate 20 (0.48 g, 1.48 mmol) in DCM (10 mL). The reaction mixture was stirred for 3 h at 20° C., then quenched with saturated aqueous sodium hydrogen carbonate solution (40 mL) and stirred for 15 minutes at 20° C. The layers were separated, and the aqueous layer was extracted with DCM (2×20 mL). The combined organic extracts were washed with saturated aqueous sodium hydrogen carbonate solution (20 mL) and dried over sodium sulfate, then filtered and concentrated in vacuo, to afford the title compound (0.29 g, 95%) as a brown solid. $\delta_H$ (250 MHz, CDCl$_3$) 7.17 (d, J 7.9 Hz, 1H), 6.93 (d, J 5.7 Hz, 1H), 6.75-6.65 (m, 2H), 6.58 (dd, J 7.9, 2.2 Hz, 1H), 4.15-4.02 (m, 2H), 3.85-3.72 (m, 2H), 2.22-2.06 (m 2H), 1.37-1.27 (m 2H). HPLC-MS (Method 9): MH+ m/z 202, RT 1.45 minutes.

Intermediate 22

Spiro[indane-1,4'-tetrahydropyran]-5-amine

10% Palladium on carbon (50% wet, 90 mg, 0.04 mmol) was added to solution of Intermediate 21 (90 mg, 0.42 mmol) in ethanol (2 mL). The reaction mixture was placed under a hydrogen gas atmosphere and stirred for 18 h at 20° C. The catalyst was removed by filtration over kieselguhr, and the filter cake was rinsed with ethanol (2×5 mL). The solvent was concentrated in vacuo, to afford the title compound (103 mg, quantitative) as a brown solid. $\delta_H$ (250 MHz, CDCl$_3$) 7.17-7.07 (m, 1H), 7.07-6.87 (m, 2H), 4.04-3.89 (m, 2H), 3.73-3.55 (m, 2H), 2.97-2.80 (m, 2H), 2.20-2.06 (m, 2H), 2.06-1.84 (m, 3H), 1.52-1.37 (m, 3H). HPLC-MS (method 3): MH+ m/z 204, RT 0.71 minutes.

Intermediate 23

5-Bromo-2-fluorospiro[indene-1,4'-tetrahydropyran]

Diethylaminosulfur trifluoride (1.8 mL, 13.62 mmol) was added to a solution of Intermediate 17 (750 mg, 2.67 mmol) in DCM (7.5 mL) at 0° C. The reaction mixture was allowed to warm, then stirred for 18 h at 20° C. The reaction mixture was cooled to 0° C. and quenched slowly with saturated aqueous sodium hydrogen carbonate solution (50 mL). The mixture was allowed to warm to 20° C., then extracted with DCM (25 mL). The organic layer was washed with saturated aqueous sodium hydrogen carbonate solution (20 mL), water (20 mL) and brine (20 mL), then dried over sodium sulfate, filtered and concentrated in vacuo. The resulting orange oil was separated by flash column chromatography on silica, using a gradient of tert-butyl methyl ether in heptane (0-25%). The resulting pale orange solid was dissolved in THF (4 mL), and lithium bis(trimethyl-silyl)amide solution in THF (1M, 0.57 mL, 0.57 mmol) was added dropwise at 0° C. The reaction mixture was allowed to warm slowly over 1 h to 20° C., then quenched with saturated aqueous sodium hydrogen carbonate solution (5 mL). The aqueous layer was extracted with DCM (2×10 mL). The combined organic extracts were washed with brine (10 mL) and filtered through a hydrophobic frit. The organic filtrate was concentrated in vacuo to afford the title compound (150 mg, quantitative) as a brown solid. $\delta_H$ (250 MHz, CDCl$_3$) 7.29 (d, J 1.7 Hz, 1H), 7.24 (dd, J 8.0, 1.8 Hz, 1H), 7.19-7.14 (m, 1H), 5.90 (s, 1H), 3.96-3.87 (m, 4H), 1.94-1.81 (m, 2H), 1.77-1.64 (m, 2H).

Intermediate 24 tert-Butyl N-(2-fluorospiro[indene-1,4'-tetrahydropyran]-5-yl)carbamate

A tube was charged with Intermediate 23 (182 mg, 0.64 mmol), tert-butyl carbamate (150 mg, 1.28 mmol) and cesium carbonate (355 mg, 1.09 mmol). The reagents were suspended in toluene (2 mL). The reaction mixture was charged with palladium(II) acetate (4.32 mg, 19.23 μmol) and dicyclohexyl[2',4',6'-tri(propan-2-yl)-biphenyl-2-yl]phosphane (18.34 mg, 38.46 μmol). The mixture was purged with nitrogen and sonicated for 5 minutes. The tube was sealed, and the mixture was heated for 3 h at 90° C. After cooling, the reaction mixture was partitioned between water (10 mL) and EtOAc (20 mL), then filtered. The aqueous layer was separated and extracted with EtOAc (20 mL). The combined organic extracts were washed with brine (10 mL) and dried over sodium sulfate, then filtered and concentrated in vacuo. The resulting brown solid was separated by flash column chromatography on silica, using a gradient of tert-butyl methyl ether in heptane (0-50%), to afford the title compound (155 mg, 73%) as a pale brown solid. $\delta_H$ (250 MHz, CDCl$_3$) 7.35-7.29 (m, 1H), 7.24-7.20 (m, 1H), 6.93 (dd, J 8.2, 2.1 Hz, 1H), 6.37 (s, 1H), 5.90 (s, 1H), 3.98-3.87 (m, 4H), 1.90-1.78 (m, 2H), 1.77-1.67 (m, 2H), 1.45 (s, 9H). HPLC-MS (method 9): MH+ m/z 320, RT 1.88 minutes.

Intermediate 25

2-Fluorospiro[indene-1,4'-tetrahydropyran]-5-amine

Trifluoroacetic acid (0.5 mL, 6.45 mmol) was added to a solution of Intermediate 24 (155 mg, 0.47 mmol) in DCM (7.5 mL). The reaction mixture was stirred for 2.5 h at 20° C., then quenched with saturated aqueous sodium hydrogen carbonate solution (20 mL) and stirred for 15 minutes at 20° C. The layers were separated. The aqueous layer was extracted with DCM (2×15 mL). The combined organic extracts were washed with saturated aqueous sodium hydrogen carbonate solution (10 mL), then filtered through a hydrophobic frit. The organic filtrate was concentrated in vacuo to afford the title compound (110 mg, 100%) as a brown solid. $\delta_H$ (250 MHz, CDCl$_3$) 7.10 (d, J 8.0 Hz, 1H), 6.52 (d, J 2.2 Hz, 1H), 6.41 (dd, J 8.0, 2.2 Hz, 1H), 5.83 (s, 1H), 3.96-3.86 (m, 4H), 3.58 (br s, 2H), 1.82-1.71 (m, 4H). HPLC-MS (method 9): MH+ m/z 220, RT 1.52 minutes.

Intermediate 26 tert-Butyl 6-bromospiro[indoline-3,4'-tetrahydropyran]-1-carboxylate

Di-tert-butyl dicarbonate (1.22 g, 5.59 mmol) was added to a stirred suspension of 6-bromospiro[indoline-3,4'-tetrahydropyran] (1 g, 3.73 mmol) and sodium hydrogen carbonate (1.10 g, 13.1 mmol) in THF (20 mL). The reaction mixture was stirred at 20° C. for 72 h. The solids were removed by filtration, and the reaction mixture was concentrated in vacuo. The residue was purified by flash column chromatography on silica, using a gradient of tert-butyl methyl ether in heptane (0-50%), to afford the title compound (1.35 g, 98%) as a yellow oil. $\delta_H$ (500 MHz, CDCl$_3$) 7.85 (d, J 230.4 Hz, 1H), 7.11 (dd, J 8.0, 1.8 Hz, 1H), 6.98 (d, J 8.0 Hz, 1H), 3.98 (dd, J 11.8, 3.8 Hz, 2H), 3.90 (s, 2H), 3.54 (td, J 12.3, 1.9 Hz, 2H), 1.95 (td, J 13.3, 4.7 Hz, 2H), 1.64-1.55 (m, 11H). HPLC-MS (method 3): [M+2H-$^t$Bu]+ m/z 312, 314, RT 1.36 minutes.

Intermediate 27 tert-Butyl 6-aminospiro[indoline-3,4'-tetrahydropyran]-1-carboxylate

A mixture of Intermediate 26 (1.27 g, 3.46 mmol), tris(dibenzylideneacetone)-dipalladium(0) (158 mg, 0.17 mmol) and (2-biphenyl)dicyclohexylphosphine (145 mg, 0.41 mmol) in anhydrous THF (12.7 mL) was purged with nitrogen for 2 minutes. Lithium bis(trimethylsilyl)amide solution in THF (1M, 3.8 mL, 3.8 mmol) was added. The reaction mixture was stirred at 65° C. under nitrogen for 18 h, then cooled to 20° C. A solution of tetrabutylammonium fluoride in THF (1M, 10.4 mL, 10.4 mmol) was added. The mixture was stirred for 0.5 h, diluted with EtOAc (40 mL), and washed with water (30 mL) and brine (30 mL), then dried over sodium sulfate and concentrated in vacuo. The crude residue was purified by flash column chromatography on silica, using a gradient of tert-butyl methyl ether in heptane (0-50%), to afford the title compound (468 mg, 44%) as a yellow gum. $\delta_H$ (500 MHz, CDCl$_3$) 7.33 (s, 1H), 6.93 (d, J 8.0 Hz, 1H), 6.34 (dd, J 8.0, 2.1 Hz, 1H), 3.99 (dd, J 12.0, 3.5 Hz, 2H), 3.87 (s, 2H), 3.67 (s, 2H), 3.56 (td, J 12.2, 1.9 Hz, 2H), 1.96 (td, J 13.4, 4.6 Hz, 2H), 1.59-1.53 (m, 11H). HPLC-MS (method 5): MH+ m/z 305, RT 1.65 minutes.

Intermediate 28 tert-Butyl 6-({2-cyclooctyl-2-[(3-methylisoxazole-4-carbonyl)amino]acetyl}amino)spiro-[indoline-3,4'-tetrahydropyran]-1-carboxylate EDC.HCl (42.3 mg, 0.22 mmol) was added to a stirred solution of Intermediate 9 (65 mg, 0.22 mmol) in anhydrous DCM (0.5 mL). The reaction mixture was stirred at 20° C. for 0.5 h, then anhydrous THF (1 mL), Intermediate 27 (44 mg, 0.14 mmol) and acetic acid (0.12 mL, 2.17 mmol) were added. The reaction mixture was stirred at 60° C. for 1 h under nitrogen, then neutralised with saturated aqueous sodium hydrogen carbonate solution (10 mL) and water (5 mL). The aqueous phase was extracted with EtOAc (3×20 mL). The organic extracts were combined and washed with brine (15 mL), then dried over sodium sulfate, filtered and concentrated in vacuo. The residue was purified by flash column chromatography on silica, using a gradient of tert-butyl methyl ether in heptane (0-100%), to afford the title compound (51 mg 58%) as an off-white solid. HPLC-MS (method 5): MH+ m/z 581.3, RT 2.10 minutes.

Intermediate 29

(2S)-2-(Benzyloxycarbonylamino)-2-(trans-4-methylcyclohexyl)acetic acid

Benzyl chloroformate (3.44 mL, 24.07 mmol) was added to a solution of Intermediate 15 (1 g, 4.81 mmol) dissolved in a 1M aqueous solution of sodium hydroxide (10 mL) and 1,4-dioxane (10 mL). The reaction mixture was stirred at 20° C. for 18 h, then concentrated in vacuo. The aqueous residue was acidified to pH 2 with hydrochloric acid (1M) and extracted with chloroform (2×50 mL). The organic extracts were combined and concentrated in vacuo, then purified by flash column chromatography on silica, using a gradient of tert-butyl methyl ether in heptane (0-50%), to afford the title compound (461 mg, 31%) as an off-white solid. $\delta_H$ (500 MHz, DMSO-d$_6$) 7.89 (d, J 7.9 Hz, 1H), 7.40-7.28 (m, 5H), 5.06 (s, 2H), 4.06 (t, J 7.1 Hz, 1H), 1.79-1.51 (m, 5H), 1.31-1.07 (m 3H), 0.92-0.77 (m 5H).

Intermediate 30 tert-Butyl 6-{[(2S)-2-(benzyloxycarbonylamino)-2-(trans-4-methylcyclohexyl)acetyl]-amino}spiro[indoline-3,4'-tetrahydropyran]-1-carboxylate HATU (299.8 mg, 0.79 mmol) was added to a solution of Intermediate 27 (200 mg, 0.66 mmol) and Intermediate 29 (334 mg, 0.99 mmol) in anhydrous DCM (3.5 mL) and DIPEA (0.23 mL, 1.38 mmol). The reaction mixture was stirred at 20° C. for 18 h, then diluted with water (10 mL) and extracted with DCM (3×20 mL). The organic extracts were combined and filtered through a hydrophobic frit, then concentrated in vacuo. The residue was purified by flash column chromatography on silica, using a gradient of tert-butyl methyl ether in heptane (0-50%), to afford the title compound (393 mg, 97%) as a white solid. $\delta_H$ (500 MHz, DMSO-d$_6$) 9.96 (s, 1H), 7.99 (s, 1H), 7.48-7.11 (m, 8H), 5.02 (s, 2H), 3.98 (t, J 8.1 Hz, 1H), 3.85 (d, J 15.8 Hz, 4H), 3.44 (t, J 11.6 Hz, 2H), 1.88-1.70 (m, 3H), 1.69-1.44 (m, 15H), 1.20-1.12 (m, 2H), 1.07-0.96 (m, 1H), 0.87-0.81 (m, 5H). HPLC-MS (method 5): MH+ m/z 592.2, RT 2.17 minutes.

Intermediate 31 tert-Butyl 6-{[(2S)-2-amino-2-(trans-4-methylcyclohexyl)acetyl]amino}spiro[indoline-3,4'-tetrahydropyran]-1-carboxylate 10% Palladium on charcoal (50% wet, 424 mg, 199 μmol) was added to a stirred suspension of Intermediate 30 (393 mg, 0.66 mmol) in a mixture of THF (15 mL) and ethanol (15 mL). The reaction mixture was placed under a hydrogen gas atmosphere and stirred at 20° C. for 18 h. The catalyst was removed by filtration over kieselguhr, rinsing the filter cake with MeOH (2×15 mL). The filtrate was concentrated in vacuo to afford the title compound (234 mg, 77%) as a colourless gum. $\delta_H$ (500 MHz, DMSO-d$_6$) 9.74 (s, 1H), 8.00 (s, 1H), 7.46-6.97 (m, 2H), 3.87-3.79 (m, 4H), 3.44 (t, J 11.6 Hz, 2H), 3.17 (s, 2H), 3.11-3.04 (m, 1H), 1.87-1.62 (m, 6H), 1.55-1.46 (m, 12H), 1.28-1.15 (m, 2H), 1.06-0.95 (m, 1H), 0.91-0.76 (m, 5H). HPLC-MS (method 3): MH+ m/z 458.1, RT 1.14 minutes.

Intermediate 32 tert-Butyl 6-({(2S)-2-[(2-ethylpyrazole-3-carbonyl)amino]-2-(trans-4-methylcyclohexyl)-acetyl}amino)spiro[indoline-3,4'-tetrahydropyran]-1-carboxylate HATU (291 mg, 0.76 mmol) was added to a solution of Intermediate 31 (200 mg, 0.44 mmol) and 2-ethylpyrazole-3-carboxylic acid (91.9 mg, 0.66 mmol) in anhydrous DCM (9 mL) and DIPEA (433 μL, 2.62 mmol). The reaction mixture was stirred at 20° C. for 18 h, then diluted with water (15 mL) and extracted with DCM (3×30 mL). The organic extracts were combined and washed with brine (15 mL), then dried over sodium sulfate, filtered and concentrated in vacuo. The crude residue was purified by flash column chromatography on silica, using a gradient of tert-butyl methyl ether in heptane (0-100%), to afford the title compound (211 mg, 77%) as a yellow gum. $\delta_H$ (500 MHz, CDCl$_3$) 7.85 (s, 1H), 7.50 (d, J 2.0 Hz, 3H), 7.11 (d, J 8.2 Hz, 1H), 6.67 (d, J 8.3 Hz, 1H), 6.60 (d, J 1.9 Hz, 1H), 4.61 (q, J 7.2 Hz, 2H), 4.43 (t, J 7.6 Hz, 1H), 4.09-3.83 (m, 4H), 3.57 (t, J 11.4 Hz, 2H), 2.03-1.95 (m, 2H), 1.94-1.82 (m, 3H), 1.80-1.72 (m, 2H), 1.58 (s, 9H), 1.46 (t, J 7.2 Hz, 3H), 1.33 (s, 2H), 1.20-1.09 (m, 2H), 1.02-0.93 (m, 1H), 0.90 (t, J 5.6 Hz, 5H). HPLC-MS (method 3): MH+ m/z 580.2, RT 2.10 minutes.

Intermediate 33

Diethyl 2-(2-methoxy-4-nitrophenyl)malonate

To a solution of sodium hydride (1.80 g, 74.9 mmol) in 1,4-dioxane (50 mL) was added diethyl malonate (12.0 g, 74.9 mmol) at 0° C. The reaction mixture was stirred at r.t. for 1 h. CuBr (10.7 g, 74.9 mmol) and 1-bromo-2-methoxy- 4-nitrobenzene (5.74 g, 24.7 mmol) were added. The reaction mixture was stirred at r.t. for 1 h, then heated under reflux for 12 h. The reaction mixture was poured into water (150 mL), then filtered through a pad of Celite. The filtrate was extracted with EtOAc (2×100 mL). The organic layer was separated and washed with brine (100 mL), then dried over anhydrous $Na_2SO_4$ and concentrated in vacuo. The crude residue was purified by column chromatography on silica (0 to 10% EtOAc in hexanes) to afford the title compound (6.00 g, 78%) as a yellow solid. $\delta_H$ (400 MHz, DMSO-$d_6$) 1.18 (t, J 7.09 Hz, 6H), 3.92 (s, 3H), 4.17 (q, J 7.34 Hz, 4H), 5.12 (s, 1H), 7.50 (d, J 8.31 Hz, 1H), 7.82 (d, J 1.96 Hz, 1H), 7.88 (dd, J 8.31, 1.96 Hz, 1H). HPLC-MS (method 6): MH− m/z 310.1, RT 2.01 minutes.

Intermediate 34

Ethyl 2-(2-methoxy-4-nitrophenyl)acetate

To a solution of Intermediate 33 (1.00 g, 3.21 mmol) in DMSO (7 mL) and water (0.1 mL) was added LiCl (0.15 g, 3.53 mmol). The reaction mixture was heated under microwave irradiation at 140° C. for 1 h, then diluted with water (100 mL) and extracted with EtOAc (3×100 mL). The organic layer was separated, washed with water (100 mL) and brine (50 mL), then dried over anhydrous $Na_2SO_4$ and concentrated in vacuo. The crude residue was purified by flash chromatography on silica (0-20% acetone in hexanes) to afford the title compound (0.17 g, 65%) as a yellow oil. $\delta_H$ (400 MHz, DMSO-$d_6$) 1.17 (t, J 7.20 Hz, 3H), 3.74 (s, 2H), 3.89 (s, 3H), 4.08 (q, J 7.34 Hz, 2H), 7.51 (d, J 8.31 Hz, 1H), 7.76 (d, J 1.96 Hz, 1H), 7.83 (dd, J 8.07, 2.20 Hz, 1H).

Intermediate 35

Ethyl 4-(2-methoxy-4-nitrophenyl)tetrahydro-2H-pyran-4-carboxylate

To a solution of Intermediate 34 (2.60 g, 10.9 mmol) in DMF (20 mL) was added sodium hydride (1.04 g, 21.7 mmol) at 0° C. The reaction mixture was stirred at r.t. for 30 minutes, then 1-iodo-2-(2-iodoethoxy)ethane (5.31 g, 16.3 mmol) was added. The reaction mixture was heated at 80° C. for 16 h, then poured into ice and extracted with EtOAc (3×100 mL). The combined organic layers were separated, washed with water (100 mL) and brine (100 mL), then dried over anhydrous $Na_2SO_4$ and concentrated in vacuo. The crude residue was purified by flash chromatography on silica (0-20% EtOAc in hexanes) to afford the title compound (2.00 g, 60%) as a yellow oil. $\delta_H$ (400 MHz, DMSO-$d_6$) 1.06 (t, J 7.09 Hz, 3H), 1.95-2.02 (m, 2H), 2.17-2.22 (m, 2H), 3.64-3.71 (m, 2H), 3.72-3.80 (m, 2H), 3.85 (s, 3H), 4.05 (q, J 6.85 Hz, 2H), 7.66 (d, J 8.80 Hz, 1H), 7.75 (s, 1H), 7.83-7.88 (m, 1H).

Intermediate 36

4-(2-Hydroxy-4-nitrophenyl)tetrahydro-2H-pyran-4-carboxylic acid

To Intermediate 35 (1.00 g, 3.23 mmol) was added a 1M solution of $BBr_3$ in DCM (12.9 mL, 12.9 mmol) at 0° C. The reaction mixture was stirred at r.t. for 2 h, then quenched with water (50 mL) and extracted with DCM (3×50 mL). The organic layer was separated, washed with water (50 mL), and brine (50 mL), then concentrated in vacuo. The residue was dissolved in THF:water (5:1, 30 mL), then LiOH.$H_2O$ (0.41 g, 9.70 mmol) was added. The reaction mixture was stirred at r.t. for 2 h and concentrated in vacuo. The residue was dissolved in water (5 mL) and extracted with DCM (3×30 mL). The aqueous layer was acidified with HCl (2N aqueous solution) to pH 2, then extracted with EtOAc (3×30 mL). The organic layer was separated, washed with water (30 mL) and brine (30 mL), then dried over anhydrous $Na_2SO_4$ and concentrated in vacuo, to afford the title compound (0.60 g, 59%) as an off-white solid, which was utilised without further purification. $\delta_H$ (400 MHz, DMSO-$d_6$) 1.98-2.08 (m, 2H), 2.21-2.26 (m, 2H), 3.61-3.69 (m, 2H), 3.72-3.80 (m, 2H), 7.53 (d, J 8.31 Hz, 1H), 7.59 (d, J 2.45 Hz, 1H), 7.67 (dd, J 8.80, 2.45 Hz, 1H), 10.68 (br s, 1H), 12.25 (br s, 1H). HPLC-MS (method 6): MH− m/z 266.0, RT 1.43 minutes.

Intermediate 37

6-Nitro-2',3',5',6'-tetrahydro-2H-spiro[benzofuran-3,4'-pyran]-2-one

To a solution of Intermediate 36 (0.50 g, 1.87 mmol) in THF (10 mL) was added EDC.HCl (0.72 g, 3.74 mmol), followed by the addition of DIPEA (0.98 mL, 5.61 mmol). The reaction mixture was stirred at r.t. for 16 h, then quenched with water (15 mL) and extracted with EtOAc (3×25 mL). The combined organic layers were separated and dried over anhydrous $Na_2SO_4$, then concentrated in vacuo, to afford the title compound (0.25 g, 54%) as a brown liquid, which was utilised without further purification. $\delta_H$ (400 MHz, DMSO-d) 2.08-2.17 (m, 1H), 2.20-2.30 (m, 1H), 2.54-2.58 (m, 1H), 2.61-2.72 (m, 1H), 4.13-4.24 (m, 1H), 4.43-4.57 (m, 3H), 7.43 (d, J 8.31 Hz, 1H), 7.62 (d, J 1.96 Hz, 1H), 7.75 (dd, J 8.31, 2.45 Hz, 1H).

Intermediate 38

6-Amino-2',3',5',6'-tetrahydro-2H-spiro[benzofuran-3,4'-pyran]-2-one

To a solution of Intermediate 37 (0.23 g, 0.92 mmol) in methanol (15 mL) was added Pd/C (0.02 g, 0.19 mmol). The reaction mixture was stirred at r.t. for 2 h under hydrogen pressure, then filtered through a pad of Celite. The filtrate was concentrated in vacuo to afford the title compound (0.12 g, 59%) as a colourless syrup, which was utilised without further purification. HPLC-MS (method 6): MH+ m/z 220.0, RT 1.51 minutes.

Intermediate 39

2-[4-(Hydroxymethyl)tetrahydropyran-4-yl]-5-nitrophenol

To neat Intermediate 36 (0.60 g, 2.25 mmol) was added borane dimethylsulfide complex solution in THF (2M, 9.00 mL, 18.0 mmol) at 0° C. under inert conditions. The reaction mixture was stirred at r.t. for 16 h, then quenched with saturated aqueous ammonium chloride solution (100 mL) and extracted with EtOAc (3×100 mL). The combined organic layers were washed with water (100 mL) and brine (100 mL), then dried over anhydrous $Na_2SO_4$ and concentrated in vacuo, to afford the title compound (0.55 g, 97%) as an off-white solid, which was utilised without further purification. $\delta_H$ (400 MHz, DMSO-$d_6$) 1.85-1.92 (m, 2H), 2.25-2.29 (m, 2H) 3.35-3.42 (m, 2H), 3.67-3.69 (m, 2H), 3.72 (d, J 5.38 Hz, 2H), 4.58 (t, J 5.38 Hz, 1H), 7.39 (d, J 9.29 Hz, 1H), 7.61-7.65 (m, 2H), 10.49 (s, 1H). HPLC-MS (method 2): MH– m/z 251.9, RT 1.47 minutes.

Intermediate 40

6-Nitrospiro[2H-benzofuran-3,4'-tetrahydropyran]

To a solution of Intermediate 39 (0.70 g, 2.76 mmol) in toluene (15 mL) was added cyanomethyltributylphosphorane (1.33 g, 5.53 mmol). The reaction mixture was heated at 100° C. for 3 h, then concentrated in vacuo. The crude residue was purified by flash chromatography on silica (0-10% EtOAc in hexanes) to afford the title compound (0.50 g, 77%) as an off-white solid. $\delta_H$ (400 MHz, DMSO-$d_6$) 1.60-1.65 (m, 2H), 1.91-1.99 (m, 2H), 3.39-3.49 (m, 2H), 3.83-3.89 (m, 2H), 4.66 (s, 2H) 7.54-7.59 (m, 2H), 7.79 (dd, J 8.31, 1.96 Hz, 1H).

Intermediate 41

Spiro[2H-benzofuran-3,4'-tetrahydropyran]-6-amine

To a solution of Intermediate 40 (0.50 g, 2.13 mmol) in methanol (10 mL) was added $SnCl_2 \cdot 2H_2O$ (1.44 g, 6.38 mmol). The reaction mixture was stirred at r.t. for 16 h, then quenched with saturated aqueous $NaHCO_3$ solution (100 mL) and extracted with EtOAc (2×100 mL). The combined organic layers were concentrated in vacuo. The crude residue was purified by flash chromatography on silica (0-20% EtOAc in hexanes), and SFC purification (method 8, using a Chiralpak IC 250×30 mm, 5 μm column, eluting with 0.1% $NH_3$ in methanol/$CO_2$, flow 80.0 mL/minute), to afford the title compound (0.165 g, 38%) as an off-white solid. $\delta_H$ (400 MHz, DMSO-$d_6$) 1.45-1.49 (m, 2H), 1.73-1.81 (m, 2H), 3.34-3.44 (m, 2H), 3.77-3.85 (m, 2H), 4.33 (s, 2H), 4.95 (s, 2H), 5.98 (d, J 1.75 Hz, 1H), 6.06 (dd, J 7.89, 1.75 Hz, 1H), 6.83 (d, J 7.89 Hz, 1H). HPLC-MS (method 2): MH+ m/z 206.0, RT 1.48 minutes.

Intermediate 42 tert-Butyl 6-bromo-4-fluoro-2-oxoindoline-1-carboxylate

Di-tert-butyl dicarbonate (853.88 mg, 3.91 mmol) in THF (8 mL) was added dropwise to a stirred suspension of 6-bromo-4-fluoroindolin-2-one (900 mg, 3.91 mmol) and $NaHCO_3$ (1.15 g, 13.69 mmol) in THF (10 mL). The reaction mixture was heated, with stirring, at 50° C. for 4.5 h, then the solid was removed by filtration and the solvent was removed in vacuo. The residue was purified by flash column chromatography on silica, using a gradient of tert-butyl methyl ether in heptane (0-20%), to afford the title compound (1.04 g, 80%) as a yellow solid. $\delta_H$ (500 MHz, $CDCl_3$) 7.86 (s, 1H), 7.07 (dd, J 7.9, 1.5 Hz, 1H), 3.60 (s, 2H), 1.64 (s, 9H). HPLC-MS (ES+) (method 14): MH+ m/z 328.2, 330.0, RT 2.05 minutes.

Intermediate 43 tert-Butyl 6-bromo-4-fluoro-2-oxospiro[indoline-3,4'-tetrahydropyran]-1-carboxylate A stirred solution of Intermediate 42 (0.8 g, 2.42 mmol) and 1-iodo-2-(2-iodo-ethoxy)ethane (0.38 mL, 2.67 mmol) in anhydrous DMF (16 mL) was cooled to −15° C. and purged with nitrogen for 5 minutes, then caesium carbonate (3.16 g, 9.69 mmol) was added. The reaction mixture was stirred for 2 h, with warming to 20° C. Water (30 mL) was added, and the aqueous layer was extracted with tert-butyl methyl ether (3×30 mL). The combined organic layers were washed with water (2×30 mL) and brine (30 mL), then dried over sodium sulfate, filtered and concentrated in vacuo. The resulting crude material was purified by flash column chromatography on silica, using a gradient of tert-butyl methyl ether in heptane (0-15%), to afford the title compound (927.9 mg, 86%) as a yellow solid. $\delta_H$ (500 MHz, $CDCl_3$) 7.90 (d, J 1.3 Hz, 1H), 7.06 (dd, J 9.1, 1.6 Hz, 1H), 4.26 (t, J 11.8 Hz, 2H), 3.89 (dd, J 11.9, 3.6 Hz, 2H), 2.45-2.33 (m, 2H), 1.75-1.69 (m, 2H), 1.65 (s, 9H). HPLC-MS (ES+) (method 14): [M+H-BOC]+ m/z 300.0, 302.0, RT 2.11 minutes.

Intermediate 44

6-Bromo-4-fluorospiro[indoline-3,4'-tetrahydropyran]-2-one

To a stirred solution of Intermediate 43 (10.0 g, 25 mmol) in anhydrous DCM (100 mL) was added trifluoroacetic acid (18.56 mL, 250 mmol) portionwise over 2 minutes at r.t. The reaction mixture was stirred for a further 1 hour. The volatiles were removed in vacuo to give an oil which crystallized upon standing. Diethyl ether (50 mL) was added, and the mixture was sonicated until a fine crystalline solid developed. The solid was collected by filtration and washed with heptane (2×50 mL), then dried. The solid was triturated in a mixture of EtOAc (200 mL), saturated aqueous $NaHCO_3$ solution (100 mL) and 2M aqueous sodium hydroxide solution (20 mL) for 10 minutes. The solid was collected by filtration, rinsing the filter cake with water (2×50 mL), EtOAc (2×25 mL) and heptane (50 mL). The residue was dried in vacuo to afford the title compound (6.72 g, 90%) as a beige solid. $\delta_H$ (250 MHz, DMSO-$d_6$) 7.08 (dd, J 9.6, 1.6 Hz, 1H), 6.86 (d, J 1.6 Hz, 1H), 4.07 (t, J 10.6 Hz, 2H), 3.74 (dt, J 11.3, 3.7 Hz, 2H), 2.03 (ddd, J 15.0, 10.7, 4.6 Hz, 2H), 1.75-1.64 (m, 2H). $\delta_F$ (235 MHz, DMSO-$d_6$) −117.19. HPLC-MS (ES+) (method 15): MH+ m/z 300, RT 1.73 minutes.

Intermediate 45

6-Bromo-4-fluorospiro[indoline-3,4'-tetrahydropyran]

To a stirred suspension of Intermediate 44 (7.30 g, 24.3 mmol) in anhydrous THF (140 mL) was added 1M borane in THF (85 mL, 85.0 mmol) at r.t. After addition, the reaction mixture was heated under reflux for 1 h, then cooled to r.t. and quenched slowly with MeOH (40 mL). Stirring was continued for a further 10 minutes, then the mixture was concentrated in vacuo. The resulting yellow residue was partitioned between EtOAc (400 mL) and saturated aqueous $NaHCO_3$ solution (100 mL). The organic layer was collected, washed with water (100 mL) and brine (50 mL), then dried over anhydrous sodium sulfate, filtered and concentrated in vacuo, to afford the title compound (6.80 g, 98%) as a white solid. $\delta_H$ (250 MHz, DMSO-$d_6$) 6.48 (dd, J 9.6, 1.6 Hz, 1H), 6.43 (d, J 1.6 Hz, 1H), 6.24 (s, 1H), 3.79 (dd, J 11.6, 4.3 Hz, 2H), 3.52 (d, J 1.5 Hz, 2H), 3.40 (t, J 12.0 Hz, 2H), 2.04 (td, J 13.0, 4.8 Hz, 2H), 1.61-1.51 (m, 2H). $\delta_F$ (235 MHz, DMSO-$d_6$) −121.83. HPLC-MS (ES+) (method 6): MH+ m/z 286, RT 2.73 minutes.

Intermediate 46 tert-Butyl 6-bromo-4-fluorospiro[indoline-3,4'-tetrahydropyran]-1-carboxylate

To a stirred solution of Intermediate 45 (6.80 g, 23.8 mmol) in anhydrous THF (120 mL) was added di-tert-butyl dicarbonate (15.56 g, 71.3 mmol), followed by tert-butanol (5.0 mL, 52.3 mmol) and 4-(dimethylamino)pyridine (0.29 g, 2.38 mmol). The reaction mixture was heated at 50° C. for 16 h. A second aliquot of di-tert-butyl dicarbonate (5.19 g, 23.8 mmol) and tert-butanol (5.0 mL, 52.3 mmol) was added, and stirring was continued at 50° C. for 2 h. A third aliquot of di-tert-butyl dicarbonate (5.19 g, 23.8 mmol) was added, and stirring was continued at 60° C. for a further 3 h. The reaction mixture was cooled to r.t., and the solvent was concentrated in vacuo. The yellow residue was purified by flash column chromatography on silica, using a gradient of 5-20% tert-butyl methyl ether in heptane, to afford the title compound (8.34 g, 91%) as a white solid. $\delta_H$ (250 MHz, DMSO-$d_6$) 7.67 (s, 1H), 7.08 (dd, J 9.7, 1.6 Hz, 1H), 3.95 (s, 2H), 3.83 (dd, J 11.9, 4.2 Hz, 2H), 3.41 (t, J 12.3 Hz, 2H), 2.07 (td, J 13.0, 4.6 Hz, 2H), 1.61 (d, J 13.3 Hz, 2H), 1.52 (s, 9H). $\delta_F$ (235 MHz, DMSO-$d_6$) −119.85. HPLC-MS (ES+) (method 6): [M-$^t$Bu]+ m/z 330, RT 3.64 minutes.

Intermediate 47 tert-Butyl 6-amino-4-fluorospiro[indoline-3,4'-tetrahydropyran]-1-carboxylate

To a stirred solution of Intermediate 46 (7.3 g, 18.71 mmol) in anhydrous THF (124 mL) was added a 1M solution of lithium bis(trimethylsilyl)amide in THF (22.45 mL, 22.45 mmol). The reaction mixture was degassed by bubbling nitrogen gas through for 5 minutes, then Pd$_2$(dba)$_3$ (0.857 g, 0.94 mmol) and (2-biphenyl)dicyclohexylphosphine (0.79 g, 2.25 mmol) were added. The reaction mixture was stirred at 65° C. for 4.5 h, then cooled to r.t. A 1M solution of tetrabutylammonium fluoride in THF (58.4 mL, 58.4 mmol) was added. The mixture was stirred at r.t. for 25 minutes, then filtered through a pad of Kieselguhr. The filtrate was diluted with EtOAc (400 mL). The organic phase was washed with water (150 mL) and brine (2×100 mL), then dried over anhydrous sodium sulfate, filtered, and concentrated in vacuo. The crude residue was purified by flash column chromatography on silica, using a gradient of 5-100% tert-butyl methyl ether in heptane. The solvent was removed, then the residue was triturated in cyclohexane (20 mL), filtered and dried in vacuo, to afford the title compound (3.74 g, 62%) as an off-white solid. $\delta_H$ (250 MHz, DMSO-$d_6$) 6.83 (s, 1H), 5.90 (dd, J 12.9, 1.7 Hz, 1H), 5.33 (s, 2H), 3.82 (s, 2H), 3.80 (dd, J 11.2, 4.1 Hz, 2H), 3.37 (t, J 12.1 Hz, 2H), 2.04 (td, J 13.0, 4.5 Hz, 2H), 1.50 (s, 9H), 1.49-1.42 (m, 2H). $\delta_F$ (235 MHz, DMSO-$d_6$) −123.48. HPLC-MS (ES+) (method 6): MH+ m/z 323, RT 2.68 minutes.

Intermediate 48 tert-Butyl 6-{[(2S)-2-(benzyloxycarbonylamino)-2-(trans-4-methylcyclohexyl)acetyl]-amino}-4-fluorospiro[indoline-3,4'-tetrahydropyran]-1-carboxylate To a stirred solution of Intermediate 29 (306 mg, 0.70 mmol) in DMF (10 mL) were added Intermediate 47 (324 mg, 1.0 mmol), HATU (433 mg, 1.1 mmol) and DIPEA (276 µL, 1.59 mmol). The reaction mixture was stirred at r.t. for 21 h, then concentrated in vacuo and partitioned into DCM (10 mL) and saturated aqueous NaHCO$_3$ solution (10 mL). The phases were separated via a hydrophobic PTFE frit. The organic layer was concentrated in vacuo. The resulting crude material was purified by flash column chromatography on silica, using a gradient of 0-35% EtOAc in isohexane, then purified further by reverse-phase flash column chromatography, using a gradient of water in acetonitrile with 0.1% ammonium hydroxide additive (0-100%), to afford the title compound (169 mg, 34%) as a white solid. HPLC-MS (ES+) (method 6): MH+ m/z 610.4, RT 1.68 minutes.

Intermediate 49 tert-Butyl 6-{[(2S)-2-amino-2-(trans-4-methylcyclohexyl)acetyl]amino}-4-fluorospiro-[indoline-3,4'-tetrahydropyran]-1-carboxylate To a stirred solution of Intermediate 48 (292 mg, 0.48 mmol) in EtOAc (3 mL) was added palladium on carbon (54 mg, 0.05 mmol). The flask was evacuated, then filled with excess hydrogen gas. The reaction mixture was stirred at r.t. for 21 h, then filtered through a pre-packed Celite column. The column was washed with additional EtOAc (6 mL). The combined filtrate was concentrated in vacuo to afford the title compound (227 mg, 97%) as a greyish green solid. $\delta_H$ (400 MHz, DMSO-d) 7.79 (d, J 1.7 Hz, 1H), 7.22 (s, 1H), 3.91 (s, 2H), 3.83 (dd, J 11.7, 4.5 Hz, 2H), 3.41 (t, J 12.2 Hz, 2H), 3.06 (d, J 5.7 Hz, 1H), 2.08 (td, J 13.1, 4.8 Hz, 2H), 1.75-1.62 (m, 3H), 1.57 (d, J 13.4 Hz, 2H), 1.52 (s, 9H), 1.49-1.39 (m, 2H), 1.27-1.13 (m, 2H), 1.06-0.93 (m, 1H), 0.92-0.77 (m, 5H). HPLC-MS (ES+) (method 6): MH+ m/z 476.2, RT 1.50 minutes.

Intermediate 50 tert-Butyl 4-fluoro-6-{[(2S)-2-{[3-(methanesulfonamido)benzoyl]amino}-2-(trans-4-methylcyclohexyl) acetyl]amino}spiro[indoline-3,4'-tetrahydropyran]-1-carboxylate To a stirred solution of Intermediate 49 (41 mg, 0.084 mmol) in DCM (1.5 mL) were added 3-(methylsulfonamido)benzoic acid (21 mg, 0.096 mmol), HATU (41 mg, 0.11 mmol) and triethylamine (343 µL, 2.44 mmol). The reaction mixture was stirred at r.t. for 19 h, then concentrated in vacuo. The crude material was purified using flash column chromatography on silica, using a gradient of 0-70% EtOAc in isohexane, to afford the title compound (54 mg, 88%) as a colourless oil. HPLC-MS (ES+) (method 6): MH+ m/z 673.2, RT 1.51 minutes.

Intermediate 51 tert-Butyl 6-{[(2S)-2-[(4-ethyl-1,2,5-oxadiazole-3-carbonyl)amino]-2-(trans-4-methyl-cyclohexyl) acetyl]amino}-4-fluorospiro[indoline-3,4'-tetrahydropyran]-1-carboxylate To a stirred solution of Intermediate 49 (48 mg, 0.098 mmol) in DCM (2 mL) were added 4-ethyl-1,2,5-oxadiazole-3-carboxylic acid (16 mg, 0.11 mmol), HATU (55 mg, 0.14 mmol) and triethylamine (43 µL, 0.31 mmol). The reaction mixture was stirred at r.t. for 4 h, then diluted with DCM (6 mL) and washed with saturated aqueous NaHCO$_3$ solution (6 mL). The organic layer was separated and concentrated in vacuo. The resulting crude material was purified by flash column chromatography on silica, using a gradient of 0-40% EtOAc in isohexane, to afford the title compound (25 mg, 37%) as a white solid. HPLC-MS (ES+) (method 6): [M-$^t$Bu+H]+ m/z 544.2, RT 1.71 minutes.

Intermediate 52 tert-Butyl 6-{[(2S)-2-[(3-{[dimethyl(oxo)-$\lambda^6$-sulfanylidene]amino}benzoyl)amino]-2-(trans-4-methylcyclohexyl)acetyl]amino}-4-fluorospiro[indoline-3,4'-tetrahydropyran]-1-carboxylate To a stirred solution of Intermediate 49 (48 mg, 0.099 mmol) in DCM (2 mL) were added 3-{[dimethyl(oxo)-$\lambda^6$-sulfanylidene]amino}benzoic acid (23 mg, 0.11 mmol), HATU (52 mg, 0.13 mmol) and triethylamine (43 μL, 0.31 mmol). The reaction mixture was stirred at r.t. for 4 h, then diluted with DCM (6 mL) and washed with saturated aqueous NaHCO$_3$ solution (6 mL). The organic layer was concentrated in vacuo. The crude material was purified by flash column chromatography on silica, using a gradient of 0-100% EtOAc in isohexanes, to afford the title compound (53 mg, 80%) as a white solid. HPLC-MS (ES+) (method 6): MH+ m/z 671.2, RT 1.48 minutes.

Intermediate 53 tert-Butyl 6-{(2S)-2-[(1-ethyl-1H-pyrazol-5-yl)formamido]-2-(trans-4-methyl-cyclohexyl)acetamido}-4-fluoro-1,2-dihydrospiro[indole-3,4'-oxane]-1-carboxylate To a stirred solution of 1-ethyl-1H-pyrazole-5-carboxylic acid (47 mg, 0.34 mmol) and HATU (127 mg, 0.34 mmol) in DCM (2 mL) was added DIPEA (95 μL, 0.54 mmol). The reaction mixture was stirred at r.t. for 15 minutes, then Intermediate 49 (146 mg, 0.26 mmol) was added. The reaction mixture was stirred at r.t. for 18 h, then diluted with DCM (10 mL) and washed with saturated aqueous NaHCO$_3$ solution (5 mL) and water (5 mL). The organic layer was filtered through a hydrophobic PTFE frit, and concentrated in vacuo. The dark yellow residue was purified by flash column chromatography on silica, using a gradient of 0-75% tert-butyl methyl ether in heptane, to afford the title compound (140 mg, 84%) as a yellow oil. $\delta_H$ (250 MHz, CDCl$_3$) 7.79-7.63 (m, 1H), 7.61-7.51 (m, 1H), 7.47 (d, J 2.0 Hz, 1H), 6.67-6.59 (m, 1H), 6.58 (d, J 2.1 Hz, 1H), 4.58 (q, J 7.1 Hz, 2H), 4.45-4.33 (m, 1H), 4.03-3.94 (m, 2H), 3.91 (s, 2H), 3.59-3.42 (m, 2H), 2.47-2.28 (m, 2H), 1.85-1.71 (m, 4H), 1.58 (s, 9H), 1.51 (s, 1H), 1.43 (t, J 7.2 Hz, 3H), 1.37-1.22 (m, 3H), 1.17-0.94 (m, 4H), 0.89-0.86 (m, 3H). HPLC-MS (ES+) (method 3): MH+ m/z 598, RT 1.40 minutes.

Intermediate 54

(2S)-2-(tert-Butoxycarbonylamino)-2-(trans-4-methylcyclohexyl)acetic acid

To a stirred suspension of Intermediate 15 (25.1 g, 120.8 mmol) in water (350 mL) was added sodium carbonate (55 g, 0.52 mol), followed by di-tert-butyl dicarbonate (39.6 g, 181 mmol) in 1,4-dioxane (500 mL). The reaction mixture was mechanically stirred at r.t. for 4 h. The volatiles were removed in vacuo, then the suspension was cooled and 1N hydrochloric acid was carefully added to achieve a pH of 1. The mixture was extracted with EtOAc (3×250 mL). The organic layers were combined, and washed in turn with water (200 mL) and brine (200 mL), then filtered through phase separating paper and concentrated in vacuo. The resulting solid was triturated in heptane (500 mL) and filtered, then washed with heptane (2×100 mL) and oven-dried, to afford the title compound (28.8 g, 87%) as a white solid. $\delta_H$ (500 MHz, DMSO-d$_6$) 12.40 (s, 1H), 6.89 (d, J 8.5 Hz, 1H), 3.81-3.74 (m, 1H), 1.69-1.53 (m, 5H), 1.37 (s, 9H), 1.28-1.19 (m, 1H), 1.09 (dp, J 22.9, 12.6, 11.6 Hz, 2H), 0.91-0.76 (m, 5H). HPLC-MS (ES+) (method 1): MH+ m/z 271, RT 3.34 minutes. Chiral SFC (method 8, Chiralpak AS-H 25 cm, 10% methanol-90% CO$_2$, 4 mL/minute): RT 2.61 minutes (100%). $[\alpha]^2_0$ 28.3° (c 3.202, chloroform).

Intermediate 55 tert-Butyl N—{(S)-[(trans-4-methylcyclohexyl)(spiro[indene-1,4'-oxane]-5-yl)carbamoyl]-methyl}carbamate To a stirred solution of Intermediate 54 (166 mg, 0.61 mmol), Intermediate 21 (129 mg, 0.64 mmol) and HATU (279 mg, 0.73 mmol) in DCM (2 mL) was added DIPEA (0.21 mL, 1.28 mmol) at r.t. The reaction mixture was stirred at r.t. for 3 days, then diluted with DCM (10 mL) and washed with water (5 mL). The organic phase was separated, using a hydrophobic PTFE frit, and concentrated in vacuo. The resulting orange foam was purified by flash column chromatography on silica, using a gradient of 0-75% tert-butyl methyl ether in heptane, to afford the title compound (293 mg, 96%) as a cream foam. $\delta_H$ (250 MHz, CDCl$_3$) 7.85 (s, 1H), 7.65 (d, J 1.6 Hz, 1H), 7.33 (d, J 7.9 Hz, 1H), 7.28-7.23 (m, 1H), 6.98 (d, J 5.7 Hz, 1H), 6.76 (d, J 5.7 Hz, 1H), 5.22-5.00 (m, 1H), 4.17-4.04 (m, 2H), 4.03-3.94 (m, 1H), 3.88-3.70 (m, 2H), 2.28-2.08 (m, 2H), 1.95-1.68 (m, 5H), 1.48 (s, 9H), 1.34-1.26 (m, 3H), 1.20-0.94 (m, 4H), 0.90 (d, J 6.4 Hz, 3H). HPLC-MS (ES+) (method 3): MH+ m/z 455, RT 1.35 minutes.

Intermediate 56

(2S)-2-Amino-2-(trans-4-methylcyclohexyl)-N-(spiro[indene-1,4'-oxane]-5-yl)acetamide Trifluoroacetic acid (0.7 mL, 9.2 mmol) was added to a stirred solution of Intermediate 55 (293 mg, 0.61 mmol) in DCM (5 mL) at r.t. The reaction mixture was stirred for 22 h, then quenched with saturated aqueous NaHCO$_3$ solution (15 mL). DCM (10 mL) was added, and the phases were separated using a hydrophobic PTFE frit. The aqueous phase was extracted with DCM (2×10 mL). The combined organic phases were treated with saturated aqueous NaHCO$_3$ solution (10 mL), then separated using a hydrophobic PTFE frit and concentrated in vacuo, to afford the title compound (233 mg, 99%) as a yellow oil. $\delta_H$ (250 MHz, DMSO-d$_6$) 9.44 (s, 1H), 7.74-7.63 (m 1H), 7.43-7.29 (m, 2H), 7.12 (d, J 5.6 Hz, 1H), 6.80 (d, J 5.6 Hz, 1H), 5.76 (s, 2H), 4.04-3.85 (m, 2H), 3.83-3.61 (m, 2H), 3.10 (d, J 5.4 Hz, 1H), 2.12-2.00 (m, 2H), 1.79-1.41 (m, 6H), 1.29-0.92 (m, 6H), 0.85 (d, J 6.5 Hz, 3H). HPLC-MS (ES+) (method 3): MH+ m/z 355, RT 0.99 minutes.

Intermediate 57

2-[(6-Chloropyrrolo[3,2-c]pyridin-1-yl)methoxy]ethyl(trimethyl)silane

6-Chloro-1H-pyrrolo[3,2-c]pyridine (15 g, 98.30 mmol) was dissolved in anhydrous DMF (200 mL), then sodium hydride (60% dispersion in mineral oil, 4.7 g, 120 mmol) was added at 0° C. The solution was stirred for 1 h at 0° C., then 2-(trimethyl-silyl)ethoxymethyl chloride (22 mL, 117.83 mmol) was added. The reaction mixture was stirred at r.t. for 18 h, then diluted with EtOAc (100 mL) and washed with water (30 mL). The separated organic layer was dried with sodium sulfate, and concentrated in vacuo. The resulting crude oil was purified by flash column chromatography on silica, using a gradient of 0-100% EtOAc in heptane, to afford the title compound (27 g, 97%) as a white solid. HPLC-MS (ES+) (method 5): MH+ m/z 283.0, RT 1.21 minutes.

Intermediate 58

6-Chloro-1-[2-(trimethylsilyl)ethoxymethyl]-3H-pyrrolo[3,2-c]pyridin-2-one

To a stirred solution of Intermediate 57 (27 g, 95.47 mmol) in 1,4-dioxane (400 mL) was added pyridinium tribromide (135 g, 379.90 mmol) portionwise. The reaction mixture was stirred at r.t. for 2 h, then diluted with water (400 mL) and extracted with EtOAc (2×400 mL). The combined organic layers were washed with brine (3×500 mL), dried over sodium sulfate and concentrated in vacuo. The resulting crude 6-chloro-3,3-dibromo-1-[2-(trimethylsilyl)ethoxymethyl]pyrrolo[3,2-c]pyridin-2-one (56.5 g) was utilised without further purification.

To a stirred solution of crude 6-chloro-3,3-dibromo-1-[2-(trimethylsilyl)ethoxymethyl]pyrrolo[3,2-c]pyridin-2-one in THF (500 mL), cooled to 0° C., was added zinc powder (63 g, 943.89 mmol), followed by the dropwise addition of saturated aqueous ammonium chloride solution (160 mL). The reaction mixture was warmed to r.t. and stirred for 30 minutes, then filtered through celite, diluted with EtOAc (100 mL) and washed with brine (3×100 mL). The combined organic layer was concentrated in vacuo. The resulting crude oil was purified by flash column chromatography on silica, using a gradient of 0-50% EtOAc in isohexanes, to afford the title compound (10.5 g) as a yellow oil. The aqueous layer was filtered through celite and concentrated in vacuo, then purified by flash column chromatography on silica, using a gradient of 0-50% EtOAc in isohexanes, to afford additional title compound (1.9 g) as a yellow oil (combined amount 12.4 g, 43.5%). $\delta_H$ (300 MHz, DMSO-d) 8.17 (d, J 0.8 Hz, 1H), 7.23 (d, J 0.7 Hz, 1H), 5.10 (s, 2H), 3.75 (d, J 0.8 Hz, 2H), 3.63-3.47 (m, 2H), 1.18 (t, J 7.1 Hz, 1H), 0.95-0.80 (m, 1H), −0.06 (d, J 3.4 Hz, 9H). HPLC-MS (ES+) (method 5): MH+ m/z 299.0, RT 1.12 minutes.

Intermediate 59

6-Chloro-1-[2-(trimethylsilyl)ethoxymethyl]spiro[pyrrolo[3,2-c]pyridine-3,4'-tetrahydro-pyran]-2-one To a stirred solution of Intermediate 58 (4.3 g, 14 mmol) in anhydrous DMF (100 mL), cooled to 0° C., was added cesium carbonate (14 g, 42.92 mmol). The reaction mixture was stirred at 0° C. for 10 minutes, then 1-iodo-2-(2-iodoethoxy)ethane (4.3 mL, 29.00 mmol) was added dropwise at 0° C. The reaction mixture was stirred at r.t. for 18 h, then the solvent was removed in vacuo. The brown residue was dissolved in EtOAc (100 mL) and washed with brine (3×30 mL). The separated organic layer was dried with sodium sulfate, and concentrated in vacuo. The resulting crude oil was purified by flash column chromatography on silica, using a gradient of 0-100% EtOAc in isohexanes, to afford the title compound (3.6 g, 68%) as a red oil. HPLC-MS (ES+) (method 5): MH+m/z 369.0, RT 1.20 minutes.

Intermediate 60

6-Chlorospiro[pyrrolo[3,2-c]pyridine-3,4'-tetrahydropyran]-2-one

To a stirred solution of Intermediate 59 (4.6 g, 12 mmol) in DCM (50 mL) was added trifluoroacetic acid (20 mL, 264.50 mmol). The reaction mixture was stirred at r.t. for 18 h, then concentrated in vacuo. The residue was dissolved in EtOAc (100 mL) and washed twice with saturated aqueous NaHCO$_3$ solution (20 mL). The organic layer was concentrated in vacuo. The crude yellow solid was dissolved in acetonitrile (30 mL), and a solution of ammonia in water (5 mL, 60.6 mmol) was added. The reaction mixture was stirred at r.t. for 1 h, then concentrated in vacuo. The residue was dissolved in EtOAc (100 mL) and washed with water (20 mL). The separated organic layer was dried with sodium sulfate, then filtered and concentrated in vacuo, to afford the title compound (2.4 g, 81%) as a yellow solid. $\delta_H$ (400 MHz, DMSO-d$_6$) 11.10 (s, 1H), 8.56 (s, 1H), 7.32 (s, 1H), 4.01 (ddd, J 16.3, 7.1, 3.8 Hz, 2H), 3.84 (ddt, J 11.6, 7.5, 3.4 Hz, 2H), 1.79 (dddd, J 26.6, 16.6, 9.7, 4.2 Hz, 4H). HPLC-MS (ES+) (method 5): MH+ m/z 239.0, RT 0.87 minutes.

Intermediate 61

6-Chlorospiro[1,2-dihydropyrrolo[3,2-c]pyridine-3,4'-tetrahydropyran]

Intermediate 60 (1.7 g, 7.10 mmol) was dissolved in a solution of borane-THF complex in THF (60 mL) and heated at 70° C. for 2 h. The solution was cooled to r.t., then methanol (20 mL) was added. The reaction mixture was heated at reflux temperature for 2 h, then concentrated in vacuo. The resulting solid was filtered and dried under vacuum to afford the title compound (1.23 g, 75%) as a white solid. $\delta_H$ (400 MHz, DMSO-d$_6$) 7.79 (s, 1H), 6.89 (s, 1H), 6.34 (s, 1H), 3.81 (ddd, J 11.9, 4.4, 2.5 Hz, 2H), 3.55 (d, J 1.1 Hz, 2H), 3.45 (td, J 11.8, 2.3 Hz, 2H), 1.83 (ddd, J 13.4, 11.7, 4.6 Hz, 2H), 1.56 (dq, J 13.3, 2.4 Hz, 2H). HPLC-MS (ES+) (method 5): MH+ m/z 225.0, RT 0.97 minutes.

Intermediate 62

2-[(6-Chlorospiro[2H-pyrrolo[3,2-c]pyridine-3,4'-tetrahydropyran]-1-yl)methoxy]ethyl-(trimethyl)silane Intermediate 61 (1.23 g, 5.47 mmol) was dissolved in anhydrous DMF (15 mL) and DIPEA (1.9 mL, 11.00 mmol) was added, followed by 2-(trimethylsilyl)ethoxymethyl chloride (1.22 mL, 6.55 mmol). The reaction mixture was stirred at r.t. for 18 h, then diluted with EtOAc (50 mL) and washed with brine (10 mL). The separated organic layer was dried with sodium sulfate and concentrated in vacuo, then purified by flash column chromatography on silica, using a gradient of 0-100% EtOAc in isohexanes, to afford the title compound (1.4 g, 72%) as a white solid. $\delta_H$ (400 MHz, DMSO-d$_6$) 7.90 (s, 1H), 6.72 (s, 1H), 4.75 (s, 2H), 3.83 (ddd, J 12.0, 4.6, 2.3 Hz, 2H), 3.67 (s, 2H), 3.60-3.40 (m, 4H), 1.93-1.71 (m, 2H), 1.55 (dd, J 13.4, 2.1 Hz, 2H), 0.95-0.77 (m, 2H), −0.03 (s, 9H). HPLC-MS (ES+) (method 5): MH+ m/z 356.0, RT 1.61 minutes.

Intermediate 63

1-[2-(Trimethylsilyl)ethoxymethyl]spiro[2H-pyrrolo[3,2-c]pyridine-3,4'-tetrahydro-pyran]-6-amine Intermediate 62 (1.4 g, 3.90 mmol) was dissolved in THF (20 mL) and Pd$_2$(dba)$_3$ (190 mg, 0.20 mmol) and (2-biphenyl)dicyclohexylphosphine (170 mg, 0.47 mmol) were added, followed by a 1M solution of lithium bis(trimethylsilyl)amide in THF (4.7 mL, 4.70 mmol) at r.t. The resulting dark brown solution was heated at 70° C. for 5 h, then concentrated in vacuo. The crude oil was diluted with EtOAc (50 mL) and washed with brine (20 mL). The separated organic layer was dried with sodium sulfate, then concentrated in vacuo, to afford the title compound (1.6 g, 80% purity) as a brown solid. HPLC-MS (ES+) (method 5): MH+ m/z 336.0, RT 0.96 minutes.

Intermediate 64

Benzyl N-[(1S)-1-(trans-4-methylcyclohexyl)-2-oxo-2-({1-[2-(trimethylsilyl)ethoxymethyl]spiro[2H-pyrrolo[3,2-c]pyridine-3,4'-tetrahydropyran]-6-yl}amino)ethyl]-carbamate Intermediate 63 (80% purity, 450 mg, 1.34 mmol) was dissolved in DMF (6 mL), and Intermediate 29 (514 mg, 1.68 mmol), HATU (683 mg, 1.74 mmol) and DIPEA (1 mL, 5.75 mmol) were added. The reaction mixture was stirred at r.t. for 1 h, then diluted with EtOAc (100 mL) and washed with brine (20 mL). The separated organic layer was dried with sodium sulfate and concentrated in vacuo. The crude residue was purified by flash column chromatography on silica, using a gradient of 0-100% EtOAc in isohexanes, to afford the title compound (640 mg, 77%) as a brown oil. HPLC-MS (ES+) (method 5): MH+ m/z 623.0, RT 1.49 minutes.

Intermediate 65

(2S)-2-Amino-2-(trans-4-methylcyclohexyl)-N-{1-[2-(trimethylsilyl)ethoxymethyl]spiro-[2H-pyrrolo[3,2-c]pyridine-3,4'-tetrahydropyran]-6-yl}acetamide Intermediate 64 (640 mg, 1.3 mmol) was dissolved in ethanol (20 mL) and THF (20 mL), and palladium on carbon (10% mass, 500 mg) was added. The flask was evacuated, then filled with hydrogen gas and stirred at r.t. for 2 h. The reaction mixture was filtered through celite, and washed with methanol (20 mL). The organic layer was concentrated in vacuo to afford the title compound (700 mg) as a crude brown oil, which was utilised without further purification. HPLC-MS (ES+) (method 5): MH+ m/z 489.0, RT 1.40 minutes.

Intermediate 66

2-Ethyl-N-[(1S)-1-(trans-4-methylcyclohexyl)-2-oxo-2-({1-[2-(trimethylsilyl)ethoxymethyl]spiro[2H-pyrrolo[3,2-c]pyridine-3,4'-tetrahydropyran]-6-yl}amino)ethyl]-pyrazole-3-carboxamide Intermediate 65 (500 mg, 1.02 mmol) was dissolved in DCM (3 mL) and 1-ethyl-1H-pyrazole-5-carboxylic acid (225 mg, 1.52 mmol) and HATU (521 mg, 1.32 mmol) were added, followed by DIPEA (0.7 mL, 4.00 mmol). The reaction mixture was stirred at r.t. for 2 h, then washed with brine (3 mL). The separated organic layer was concentrated in vacuo. The crude residue was purified by flash column chromatography on silica, using a gradient of 0-100% EtOAc in isohexanes, to afford the title compound (83 mg, 13%) as a brown oil. HPLC-MS (ES+) (method 5): MH+ m/z 611.0, RT 1.74 minutes.

Example 1

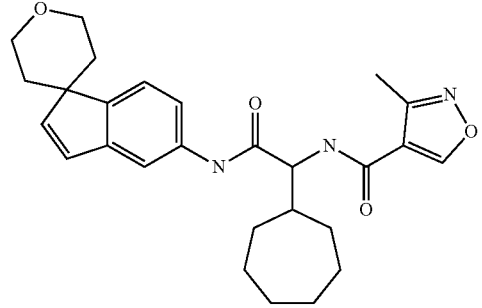 [SMILES: Cc1nocc1C(=O)NC(C(=O)Nc1ccc2c(c1)C=CC21CCOCC1)C1CCCCCC1]

2-Cyclooctyl-2-[(3-methylisoxazol-4-yl)formamido]-N-(spiro[indene-1,4'-oxane]-5-yl)-acetamide A tube was charged with EDC.HCl (70 mg, 0.37 mmol) and Intermediate 9 (108 mg, 0.37 mmol) in DCM (1.5 mL). The reaction mixture was stirred for 0.5 h at 20° C. The solvent was removed using a flow of nitrogen, then Intermediate 21 (50 mg, 0.24 mmol) in THF (1.5 mL) was added, followed by acetic acid (0.21 mL, 3.65 mmol). The tube was sealed, and the reaction mixture was heated at 60° C. for 1 h. After cooling, the reaction mixture was quenched with saturated aqueous sodium hydrogen carbonate solution (10 mL). The aqueous layer was extracted with EtOAc (2×20 mL). The combined organic extracts were washed with saturated aqueous sodium hydrogen carbonate solution (10 mL) and dried over sodium sulfate, then filtered and concentrated in vacuo. The resulting orange oil was separated by flash column chromatography on silica, using a gradient of EtOAc in heptane (0-50%). The resulting pale orange solid was triturated with DCM (3 mL) and filtered, then washed with DCM, to afford, after freeze-drying, the title compound (34 mg, 26%) as a white solid. δ$_H$ (500 MHz, CD$_3$OD) 9.02 (s, 1H), 7.51-7.47 (m, 1H), 7.28-7.23 (m, 2H), 6.97 (d, J 5.7 Hz, 1H), 6.67 (d, J 5.7 Hz, 1H), 4.42 (d, J 8.3 Hz, 1H), 3.99-3.90 (m, 2H), 3.77-3.65 (m, 2H), 2.34 (s, 3H), 2.17-2.01 (m, 3H), 1.75-1.64 (m, 3H), 1.63-1.51 (m, 4H), 1.50-1.35 (m, 7H), 1.18-1.11 (m, 2H). uPLC-MS (method 1): MH+ m/z 478, RT 3.94 minutes.

Example 2

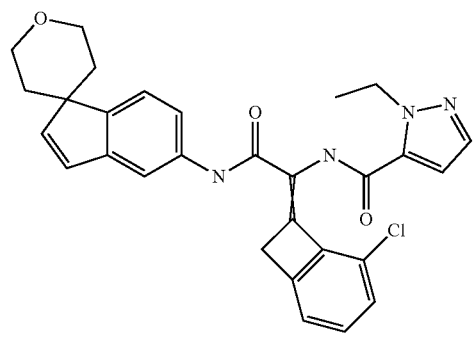 [SMILES: CCn1nccc1C(=O)NC(C(=O)Nc1ccc2c(c1)C=CC21CCOCC1)=C1Cc2cccc(Cl)c21]

2-(5-Chlorobicyclo[4.2.0]octa-1,3,5-trien-7-ylidene)-2-[(1-ethyl-1H-pyrazol-5-yl)-formamido]-N-(spiro[indene-1,4'-oxane]-5-yl)acetamide A tube was charged with Intermediate 4 (20 mg, 0.06 mmol) and Intermediate 21 (15 mg, 0.07 mmol) in THF (1 mL), followed by acetic acid (48.70 μL, 0.84 mmol). The tube was sealed, and the reaction mixture was heated for 3 h at 60° C. After cooling, the reaction mixture was concentrated in vacuo. The resulting orange foam was separated by flash column chromatography on silica, using a gradient of EtOAc in heptane (0-75%), to afford, after freeze-drying, the title compound (27 mg, 84%) as an off-white solid. $\delta_H$ (500 MHz, DMSO-$d_6$) 10.15 (s, 1H), 10.11 (s, 1H), 7.77 (d, J 1.7 Hz, 1H), 7.55 (d, J 1.9 Hz, 1H), 7.52-7.47 (m, 1H), 7.41 (d, J 8.1 Hz, 1H), 7.40-7.35 (m, 1H), 7.34-7.27 (m, 2H), 7.18-7.10 (m, 2H), 6.83 (d, J 5.6 Hz, 1H), 4.52 (q, J 7.1 Hz, 2H), 4.02-3.88 (m, 4H), 3.80-3.66 (m, 2H), 2.12-2.04 (m, 2H), 1.30 (t, J 7.1 Hz, 3H), 1.20-1.11 (m, 2H). uPLC-MS (method 1): MH+ m/z 515 and 517, RT 3.51 minutes.

Example 3

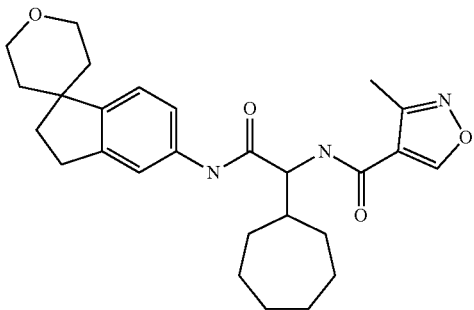 [SMILES: Cc1nocc1C(=O)NC(C(=O)Nc1ccc2c(c1)CCC21CCOCC1)C1CCCCCC1]

N-[1-Cyclooctyl-2-oxo-2-(spiro[indane-1,4'-tetrahydropyran]-5-ylamino)ethyl]-3-methyl-isoxazole-4-carboxamide A tube was charged with EDC.HCl (70.3 mg, 0.37 mmol) and Intermediate 9 (108 mg, 0.37 mmol) in DCM (1.5 mL). The reaction mixture was stirred for 1.5 h at 20° C. The solvent was removed using a flow of nitrogen, then Intermediate 22 (59 mg, 0.24 mmol) in THF (1.5 mL) was added, followed by acetic acid (0.21 mL, 3.65 mmol). The tube was sealed, and the reaction mixture was heated at 60° C. for 45 minutes. After cooling to r.t., the reaction mixture was quenched with saturated aqueous sodium hydrogen carbonate solution (10 mL). The aqueous layer was extracted with EtOAc (2×20 mL). The combined organic extracts were washed with saturated aqueous sodium hydrogen carbonate solution (10 mL) and dried over sodium sulfate, then filtered and concentrated in vacuo. The resulting orange oil was separated by flash column chromatography on silica, using a gradient of EtOAc in heptane (0-60%). The resulting pale yellow solid was further purified by trituration with DCM, then filtered and washed with DCM, to afford, after freeze drying, the title compound (44 mg, 34%) as a white solid. $\delta_H$ (500 MHz, DMSO-d) 10.11 (s, 1H), 9.43 (s, 1H), 8.45 (d, J 8.7 Hz, 1H), 7.55-7.50 (m, 1H), 7.40-7.36 (m, 1H), 7.15 (d, J 8.2 Hz, 1H), 4.47 (t, J 8.7 Hz, 1H), 3.88-3.78 (m, 2H), 3.58-3.46 (m, 2H), 2.84 (t, J 7.3 Hz, 2H), 2.38 (s, 3H), 2.14-2.02 (m, 3H), 1.85-1.77 (m, 2H), 1.73-1.61 (m, 3H), 1.59-1.45 (m, 7H), 1.44-1.31 (m, 6H). uPLC-MS (method 1): MH+ m/z 480, RT 4.03 minutes.

Example 4

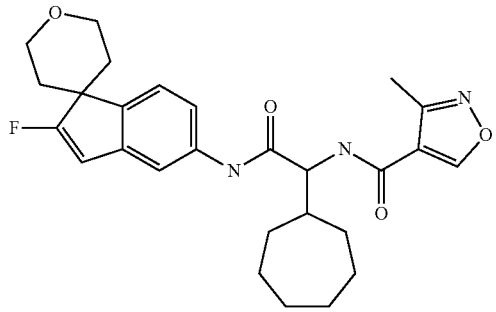 [SMILES: Cc1nocc1C(=O)NC(C(=O)Nc1ccc2c(c1)C=C(F)C21CCOCC1)C1CCCCCC1]

N-{1-Cyclooctyl-2-[(2-fluorospiro[indene-1,4'-tetrahydropyran]-5-yl)amino]-2-oxo-ethyl}-3-methyl-isoxazole-4-carboxamide A tube was charged with EDC.HCl (70 mg, 0.37 mmol) and Intermediate 9 (108 mg, 0.37 mmol) in DCM (1.5 mL). The reaction mixture was stirred for 0.5 h at 20° C. The solvent was removed using a flow of nitrogen, then Intermediate 25 (50 mg, 0.21 mmol) in THF (1.5 mL) was added, followed by acetic acid (0.18 mL, 3.16 mmol). The tube was sealed, and the reaction mixture was heated at 60° C. for 1 h. After cooling, the reaction mixture was quenched with saturated aqueous sodium hydrogen carbonate solution (10 mL). The aqueous layer was extracted with EtOAc (2×20 mL). The combined organic extracts were washed with saturated aqueous sodium hydrogen carbonate solution (10 mL) and dried over sodium sulfate, then filtered and concentrated in vacuo. The resulting pale brown solid was separated by flash column chromatography on silica, using a gradient of EtOAc in heptane (0-100%). The resulting off-white solid was triturated with DCM (3 mL), then filtered and washed with DCM, to afford, after freeze-drying, the title compound (41 mg, 38%) as a white solid. $\delta_H$ (500 MHz, CD$_3$OD) 9.14 (s, 1H), 7.55 (d, J 1.9 Hz, 1H), 7.45 (d, J 8.2 Hz, 1H), 7.35 (dd, J 8.2, 2.0 Hz, 1H), 6.10 (s, 1H), 4.53 (d, J 8.3 Hz, 1H), 4.08-4.02 (m, 2H), 4.01-3.94 (m, 2H), 2.46 (s, 3H), 2.26-2.17 (m, 1H), 1.97-1.88 (m, 2H), 1.85-1.75 (m, 5H), 1.74-1.56 (m, 8H), 1.55-1.50 (m, 3H). uPLC-MS (method 1): MH+ m/z 496, RT 4.06 minutes.

Example 5

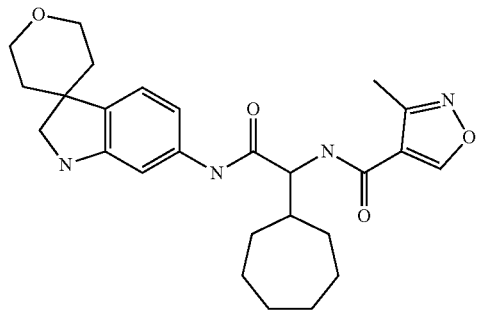 [SMILES: Cc1nocc1C(=O)NC(C(=O)Nc1ccc2c(c1)NCC21CCOCC1)C1CCCCCC1]

N-[1-Cyclooctyl-2-oxo-2-(spiro[indoline-3,4'-tetrahydropyran]-6-ylamino)ethyl]-3-methylisoxazole-4-carboxamide Trifluoroacetic acid (1 mL, 12.28 mmol) was added to a solution of Intermediate 28 (51 mg, 0.09 mmol) in DCM (2 mL) at 20° C. The reaction mixture was stirred at 20° C. for 1 h, then quenched with saturated aqueous sodium hydrogen carbonate solution (20 mL) and extracted with DCM (3×20 mL). The organic extracts were combined, filtered through a hydrophobic frit and concentrated in vacuo. The crude residue was purified by flash column chromatography on silica, using a gradient of tert-butyl methyl ether in heptane (0-100%), followed by a gradient of methanol in tert-butyl methyl ether (0-20%), to afford, after freeze drying, the title compound (14 mg, 37%) as a white solid. $\delta_H$ (500 MHz, CDCl$_3$) 8.68 (s, 1H), 7.63 (s, 1H), 6.96-6.90 (m, 2H), 6.60 (dd, J 7.9, 1.9 Hz, 1H), 6.57 (d, J 8.7 Hz, 1H), 4.37 (t, J 8.1 Hz, 1H), 3.92-3.84 (m, 2H), 3.84-3.64 (m, 1H), 3.50-3.41 (m, 4H), 2.43 (s, 3H), 2.13-2.03 (m, 1H), 1.91-1.80 (m, 2H), 1.72-1.52 (m, 7H), 1.44-1.27 (m 9H). uPLC-MS (method 1): MH+ m/z 481.3, RT 2.96 minutes.

Example 6

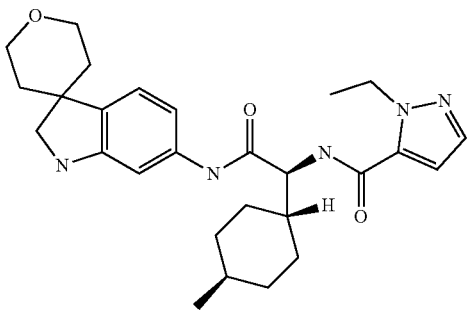 [SMILES: CCn1nccc1C(=O)N[C@H](C(=O)Nc1ccc2c(c1)NCC21CCOCC1)[C@H]1CC[C@H](C)CC1]

2-Ethyl-N-[(1S)-1-(4-methylcyclohexyl)-2-oxo-2-(spiro[indoline-3,4'-tetrahydropyran]-6-ylamino)ethyl]pyrazole-3-carboxamide (trans isomer)

Trifluoroacetic acid (3.81 mL, 46.75 mmol) was added to a solution of Intermediate 32 (211 mg, 0.33 mmol) in DCM (7.5 mL) at 20° C. The reaction mixture was stirred at 20° C. for 1 h, then quenched with saturated aqueous sodium hydrogen carbonate solution (30 mL) and extracted with DCM (3×30 mL). The organic extracts were combined, filtered through a hydrophobic frit and concentrated in vacuo. The crude residue was purified by flash column chromatography on silica, using a gradient of methanol in tert-butyl methyl ether (0-20%). The resulting impure material was purified further by preparative HPLC (method 13), and the relevant fractions were combined and extracted with EtOAc (3×50 mL). The organic extracts were combined, washed with brine (20 mL) and dried over sodium sulfate, then filtered and concentrated in vacuo. The resulting pink solid was dissolved in DCM (2 mL) and ethanol (2 mL). The solution was treated with hydrochloric acid (aqueous solution, 12M, 1 mL) and stirred at 20° C. for 18 h, then quenched with saturated aqueous sodium hydrogen carbonate solution (30 mL) and extracted with DCM (3×20 mL). The organic extracts were combined and filtered through a hydrophobic frit, then concentrated in vacuo and freeze-dried, to afford the title compound (95 mg, 71%) as an off-white solid. $\delta_H$ (500 MHz, DMSO-d$_6$) 9.98 (s, 1H), 8.44 (d, J 8.2 Hz, 1H), 7.47 (d, J 2.0 Hz, 1H), 7.12 (s, 1H), 7.06-6.99 (m, 2H), 6.93-6.83 (m, 1H), 4.46 (q, J 7.1 Hz, 2H), 4.34 (t, J 8.6 Hz, 1H), 3.82 (d, J 10.1 Hz, 2H), 3.49-3.43 (m, 4H), 1.88-1.64 (m, 6H), 1.57 (d, J 12.8 Hz, 1H), 1.50 (d, J 12.7 Hz, 2H), 1.33-1.23 (m, 4H), 1.23-1.13 (m, 1H), 1.08-0.96 (m, 1H), 0.93-0.79 (m, 5H). uPLC-MS (method 1): MH+ m/z 480.2, RT 2.84 minutes.

Example 7

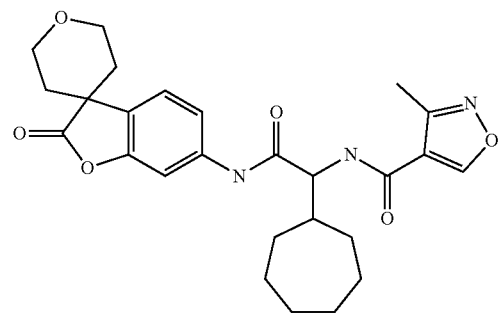 [SMILES: Cc1nocc1C(=O)NC(C(=O)Nc1ccc2c(c1)OC(=O)C21CCOCC1)C1CCCCCC1]

N-{1-Cyclooctyl-2-oxo-2-[(2-oxo-2',3',5',6'-tetrahydro-2H-spiro[benzofuran-3,4'-pyran]-6-yl)amino]ethyl}-3-methylisoxazole-4-carboxamide To a solution of Intermediate 38 (0.12 g, 0.55 mmol) and Intermediate 9 (0.16 g, 0.55 mmol) in DCM (10 mL) was added propylphosphonic anhydride (50% solution in EtOAc) (0.24 mL, 0.82 mmol), followed by the addition of triethylamine (0.24 mL, 1.64 mmol) at 0° C. The reaction mixture was stirred at r.t. for 16 h, then diluted with DCM (20 mL) and washed with water (10 mL) and brine (10 mL). The organic layer was separated, dried over anhydrous Na$_2$SO$_4$ and concentrated in vacuo. The crude residue was purified by preparative HPLC (method 7) to afford the title compound (0.015 g, 6%) as a white solid. $\delta_H$ (400 MHz, DMSO-d$_6$) 1.36-1.59 (m, 12H), 1.62-1.73 (m, 2H), 1.85-1.88 (m, 4H), 2.06-2.14 (m, 1H), 2.37 (s, 3H), 3.80-3.87 (m, 2H), 3.88-3.98 (m, 2H), 4.47 (t, J 8.56 Hz, 1H), 7.34 (dd, J 8.31, 1.47 Hz, 1H), 7.58 (d, J 8.31 Hz, 1H), 7.66 (d, J 1.96 Hz, 1H), 8.52 (d, J 8.80 Hz, 1H), 9.43 (s, 1H), 10.46 (s, 1H). HPLC-MS (method 5): MH+ m/z 494.0, RT 3.10 minutes.

Example 8

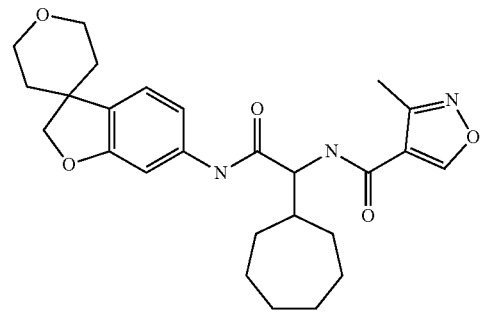 [SMILES: Cc1nocc1C(=O)NC(C(=O)Nc1ccc2c(c1)OCC21CCOCC1)C1CCCCCC1]

N-[1-Cyclooctyl-2-oxo-2-(spiro[2H-benzofuran-3,4'-tetrahydropyran]-6-ylamino)ethyl]-3-methylisoxazole-4-carboxamide To a solution of Intermediate 41 (0.05 g, 0.24 mmol) in THF (2 mL) was added Intermediate 9 (0.08 g, 0.27 mmol), followed by the addition of propylphosphonic anhydride (50% solution in EtOAc) (0.72 mL, 2.44 mmol). The reaction mixture was heated at 60° C. for 12 h, then concentrated in vacuo. The crude residue was purified by column chromatography on silica (15% EtOAc in hexanes), followed by SFC purification (method 8, using a silica-2-ethylpyridine 250×30 mm, 5 μm column, eluting with 0.1% $NH_3$ in methanol/$CO_2$, flow 80.0 mL/minute), to afford the title compound (0.04 g, 34%) as a white solid. $\delta_H$ (400 MHz, DMSO-$d_6$) 1.33-1.35 (m, 3H), 1.42-1.45 (m, 3H), 1.49-1.53 (m, 5H), 1.60-1.64 (m, 3H), 1.78-1.85 (m, 2H), 2.02-2.05 (m, 1H), 2.33 (s, 3H), 3.35-3.41 (m, 2H), 3.80 (d, J 11.3 Hz, 2H), 4.37-4.46 (m, 3H), 7.01 (d, J 7.9 Hz, 1H), 7.13 (d, J 7.9 Hz, 1H) 7.17 (d, J 1.0 Hz, 1H), 8.44 (d, J 8.9 Hz, 1H), 9.40 (s, 1H), 10.15 (s, 1H) (2H submerged in solvent peak). HPLC-MS (method 11): MH+ m/z 482.0, RT 2.99 minutes.

Example 9

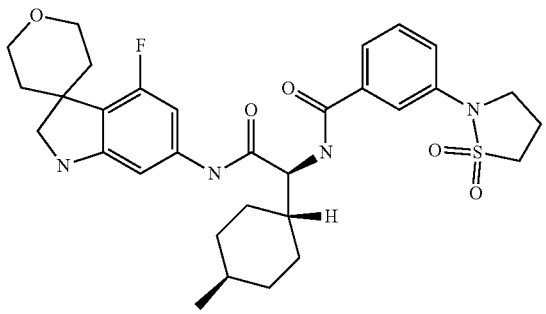 [SMILES: C[C@H]1CC[C@H]([C@H](NC(=O)c2cccc(N3CCCS3(=O)=O)c2)C(=O)Nc2cc(F)c3c(c2)NCC32CCOCC2)CC1]

3-(1,1-Dioxo-1,2-thiazolidin-2-yl)-N-{(1S)-2-[(4-fluorospiro[indoline-3,4'-tetrahydro-pyran]-6-yl)amino]-1-(trans-4-methylcyclohexyl)-2-oxoethyl}benzamide To a stirred solution of Intermediate 49 (38 mg, 0.077 mmol) in DCM (1.5 mL) were added 3-(1,1-dioxo-1,2-thiazolidin-2-yl)benzoic acid (21 mg, 0.088 mmol), HATU (45 mg, 0.12 mmol) and triethylamine (32 μL, 0.23 mmol). The reaction mixture was stirred at r.t. for 2 h, then diluted with DCM (10 mL) and washed with water (10 mL). The separated organic phase was concentrated in vacuo. The resulting crude material was re-dissolved in DCM (1 mL), and trifluoroacetic acid (146 μL, 1.91 mmol) was added. The reaction mixture was stirred for 6 h at r.t., then diluted with DCM (10 mL) and quenched with saturated aqueous $NaHCO_3$ solution (10 mL). The phases were separated via a hydrophobic PTFE frit. The organic layer was concentrated in vacuo. The resulting crude material was purified by preparative HPLC (method 21) to afford the title compound (19 mg, 41%) as a white solid. $\delta_H$ (400 MHz, DMSO-$d_6$) 10.04 (s, 1H), 8.53 (d, J 8.1 Hz, 1H), 7.66 (dt, J 7.7, 1.3 Hz, 1H), 7.63-7.61 (m, 1H), 7.46 (t, J 7.9 Hz, 1H), 7.39 (ddd, J 8.2, 2.4, 1.1 Hz, 1H), 6.67 (dd, J 12.5, 1.6 Hz, 1H), 6.62 (d, J 1.6 Hz, 1H), 6.00 (s, 1H), 4.35 (t, J 8.6 Hz, 1H), 3.85-3.74 (m, 4H), 3.53 (t, J 7.4 Hz, 2H), 3.46 (d, J 1.8 Hz, 2H), 3.40 (t, J 12.1 Hz, 2H), 2.42 (p, J 6.9 Hz, 2H), 2.10-1.99 (m, 2H), 1.90-1.73 (m, 2H), 1.72-1.64 (m, 2H), 1.59-1.49 (m, 3H), 1.35-1.25 (m, 2H), 1.22-1.12 (m, 1H), 1.09-0.96 (m, 1H), 0.93-0.77 (m, 5H). uPLC-MS (method 17): MH+ m/z 599.4, RT 2.01 minutes.

Example 10

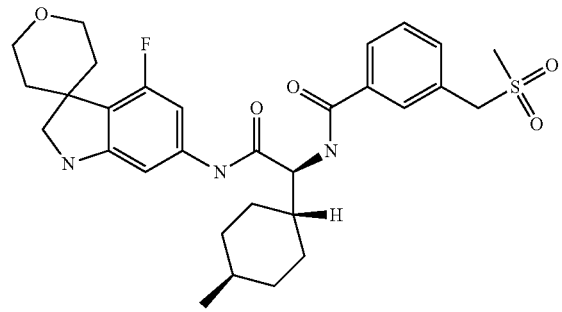 [SMILES: CS(=O)(=O)Cc1cccc(C(=O)N[C@H](C(=O)Nc2cc(F)c3c(c2)NCC32CCOCC2)[C@H]2CC[C@H](C)CC2)c1]

N-{(1S)-2-[(4-Fluorospiro[indoline-3,4'-tetrahydro-pyran]-6-yl)amino]-1-(trans-4-methyl-cyclohexyl)-2-oxoethyl}-3-(methylsulfonylmethyl)benzamide To a stirred solution of Intermediate 49 (38 mg, 0.077 mmol) in DCM (1.5 mL) were added 3-(methylsulfonylmethyl)benzoic acid (20 mg, 0.088 mmol), HATU (41 mg, 0.11 mmol) and triethylamine (32 μL, 0.23 mmol). The reaction mixture was stirred at r.t. for 2 h, then diluted with DCM (10 mL) and washed with water (10 mL). The separated organic phase was concentrated in vacuo. The resulting crude material was dissolved in DCM (1 mL), and trifluoroacetic acid (146 μL, 1.91 mmol) was added. The reaction mixture was stirred for 6 h at r.t., then diluted with DCM (10 mL) and quenched with saturated aqueous $NaHCO_3$ solution (10 mL). The phases were separated via a hydrophobic PTFE frit. The organic layer was concentrated in vacuo. The resulting crude material was purified by preparative HPLC (method 21) to afford the title compound (15 mg, 34%) as a white solid. $\delta_H$ (400 MHz, DMSO-$d_6$) 10.04 (s, 1H), 8.50 (d, J 8.1 Hz, 1H), 7.96-7.87 (m, 2H), 7.57 (dt, J 7.7, 1.5 Hz, 1H), 7.50 (t, J 7.6 Hz, 1H), 6.67 (dd, J 12.5, 1.6 Hz, 1H), 6.62 (d, J 1.6 Hz, 1H), 6.00 (s, 1H), 4.55 (s, 2H), 4.37 (t, J 8.5 Hz, 1H), 3.79 (dd, J 11.7, 4.3 Hz, 2H), 3.46 (d, J 1.8 Hz, 2H), 3.40 (t, J 12.1 Hz, 2H), 2.93 (s, 3H), 2.11-1.97 (m, 2H), 1.92-1.74 (m, 2H), 1.72-1.64 (m, 2H), 1.60-1.49 (m, 3H), 1.28 (s, 1H), 1.22-1.11 (m, 1H), 1.09-0.97 (m, 1H), 0.93-0.79 (m, 5H). uPLC-MS (method 17): MH+ m/z 572.2, RT 1.90 minutes.

Example 11

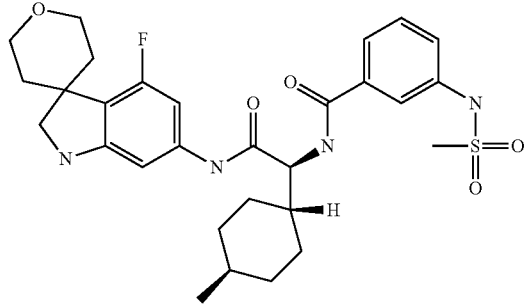 [SMILES: CS(=O)(=O)Nc1cccc(C(=O)N[C@H](C(=O)Nc2cc(F)c3c(c2)NCC32CCOCC2)[C@H]2CC[C@H](C)CC2)c1]

N-{(1S)-2-[(4-Fluorospiro[indoline-3,4'-tetrahydro-pyran]-6-yl)amino]-1-(trans-4-methyl-cyclohexyl)-2-oxoethyl}-3-(methanesulfonamido)benzamide To a stirred solution of Intermediate 50 (54 mg, 0.074 mmol) in DCM (1.5 mL) was added trifluoroacetic acid (170 μL, 2.22 mmol). The reaction mixture was stirred for 2.5 h at r.t., then diluted with DCM (6 mL) and quenched with saturated aqueous $NaHCO_3$ solution (6 mL). The separated organic layer was concentrated in vacuo. The crude material was purified by preparative HPLC (method 7) to afford the title compound (21 mg, 47%) as a white solid. δ$_H$ (400 MHz, DMSO-d$_6$) 10.03 (s, 1H), 9.87 (s, 1H), 8.46 (d, J 8.2 Hz, 1H), 7.68-7.60 (m, 2H), 7.46-7.34 (m, 2H), 6.70-6.60 (m, 2H), 6.00 (s, 1H), 4.34 (t, J 8.5 Hz, 1H), 3.80 (dd, J 11.3, 4.1 Hz, 2H), 3.47 (s, 2H), 3.41 (t, J 12.1 Hz, 2H), 3.00 (s, 3H), 2.11-2.00 (m, 2H), 1.91-1.74 (m, 2H), 1.73-1.64 (m, 2H), 1.54 (d, J 12.9 Hz, 3H), 1.34-1.25 (m, 1H), 1.18 (qd, J 12.8, 2.8 Hz, 1H), 1.10-0.97 (m, 1H), 0.94-0.78 (m, 5H). uPLC-MS (method 17): MH+ m/z 573.0, RT 1.63 minutes.

Example 12

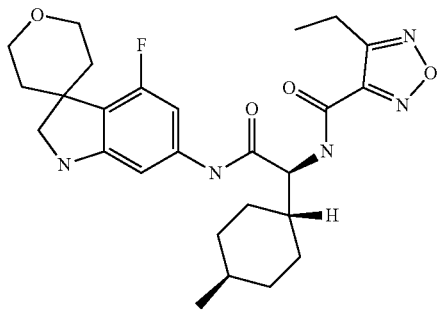 [SMILES: CCc1nonc1C(=O)N[C@H](C(=O)Nc1cc(F)c2c(c1)NCC21CCOCC1)[C@H]1CC[C@H](C)CC1]

4-Ethyl-N-{(1S)-2-[(4-fluorospiro[indoline-3,4'-tetrahydropyran]-6-yl)amino]-1-(trans-4-methylcyclohexyl)-2-oxoethyl}-1,2,5-oxadiazole-3-carboxamide To a stirred solution of Intermediate 51 (25 mg, 0.036 mmol) in DCM (0.7 mL) was added trifluoroacetic acid (210 μL, 2.7 mmol). The reaction mixture was stirred for 20 h at r.t., then diluted with DCM (6 mL) and quenched with saturated aqueous NaHCO$_3$ solution (6 mL). The separated organic layer was concentrated in vacuo. The crude material was purified by preparative HPLC (method 7) to afford the title compound (8 mg, 44%) as a white solid. δ$_H$ (400 MHz, DMSO-d$_6$) 10.08 (s, 1H), 9.12 (d, J 8.2 Hz, 1H), 6.67-6.58 (m, 2H), 6.02 (s, 1H), 4.39 (t, J 8.2 Hz, 1H), 3.84-3.74 (m, 2H), 3.50-3.44 (m, 2H), 3.40 (t, J 12.1 Hz, 2H), 2.88 (q, J 7.5 Hz, 2H), 2.11-1.98 (m, 2H), 1.84-1.72 (m, 2H), 1.72-1.63 (m, 2H), 1.61-1.48 (m, 3H), 1.32-1.26 (m, 1H), 1.23 (t, J 7.5 Hz, 3H), 1.20-1.11 (m, 1H), 1.04 (qd, J 12.6, 12.0, 2.8 Hz, 1H), 0.85 (t, J 7.0 Hz, 5H). uPLC-MS (method 16): MH+ m/z 500.0, RT 2.67 minutes.

Example 13

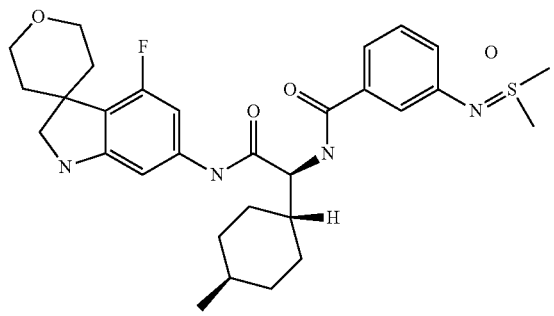

3-{[Dimethyl(oxo)-λ$^6$-sulfanylidene]amino}-N-{(1S)-2-[(4-fluorospiro[indoline-3,4'-tetrahydropyran]-6-yl)amino]-1-(trans-4-methylcyclohexyl)-2-oxoethyl}benzamide To a stirred solution of Intermediate 52 (53 mg, 0.079 mmol) in DCM (1.5 mL) was added trifluoroacetic acid (300 μL, 3.9 mmol). The reaction mixture was stirred for 7 h at r.t., then diluted with DCM (10 mL) and quenched with saturated aqueous NaHCO$_3$ solution (6 mL). The separated organic layer was concentrated in vacuo. The resulting crude material was purified by preparative HPLC (method 7) to afford the title compound (13 mg, 29%) as a white solid. δ$_H$ (400 MHz, DMSO-d$_6$) 9.98 (s, 1H), 8.32 (d, J 8.1 Hz, 1H), 7.42-7.36 (m, 2H), 7.26 (t, J 8.0 Hz, 1H), 7.08 (ddd, J 7.9, 2.2, 1.1 Hz, 1H), 6.66 (dd, J 12.5, 1.6 Hz, 1H), 6.62 (d, J 1.6 Hz, 1H), 5.99 (s, 1H), 4.31 (t, J 8.5 Hz, 1H), 3.79 (dd, J 11.7, 4.2 Hz, 2H), 3.49-3.44 (m, 2H), 3.40 (t, J 12.2 Hz, 2H), 3.22 (d, J 1.9 Hz, 6H), 2.10-1.98 (m, 2H), 1.90-1.74 (m, 2H), 1.72-1.62 (m, 2H), 1.53 (d, J 12.9 Hz, 3H), 1.34-1.23 (m, 1H), 1.16 (qd, J 12.8, 12.3, 3.1 Hz, 1H), 1.00 (s, 1H), 0.93-0.78 (m, 5H). uPLC-MS (method 16) MH+ m/z 571.0, RT 2.11 minutes.

Example 14

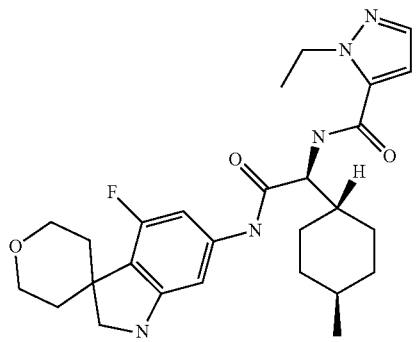 [SMILES: CCn1nccc1C(=O)N[C@H](C(=O)Nc1cc(F)c2c(c1)NCC21CCOCC1)[C@H]1CC[C@H](C)CC1]

(2S)-2-[(1-Ethyl-1H-pyrazol-5-yl)formamido]-N-(4-fluoro-1,2-dihydrospiro[indole-3,4'-oxane]-6-yl)-2-(trans-4-methylcyclohexyl)acetamide Trifluoroacetic acid (1 mL, 13.46 mmol) was added to a stirred solution of Intermediate 53 (140.0 mg, 0.22 mmol) in DCM (2 mL) at r.t. The reaction mixture was stirred for 1 h, then quenched with saturated aqueous NaHCO$_3$ solution (10 mL) and extracted with DCM (2×10 mL). The combined organic phases were filtered through a hydrophobic PTFE frit, and concentrated in vacuo. The residue was purified by preparative HPLC (method 19). The combined fractions were adjusted to pH 8 with saturated aqueous NaHCO$_3$ solution, and extracted with DCM (1×50 mL, then 2×10 mL). The combined organic phases were washed with saturated aqueous NaHCO$_3$ solution (10 mL) and brine (10 mL), then dried over sodium sulfate, filtered and concentrated in vacuo, to afford the title compound (70 mg, 65%) as a white solid. δ$_H$ (500 MHz, DMSO-d$_6$) 10.01 (s, 1H), 8.45 (d, J 8.1 Hz, 1H), 7.51-7.42 (m, 1H), 7.04-6.95 (m, 1H), 6.65 (dd, J 12.4, 1.5 Hz, 1H), 6.62 (d, J 1.6 Hz, 1H), 5.99 (s, 1H), 4.45 (q, J 7.2 Hz, 2H), 4.34-4.25 (m, 1H), 3.84-3.74 (m, 2H), 3.48-3.44 (m, 2H), 3.43-3.37 (m, 2H), 2.11-1.97 (m, 2H), 1.87-1.79 (m, 1H), 1.79-1.63 (m, 3H), 1.59-1.49 (m, 3H), 1.31-1.23 (m, 4H), 1.20-1.10 (m, 1H), 1.06-0.96 (m, 1H), 0.92-0.79 (m, 5H). uPLC-MS (method 1): MH+ m/z 498, RT 3.52 minutes.

Example 15

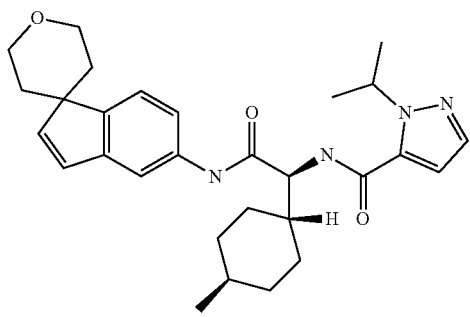 [SMILES: CC(C)n1nccc1C(=O)N[C@H](C(=O)Nc1ccc2c(c1)C=CC21CCOCC1)[C@H]1CC[C@H](C)CC1]

(2S)-2-{[1-(Propan-2-yl)-1H-pyrazol-5-yl]formamido}-2-(trans-4-methylcyclohexyl)-N-(spiro[indene-1,4'-oxane]-5-yl)acetamide DIPEA (94 µL, 0.57 mmol) was added to a stirred solution of Intermediate 56 (70 mg, 0.19 mmol), 1-(propan-2-yl)-1H-pyrazole-5-carboxylic acid (44 mg, 0.28 mmol) and HATU (112 mg, 0.29 mmol) in DCM (2.5 mL) at r.t. The reaction mixture was stirred at r.t. for 18 h, then diluted with water (5 mL) and extracted with DCM (3×15 mL). The combined organic phases were separated using a hydrophobic PTFE frit, and concentrated in vacuo. The residue was purified by flash column chromatography on silica, using a gradient of tert-butyl methyl ether in heptane (0-80%), to afford the title compound (61 mg, 65%) as a white solid. $\delta_H$ (250 MHz, DMSO-d) 10.12 (s, 1H), 8.45 (d, J 8.2 Hz, 1H), 7.70-7.66 (m, 1H), 7.50 (d, J 1.9 Hz, 1H), 7.43-7.33 (m, 2H), 7.12 (d, J 5.6 Hz, 1H), 6.95 (d, J 2.0 Hz, 1H), 6.81 (d, J 5.7 Hz, 1H), 5.44-5.34 (m, 1H), 4.37 (t, J 8.5 Hz, 1H), 3.99-3.90 (m, 2H), 3.77-3.67 (m, 2H), 2.11-2.01 (m, 2H), 1.91-1.75 (m, 2H), 1.74-1.65 (m, 2H), 1.63-1.56 (m, 1H), 1.37 (d, J 6.6 Hz, 3H), 1.34 (d, J 6.6 Hz, 3H), 1.32-1.26 (m, 1H), 1.25-1.18 (m, 1H), 1.16-1.10 (m, 2H), 1.10-1.01 (m, 1H), 0.92-0.81 (m, 5H). uPLC-MS (method 1): MH+ m/z 491, RT 4.06 minutes.

Example 16

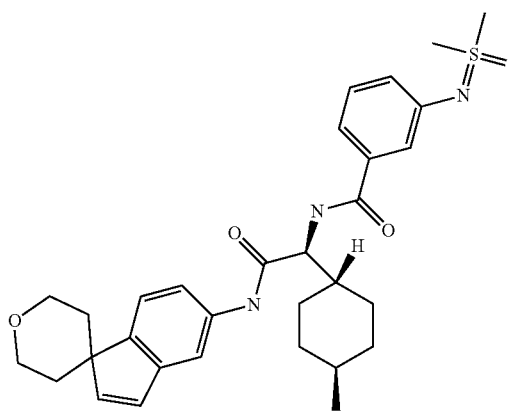

3-{[Dimethyl(oxo)-$\lambda^6$-sulfanylidene]amino}-N-[(1S)-1-(trans-4-methylcyclohexyl)-2-oxo-2-(spiro[indene-1,4'-tetrahydropyran]-5-ylamino)ethyl]benzamide 3-{[Dimethyl(oxo)-$\lambda^6$-sulfanylidene]amino}benzoic acid (53 mg, 0.25 mmol) was added to a stirred suspension of HATU (103 mg, 0.27 mmol) and DIPEA (0.15 mL, 0.90 mmol) in DCM (2 mL). The mixture was stirred at r.t. for 30 minutes, then a solution of Intermediate 56 (80 mg, 0.23 mmol) in DCM (1 mL) was added. The reaction mixture was stirred at r.t. for 3 days, then partitioned between DCM (20 mL) and water (20 mL). The aqueous layer was separated and washed with DCM (2×20 mL). The combined organic phases were washed with brine (20 mL) and dried over magnesium sulfate, then filtered and concentrated in vacuo. The residue was purified by flash column chromatography on silica, using a gradient of MeOH in DCM (0-20%), then preparative HPLC (method 18), to afford the title compound (65 mg, 52%) as a white solid. $\delta_H$ (500 MHz, DMSO-d) 10.08 (s, 1H), 8.32 (d, J 8.2 Hz, 1H), 7.67 (s, 1H), 7.43-7.39 (m, 2H), 7.39-7.35 (m, 2H), 7.26 (t, J 8.0 Hz, 1H), 7.11 (d, J 5.6 Hz, 1H), 7.09 (ddd, J 8.0, 2.1, 1.0 Hz, 1H), 6.79 (d, J 5.7 Hz, 1H), 4.38 (t, J 8.5 Hz, 1H), 3.98-3.89 (m, 2H), 3.71 (td, J 11.6, 1.7 Hz, 2H), 3.23 (s, 3H), 3.22 (s, 3H), 2.05 (td, J 12.9, 4.1 Hz, 2H), 1.91-1.85 (m, 1H), 1.85-1.77 (m, 1H), 1.73-1.64 (m, 2H), 1.60 (d, J 12.5 Hz, 1H), 1.35-1.25 (m, 1H), 1.20 (qd, J 13.0, 3.4 Hz, 1H), 1.13 (d, J 12.5 Hz, 2H), 1.04 (qd, J 12.6, 2.8 Hz, 1H), 0.93-0.87 (m 1H), 0.87-0.82 (m 4H). uPLC-MS (method 1): MH+ m/z 550, RT 3.46 minutes.

Example 17

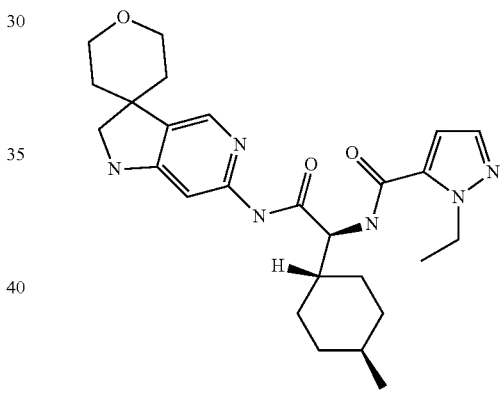

2-Ethyl-N-[(1S)-1-(trans-4-methylcyclohexyl)-2-oxo-2-(spiro[1,2-dihydropyrrolo[3,2-c]-pyridine-3,4'-tetrahydropyran]-6-ylamino)ethyl]pyrazole-3-carboxamide Intermediate 66 (83 mg, 0.13 mmol) was dissolved in DCM (1 mL), and trifluoroacetic acid (0.1 mL) was added. The reaction mixture was stirred at r.t. for 2 h, then concentrated in vacuo. The residue was dissolved in acetonitrile (2 mL), and a solution of ammonia in water (0.1 mL, 1.00 mmol) was added. The reaction mixture was stirred at r.t. for 1 h, then concentrated in vacuo and purified by preparative HPLC (method 21), to afford the title compound (4 mg, 6%) as a white solid. $\delta_H$ (400 MHz, DMSO-$d_6$) 10.07 (s, 1H), 8.40 (d, J 8.2 Hz, 1H), 7.76 (s, 1H), 7.48 (d, J 2.0 Hz, 1H), 7.22 (s, 1H), 6.97 (d, J 2.0 Hz, 1H), 6.60 (d, J 4.9 Hz, 1H), 4.52-4.35 (m, 3H), 3.81 (dt, J 11.6, 3.6 Hz, 2H), 3.53-3.39 (m, 4H), 1.93-1.61 (m, 7H), 1.61-1.50 (m, 3H), 1.27 (m, 5H), 0.92-0.79 (m, 5H). HPLC-MS (ES+) (method 20): MH+ m/z 481.0, RT 2.05 minutes.

Example 18

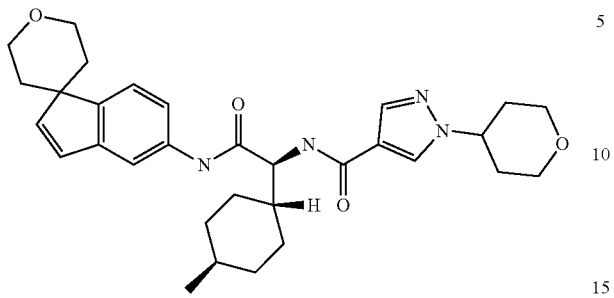

N-[(1S)-1-(trans-4-Methylcyclohexyl)-2-oxo-2-(spiro[indene-1,4'-tetrahydropyran]-5-ylamino)ethyl]-1-(tetrahydropyran-4-yl)pyrazole-4-carboxamide 1-(Tetrahydropyran-4-yl)pyrazole-4-carboxylic acid (19 mg, 0.099 mmol) was added to a solution of Intermediate 56 (35 mg, 0.099 mmol), HATU (46 mg, 0.12 mmol) and DIPEA (0.07 mL, 0.39 mmol) dissolved in DCM (2 mL). The reaction mixture was stirred for 1 h at r.t., then diluted with DCM (5 mL) and washed with water (1 mL). The organic phase was separated using a hydrophobic PTFE frit, and concentrated in vacuo. The resulting crude mixture was purified by preparative HPLC (method 22) to afford the title compound (27 mg, 51%) as a white solid. $\delta_H$ (400 MHz, DMSO-$d_6$) 10.13 (d, J 4.5 Hz, 1H), 8.40 (d, J 4.6 Hz, 1H), 8.07 (dd, J 8.6, 4.5 Hz, 1H), 7.97 (d, J 4.6 Hz, 1H), 7.67 (d, J 4.3 Hz, 1H), 7.38 (d, J 4.3 Hz, 2H), 7.13 (t, J 5.2 Hz, 1H), 6.81 (t, J 5.3 Hz, 1H), 4.42 (dt, J 10.1, 6.0 Hz, 2H), 4.20-3.85 (m, 4H), 3.83-3.61 (m, 2H), 2.25-1.82 (m, 8H), 1.74-1.53 (m, 4H), 1.35-1.08 (m, 2H), 1.18-1.09 (m, 4H), 0.91-0.79 (m, 5H). HPLC-MS (ES+) (method 20): MH+ m/z 533.4, RT 1.99 minutes.

The invention claimed is:

1. A compound of formula (I), or a pharmaceutically acceptable salt thereof:

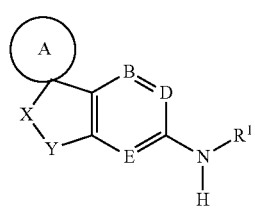
(I)

wherein
ring A represents $C_4$-$C_6$ heterocycloalkyl which group is optionally substituted by one or more substituents;
B represents C—$R^2$;
D represents C—$R^3$ or N;
E represents C—$R^4$;
—X—Y— represents —C($X^1$)($X^2$)—O—, —C($X^1$)($X^2$)—N($Y^3$)—, —C($X^1$)($X^2$)—C($Y^1$)($Y^2$)—, —C(O)—O—, or —C($X^1$)=C($Y^1$)—;
$R^1$ represents —COR$^a$;
$R^2$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^3$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^4$ represents hydrogen, halogen, cyano, $C_{1-6}$ alkyl, fluoromethyl, difluoromethyl, trifluoromethyl, hydroxy, $C_{1-6}$ alkoxy, difluoromethoxy, trifluoromethoxy, $C_{1-6}$ alkyl-sulphinyl or $C_{1-6}$ alkylsulphonyl;
$R^a$ represents —CH($R^5$)N(H)C(O)$R^6$ or —C(=C$R^{5a}R^{5b}$)N(H)C(O)$R^6$;
$R^5$ represents $C_{3-9}$ cycloalkyl, which group is optionally substituted by one or more substituents;
$R^{5a}$ represents $C_{3-7}$ cycloalkyl, $C_{4-9}$ bicycloalkyl, aryl, $C_{3-7}$ heterocycloalkyl or heteroaryl, any of which groups is optionally substituted by one or more substituents; and
$R^{5b}$ represents hydrogen or $C_{1-6}$ alkyl; or
$R^{5a}$ and $R^{5b}$, when taken together with the carbon atom to which they are both attached, represent $C_{3-7}$ cycloalkyl, $C_{4-9}$ bicycloalkyl or $C_{3-7}$ heterocycloalkyl, any of which groups is optionally substituted by one or more substituents;
$R^6$ represents aryl or heteroaryl, each of which groups is optionally substituted by one or more substituents;
$X^1$ represents hydrogen, halogen, cyano, $C_{1-6}$ alkyl, trifluoromethyl, ($C_{1-6}$)alkoxy-($C_{1-6}$)alkyl, amino($C_{1-6}$)alkyl, $C_{3-7}$ cycloalkyl, aryl, $C_{3-7}$ heterocycloalkyl or heteroaryl;
$X^2$ represents hydrogen, halogen or $C_{1-6}$ alkyl;
$Y^1$ represents hydrogen, halogen, cyano, $C_{1-6}$ alkyl, trifluoromethyl, ($C_{1-6}$)alkoxy-($C_{1-6}$)alkyl, amino($C_{1-6}$)alkyl, $C_{3-7}$ cycloalkyl, aryl, $C_{3-7}$ heterocycloalkyl or heteroaryl;
$Y^2$ represents hydrogen, halogen or $C_{1-6}$ alkyl; and
$Y^3$ represents hydrogen or $C_{1-6}$ alkyl.

2. A compound as claimed in claim 1 represented by formula (I-1) or (I-3), or a pharmaceutically acceptable salt thereof:

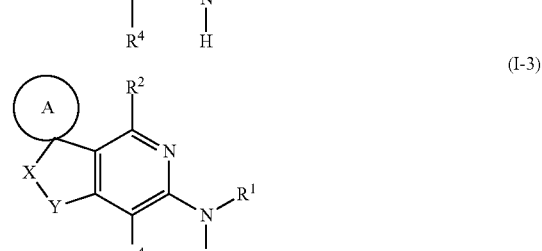

wherein A, X, Y, $R^1$, $R^2$, $R^3$ and $R^4$ are as defined in claim 1.

3. A compound as claimed in claim 1 represented by formula (I-11), (I-12), (I-13), (I-14) or (I-15), or a pharmaceutically acceptable salt thereof:

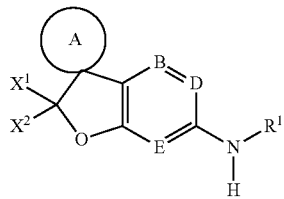
(I-11)

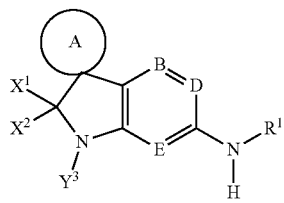
(I-12)

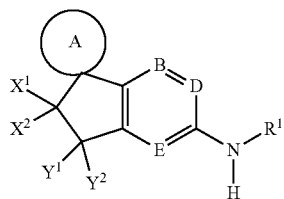
(I-13)

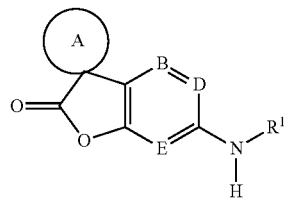
(I-14)

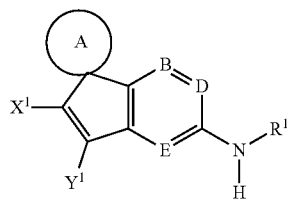
(I-15)

wherein A, B, D, E, $X^1$, $X^2$, $Y^1$, $Y^2$, $Y^3$ and $R^1$ are as defined in claim 1.

4. A compound as claimed in claim 1 represented by formula (IIA), or a pharmaceutically acceptable salt thereof:

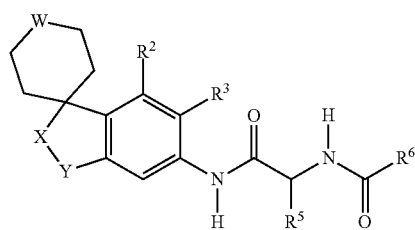
(IIA)

wherein
W represents O, S, S(O), S(O)$_2$, S(O)(NH) or N—$R^{17}$;
$R^{17}$ represents hydrogen or $C_{1-6}$ alkyl;
X, Y, $R^2$, $R^3$, $R^5$ and $R^6$ are as defined in claim 1.

5. A compound as claimed in claim 4 wherein $R^5$ represents $C_{3-9}$ cycloalkyl, which group may be optionally substituted by one, two or three substituents independently selected from $C_{1-6}$ alkyl.

6. A compound as claimed in claim 1 represented by formula (IIB), or a pharmaceutically acceptable salt thereof:

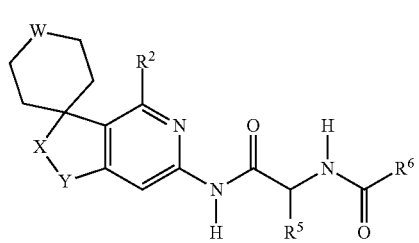
(IIB)

wherein
X, Y, $R^2$, $R^5$ and $R^6$ are as defined in claim 1; and
W represents O, S, S(O), S(O)$_2$, S(O)(NH) or N—$R^{17}$.

7. A compound as claimed in claim 6 wherein $R^5$ represents $C_{3-9}$ cycloalkyl, which group may be optionally substituted by one, two or three substituents independently selected from $C_{1-6}$ alkyl.

8. A compound as claimed in claim 6 wherein $R^6$ represents aryl or heteroaryl, either of which groups may be optionally substituted by one, two or three substituents independently selected from $C_1$-$C_6$ alkyl, ($C_1$-$C_6$)alkylsulfonyl-($C_1$-$C_6$)alkyl, dioxoisothiazolidinyl, tetrahydropyranyl, $C_1$-$C_6$ alkylsulfonylamino and di($C_1$-$C_6$)alkylsulfoximinyl.

9. A compound as claimed in claim 1 wherein $R^5$ represents $C_{3-9}$ cycloalkyl, which group may be optionally substituted by one, two or three substituents independently selected from $C_{1-6}$ alkyl.

10. A compound as claimed in claim 9 wherein $R^6$ represents aryl or heteroaryl, either of which groups may be optionally substituted by one, two or three substituents independently selected from $C_1$-$C_6$ alkyl, ($C_1$-$C_6$)alkylsulfonyl-($C_1$-$C_6$)alkyl, dioxoisothiazolidinyl, tetrahydropyranyl, $C_1$-$C_6$ alkylsulfonylamino and di($C_1$-$C_6$)alkylsulfoximinyl.

11. A compound as claimed in claim 1 wherein $R^6$ represents aryl or heteroaryl, either of which groups may be optionally substituted by one, two or three substituents independently selected from $C_{1-6}$ alkyl, ($C_{1-6}$)alkylsulfonyl ($C_{1-6}$)alkyl, dioxoisothiazolidinyl, tetrahydropyranyl, $C_{1-6}$ alkylsulfonylamino and di($C_{1-6}$)alkyl-sulfoximinyl.

12. A compound as claimed in claim 1 which is
2-Cyclooctyl-2-[(3-methylisoxazol-4-yl)formamido]-N-(spiro[indene-1,4'-oxane]-5-yl)-acetamide;
2-(5-Chlorobicyclo[4.2.0]octa-1,3,5-trien-7-ylidene)-2-[(1-ethyl-1H-pyrazol-5-yl)-formamido]-N-(spiro[indene-1,4'-oxane]-5-yl)acetamide;
N-[1-Cyclooctyl-2-oxo-2-(spiro[indane-1,4'-tetrahydropyran]-5-ylamino)ethyl]-3-methyl-isoxazole-4-carboxamide;
N-{1-Cyclooctyl-2-[(2-fluorospiro[indene-1,4'-tetrahydropyran]-5-yl)amino]-2-oxo-ethyl}-3-methylisoxazole-4-carboxamide;
N-[1-Cyclooctyl-2-oxo-2-(spiro[indoline-3,4'-tetrahydropyran]-6-ylamino)ethyl]-3-methylisoxazole-4-carboxamide;
2-Ethyl-N-[(1S)-1-(4-methylcyclohexyl)-2-oxo-2-(spiro[indoline-3,4'-tetrahydropyran]-6-ylamino)ethyl]pyrazole-3-carboxamide (trans isomer);

N-{1-Cyclooctyl-2-oxo-2-[(2-oxo-2',3',5',6'-tetrahydro-2H-spiro[benzofuran-3,4'-pyran]-6-yl)amino]ethyl}-3-methylisoxazole-4-carboxamide;

N-[1-Cyclooctyl-2-oxo-2-(spiro[2H-benzofuran-3,4'-tetrahydropyran]-6-ylamino)ethyl]-3-methylisoxazole-4-carboxamide;

3-(1,1-Dioxo-1,2-thiazolidin-2-yl)-N-{(1S)-2-[(4-fluorospiro[indoline-3,4'-tetrahydro-pyran]-6-yl)amino]-1-(trans-4-methylcyclohexyl)-2-oxoethyl}benzamide;

N-{(1S)-2-[(4-Fluorospiro[indoline-3,4'-tetrahydropyran]-6-yl)amino]-1-(trans-4-methyl-cyclohexyl)-2-oxoethyl}-3-(methylsulfonylmethyl)benzamide;

N-{(1S)-2-[(4-Fluorospiro[indoline-3,4'-tetrahydropyran]-6-yl)amino]-1-(trans-4-methyl-cyclohexyl)-2-oxoethyl}-3-(methanesulfonamido)benzamide;

4-Ethyl-N-{(1S)-2-[(4-fluorospiro[indoline-3,4'-tetrahydropyran]-6-yl)amino]-1-(trans-4-methylcyclohexyl)-2-oxoethyl}-1,2,5-oxadiazole-3-carboxamide;

3-{[Dimethyl(oxo)-$\lambda^6$-sulfanylidene]amino}-N-{(1S)-2-[(4-fluorospiro[indoline-3,4'-tetrahydropyran]-6-yl)amino]-1-(trans-4-methylcyclohexyl)-2-oxoethyl}benzamide;

(2S)-2-[(1-Ethyl-1H-pyrazol-5-yl)formamido]-N-(4-fluoro-1,2-dihydrospiro[indole-3,4'-oxane]-6-yl)-2-(trans-4-methylcyclohexyl)acetamide;

(2S)-2-{[1-(Propan-2-yl)-1H-pyrazol-5-yl]formamido}-2-(trans-4-methylcyclohexyl)-N-(spiro[indene-1,4'-oxane]-5-yl)acetamide;

3-{[Dimethyl(oxo)-$\lambda^6$-sulfanylidene]amino}-N-[(1S)-1-(trans-4-methylcyclohexyl)-2-oxo-2-(spiro[indene-1,4'-tetrahydropyran]-5-ylamino)ethyl]benzamide;

2-Ethyl-N-[(1S)-1-(trans-4-methylcyclohexyl)-2-oxo-2-(spiro[1,2-dihydropyrrolo[3,2-c]-pyridine-3,4'-tetrahydropyran]-6-ylamino)ethyl]pyrazole-3-carboxamide;

N-[(1S)-1-(trans-4-Methylcyclohexyl)-2-oxo-2-(spiro[indene-1,4'-tetrahydropyran]-5-ylamino)ethyl]-1-(tetrahydropyran-4-yl)pyrazole-4-carboxamide; or a pharmaceutically acceptable salt thereof.

13. A pharmaceutical composition comprising a compound of formula (I) as defined in claim 1, or a pharmaceutically acceptable salt thereof, in association with a pharmaceutically acceptable carrier.

14. A pharmaceutical composition as claimed in claim 13 further comprising an additional pharmaceutically active ingredient.

15. A method for the treatment of psoriasis, psoriatic arthritis or ankylosing spondylitis, which comprises administering to a patient in need of such treatment an effective amount of a compound of formula (I) as defined in claim 1, or a pharmaceutically acceptable salt thereof.

* * * * *